US009522962B2

(12) United States Patent
Ossendorp et al.

(10) Patent No.: US 9,522,962 B2
(45) Date of Patent: Dec. 20, 2016

(54) PEPTIDES, CONJUGATES AND METHOD FOR INCREASING IMMUNOGENICITY OF A VACCINE

(75) Inventors: Ferdinand Antonius Ossendorp, Amstelveen (NL); Cornelis Joseph Maria Melief, Haarlem (NL); Jan Wouter Drijfhout, Leiden (NL)

(73) Assignees: Academisch Ziekenhuis Leiden h.o.d.n. LUMC, Leiden (NL); Stichting voor de Technische Wetenschappen, Utrecht (NL)

( * ) Notice: Subject to any disclaimer, the term of this patent is extended or adjusted under 35 U.S.C. 154(b) by 337 days.

(21) Appl. No.: 13/635,384

(22) PCT Filed: Mar. 15, 2011

(86) PCT No.: PCT/NL2011/050180
§ 371 (c)(1),
(2), (4) Date: Dec. 3, 2012

(87) PCT Pub. No.: WO2011/115483
PCT Pub. Date: Sep. 22, 2011

(65) Prior Publication Data
US 2013/0071428 A1 Mar. 21, 2013

Related U.S. Application Data

(60) Provisional application No. 61/317,930, filed on Mar. 26, 2010.

(30) Foreign Application Priority Data

Mar. 15, 2010 (EP) .................................... 10156505

(51) Int. Cl.

| | |
|---|---|
| *A61K 39/00* | (2006.01) |
| *C07K 17/02* | (2006.01) |
| *A61K 39/385* | (2006.01) |
| *A61K 39/40* | (2006.01) |
| *C07K 14/33* | (2006.01) |
| *C07K 16/12* | (2006.01) |
| *C07K 7/08* | (2006.01) |

(52) U.S. Cl.
CPC ............ *C07K 17/02* (2013.01); *A61K 39/385* (2013.01); *A61K 39/40* (2013.01); *C07K 7/08* (2013.01); *C07K 14/33* (2013.01); *C07K 16/1282* (2013.01); *A61K 39/00* (2013.01); *A61K 2039/6037* (2013.01); *A61K 2039/627* (2013.01)

(58) Field of Classification Search
None
See application file for complete search history.

(56) References Cited

U.S. PATENT DOCUMENTS 5,595,756 A * 1/1997 Bally .................. A61K 9/1272 264/4.1
6,372,225 B1 * 4/2002 Matsuda .................... 424/236.1

FOREIGN PATENT DOCUMENTS

WO WO 9518148 A1 * 7/1995
WO WO-04/000873 A2 12/2003
WO WO-2008/118487 10/2008

OTHER PUBLICATIONS

Bowie et al. (Science, 1990, 247:1306-1310).*
Greenspan et al. (Nature Biotechnology 7: 936-937, 1999).*
Sporn et al, “Chemoprevention of Cancer,” Carcinogenesis, vol. 21 (2000), 525-530.*
Auerbach et al (Cancer and Metastasis Reviews, 2000, 19: 167-172).*
Gura T (Science, 1997, 278(5340): 1041-1042.*
Jain RK (Scientific American, Jul. 1994,58-65).*
Abdel-Motal et al. “Mechanism for increased immunogenicity of vaccines that form in vivo immune complexes with the natural anti-Gal antibody”, Vaccine, (2009) vol. 27:3072-3082.
Banchereau et al. “Dendritic cells and the control of immunity”, Nature,(Mar. 19, 1998) vol. 392, pp. 245-252.
Gosselin et al. “Enhanced Antigen Presentation Using Human Fcγ Receptor (Monocyte/Macrophage)-Specific Immunogens”, The Journal of Immunology,(Dec. 1, 1992) vol. 149, No. 11, pp. 3477-3481.
Ravetch, et al. “Divergent Roles for Fc Receptors and Complement In Vivo”, Annu. Rev. Immunol.,(1998) vol. 16:421-432.
Schuurhuis, et al. “Antigen-Antibody Immune Complexes Empower Dendritic Cells to Efficiently Prime Specific CD8+ CTL Responses In Vivo”, The Journal of Immunology,(2002), vol. 168, pp. 2240-2246.
Zinkernagel, et al. “Antigen localisation regulates immune responses in a dose-and time-dependent fashion: a geographical view of immune reactivity”,(1997), Immunological Reviews, vol. 156, pp. 199-209.
Perry, et al. “Comparison of Five Commercial Anti-Tetanus Toxoid Immunoglobulin G Enzyme-Linked Immunosorbent Assays”, Clinical and Vaccine Immunology (2009), vol. 16, No. 12, pp. 1837-1839.
Demotz S et al: “Delineation of Several DR-Restricted Tetanus Toxin T Cell Epitopes”, Journal of Immunology, American Association of Immunologists, US, vol. 142, No. 2, Jan. 15, 1989, pp. 394-402, XP002025350.
Engstrom Per-Erik et al: “Quantitative analysis of IgA-subclass antibodies against tetanus toxoid”, Journal of Immunoassay, vol. 16, No. 3, 1995, pp. 231-245, XP007196758.

(Continued)

*Primary Examiner* — Brian J Gangle
(74) *Attorney, Agent, or Firm* — Foley & Lardner; Sunit Talapatra

(57) ABSTRACT

The present invention relates to conjugates comprising a peptide of at least 10 amino acid residues comprising the amino acid sequence GITELKKL (residues 383-390 of SEQ ID NO: 3) for induction of potent humoral and cellular immune responses when administered to subjects having antibodies against tetanus toxoid. In one embodiment the invention relates to a prophylactic and therapeutic vaccine and in a further embodiment the invention relates to the treatment or prevention of cancer or an infectious disease.

16 Claims, 12 Drawing Sheets

(56) References Cited

OTHER PUBLICATIONS

Fischer P M et al: "Synthetic Peptide Antigens of Tetanus Toxin", Molecular Immunology, Pergamon, GB, vol. 31, No. 15, Oct. 1, 1994, pp. 1141-1148, XP001068825.

International Search Report for PCT/NL2011/050180—mailed Jul. 25, 2011.

Raju R et al: "Epitoope Repertoire of Human CD4<+> Lines Propagated with Tetanus Toxoid or with Synthetic Tetanus Toxin Sequences", Journal of Autoimmunity, London, GB, vol. 9, No. 1, Feb. 1, 1996, pp. 79-88, XP027373176.

Van Der Burg S H et al: "Improved peptide vaccine strategies, creating synthetic artificial infections to maximize immune efficacy", Advanced Drug Delivery Reviews, Elsevier, BV, Amsterdam NL, vol. 58, No. 8, Oct. 1, 2006, pp. 916-930, XP02482126.

Volk W A et al: "Neutralization of Tetanus Toxin by Distinct Monoclonal Antibodies Binding to Multiple Epitopes on the Toxin Molecule", Infection and Immunity, American Society for Microbiology, Washington, US, vol. 45, No. 3, Sep. 1, 1984, pp. 604-609, XP001068827.

* cited by examiner

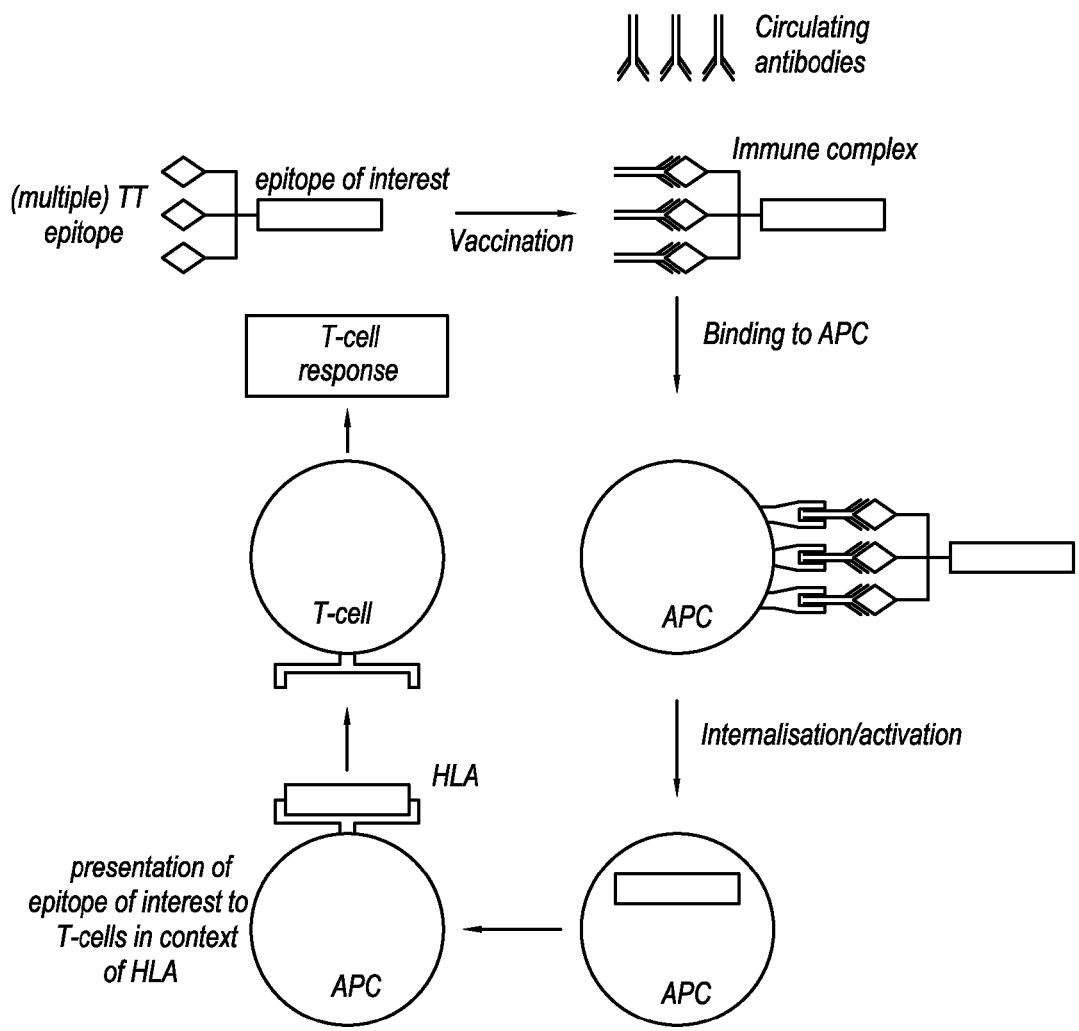

SEQUENCE LISTING

```
<160> NUMBER OF SEQ ID NOS: 262

<210> SEQ ID NO 1
<211> LENGTH: 1314
<212> TYPE: PRT
<213> ORGANISM: Clostridium tetani

<400> SEQUENCE: 1

Pro Ile Thr Ile Asn Asn Phe Arg Tyr Ser Asp Pro Val Asn Asn Asp
1               5                   10                  15

Thr Ile Ile Met Met Glu Pro Pro Tyr Cys Lys Gly Leu Asp Ile Tyr
            20                  25                  30

Tyr Lys Ala Phe Lys Ile Thr Asp Arg Ile Trp Ile Val Pro Glu Arg
        35                  40                  45

Tyr Glu Phe Gly Thr Lys Pro Glu Asp Phe Asn Pro Pro Ser Ser Leu
    50                  55                  60

Ile Glu Gly Ala Ser Glu Tyr Tyr Asp Pro Asn Tyr Leu Arg Thr Asp
65                  70                  75                  80

Ser Asp Lys Asp Arg Phe Leu Gln Thr Met Val Lys Leu Phe Asn Arg
                85                  90                  95

Ile Lys Asn Asn Val Ala Gly Glu Ala Leu Leu Asp Lys Ile Ile Asn
            100                 105                 110
```

```
Ala Ile Pro Tyr Leu Gly Asn Ser Tyr Ser Leu Leu Asp Lys Phe Asp
            115                 120                 125

Thr Asn Ser Asn Ser Val Ser Phe Asn Leu Leu Glu Gln Asp Pro Ser
130                 135                 140

Gly Ala Thr Thr Lys Ser Ala Met Leu Thr Asn Leu Ile Ile Phe Gly
145                 150                 155                 160

Pro Gly Pro Val Leu Asn Lys Asn Glu Val Arg Gly Ile Val Leu Arg
                165                 170                 175

Val Asp Asn Lys Asn Tyr Phe Pro Cys Arg Asp Gly Phe Gly Ser Ile
            180                 185                 190

Met Gln Met Ala Phe Cys Pro Glu Tyr Val Pro Thr Phe Asp Asn Val
        195                 200                 205

Ile Glu Asn Ile Thr Ser Leu Thr Ile Gly Lys Ser Lys Tyr Phe Gln
210                 215                 220

Asp Pro Ala Leu Leu Leu Met His Glu Leu Ile His Val Leu His Gly
225                 230                 235                 240

Leu Tyr Gly Met Gln Val Ser Ser His Glu Ile Ile Pro Ser Lys Gln
                245                 250                 255

Glu Ile Tyr Met Gln His Thr Tyr Pro Ile Ser Ala Glu Glu Leu Phe
            260                 265                 270

Thr Phe Gly Gly Gln Asp Ala Asn Leu Ile Ser Ile Asp Ile Lys Asn
        275                 280                 285

Asp Leu Tyr Glu Lys Thr Leu Asn Asp Tyr Lys Ala Ile Ala Asn Lys
        290                 295                 300

Leu Ser Gln Val Thr Ser Cys Asn Asp Pro Asn Ile Asp Ile Asp Ser
305                 310                 315                 320

Tyr Lys Gln Ile Tyr Gln Gln Lys Tyr Gln Phe Asp Lys Asp Ser Asn
                325                 330                 335

Gly Gln Tyr Ile Val Asn Glu Asp Lys Phe Gln Ile Leu Tyr Asn Ser
            340                 345                 350

Ile Met Tyr Gly Phe Thr Glu Ile Glu Leu Gly Lys Lys Phe Asn Ile
        355                 360                 365

Lys Thr Arg Leu Ser Tyr Phe Ser Met Asn His Asp Pro Val Lys Ile
370                 375                 380

Pro Asn Leu Leu Asp Asp Thr Ile Tyr Asn Asp Thr Glu Gly Phe Asn
385                 390                 395                 400

Ile Glu Ser Lys Asp Leu Lys Ser Glu Tyr Lys Gly Gln Asn Met Arg
                405                 410                 415

Val Asn Thr Asn Ala Phe Arg Asn Val Asp Gly Ser Gly Leu Val Ser
            420                 425                 430

Lys Leu Ile Gly Leu Cys Lys Lys Ile Ile Pro Pro Thr Asn Ile Arg
        435                 440                 445

Glu Asn Leu Tyr Asn Arg Thr Ala Ser Leu Thr Asp Leu Gly Gly Glu
450                 455                 460

Leu Cys Ile Lys Ile Lys Asn Glu Asp Leu Thr Phe Ile Ala Glu Lys
465                 470                 475                 480

Asn Ser Phe Ser Glu Glu Pro Phe Gln Asp Glu Ile Val Ser Tyr Asn
                485                 490                 495

Thr Lys Asn Lys Pro Leu Asn Phe Asn Tyr Ser Leu Asp Lys Ile Ile
            500                 505                 510

Val Asp Tyr Asn Leu Gln Ser Lys Ile Thr Leu Pro Asn Asp Arg Thr
        515                 520                 525

Thr Pro Val Thr Lys Gly Ile Pro Tyr Ala Pro Glu Tyr Lys Ser Asn
```

```
            530                 535                 540
Ala Ala Ser Thr Ile Glu Ile His Asn Ile Asp Asp Asn Thr Ile Tyr
545                 550                 555                 560

Gln Tyr Leu Tyr Ala Gln Lys Ser Pro Thr Thr Leu Gln Arg Ile Thr
                565                 570                 575

Met Thr Asn Ser Val Asp Asp Ala Leu Ile Asn Ser Thr Lys Ile Tyr
                580                 585                 590

Ser Tyr Phe Pro Ser Val Ile Ser Lys Val Asn Gln Gly Ala Gln Gly
            595                 600                 605

Ile Leu Phe Leu Gln Trp Val Arg Asp Ile Ile Asp Asp Phe Thr Asn
610                 615                 620

Glu Ser Ser Gln Lys Thr Thr Ile Asp Lys Ile Ser Asp Val Ser Thr
625                 630                 635                 640

Ile Val Pro Tyr Ile Gly Pro Ala Leu Asn Ile Val Lys Gln Gly Tyr
                645                 650                 655

Glu Gly Asn Phe Ile Gly Ala Leu Glu Thr Thr Gly Val Val Leu Leu
                660                 665                 670

Leu Glu Tyr Ile Pro Glu Ile Thr Leu Pro Val Ile Ala Ala Leu Ser
            675                 680                 685

Ile Ala Glu Ser Ser Thr Gln Lys Glu Lys Ile Ile Lys Thr Ile Asp
690                 695                 700

Asn Phe Leu Glu Lys Arg Tyr Glu Lys Trp Ile Glu Val Tyr Lys Leu
705                 710                 715                 720

Val Lys Ala Lys Trp Leu Gly Thr Val Asn Thr Gln Phe Gln Lys Arg
                725                 730                 735

Ser Tyr Gln Met Tyr Arg Ser Leu Glu Tyr Gln Val Asp Ala Ile Lys
                740                 745                 750

Lys Ile Ile Asp Tyr Glu Tyr Lys Ile Tyr Ser Gly Pro Asp Lys Glu
            755                 760                 765

Gln Ile Ala Asp Glu Ile Asn Asn Leu Lys Asn Lys Leu Glu Glu Lys
770                 775                 780

Ala Asn Lys Ala Met Ile Asn Ile Asn Ile Phe Met Arg Glu Ser Ser
785                 790                 795                 800

Arg Ser Phe Leu Val Asn Gln Met Ile Asn Glu Ala Lys Lys Gln Leu
                805                 810                 815

Leu Glu Phe Asp Thr Gln Ser Lys Asn Ile Leu Met Gln Tyr Ile Lys
                820                 825                 830

Ala Asn Ser Lys Phe Ile Gly Ile Thr Glu Leu Lys Lys Leu Glu Ser
            835                 840                 845

Lys Ile Asn Lys Val Phe Ser Thr Pro Ile Pro Phe Ser Tyr Ser Lys
850                 855                 860

Asn Leu Asp Cys Trp Val Asp Asn Glu Glu Asp Ile Asp Val Ile Leu
865                 870                 875                 880

Lys Lys Ser Thr Ile Leu Asn Leu Asp Ile Asn Asn Asp Ile Ile Ser
                885                 890                 895

Asp Ile Ser Gly Phe Asn Ser Ser Val Ile Thr Tyr Pro Asp Ala Gln
            900                 905                 910

Leu Val Pro Gly Ile Asn Gly Lys Ala Ile His Leu Val Asn Asn Glu
            915                 920                 925

Ser Ser Glu Val Ile Val His Lys Ala Met Asp Ile Glu Tyr Asn Asp
930                 935                 940

Met Phe Asn Asn Phe Thr Val Ser Phe Trp Leu Arg Val Pro Lys Val
945                 950                 955                 960
```

```
Ser Ala Ser His Leu Glu Gln Tyr Gly Thr Asn Glu Tyr Ser Ile Ile
            965                 970                 975

Ser Ser Met Lys Lys His Ser Leu Ser Ile Gly Ser Gly Trp Ser Val
            980                 985                 990

Ser Leu Lys Gly Asn Asn Leu Ile Trp Thr Leu Lys Asp Ser Ala Gly
            995                 1000                1005

Glu Val Arg Gln Ile Thr Phe Arg Asp Leu Pro Asp Lys Phe Asn
        1010                1015                1020

Ala Tyr Leu Ala Asn Lys Trp Val Phe Ile Thr Ile Thr Asn Asp
        1025                1030                1035

Arg Leu Ser Ser Ala Asn Leu Tyr Ile Asn Gly Val Leu Met Gly
        1040                1045                1050

Ser Ala Glu Ile Thr Gly Leu Gly Ala Ile Arg Glu Asp Asn Asn
        1055                1060                1065

Ile Thr Leu Lys Leu Asp Arg Cys Asn Asn Asn Gln Tyr Val
        1070                1075                1080

Ser Ile Asp Lys Phe Arg Ile Phe Cys Lys Ala Leu Asn Pro Lys
        1085                1090                1095

Glu Ile Glu Lys Leu Tyr Thr Ser Tyr Leu Ser Ile Thr Phe Leu
        1100                1105                1110

Arg Asp Phe Trp Gly Asn Pro Leu Arg Tyr Asp Thr Glu Tyr Tyr
        1115                1120                1125

Leu Ile Pro Val Ala Ser Ser Lys Asp Val Gln Leu Lys Asn
        1130                1135                1140

Ile Thr Asp Tyr Met Tyr Leu Thr Asn Ala Pro Ser Tyr Thr Asn
        1145                1150                1155

Gly Lys Leu Asn Ile Tyr Tyr Arg Arg Leu Tyr Asn Gly Leu Lys
        1160                1165                1170

Phe Ile Ile Lys Arg Tyr Thr Pro Asn Asn Glu Ile Asp Ser Phe
        1175                1180                1185

Val Lys Ser Gly Asp Phe Ile Lys Leu Tyr Val Ser Tyr Asn Asn
        1190                1195                1200

Asn Glu His Ile Val Gly Tyr Pro Lys Asp Gly Asn Ala Phe Asn
        1205                1210                1215

Asn Leu Asp Arg Ile Leu Arg Val Gly Tyr Asn Ala Pro Gly Ile
        1220                1225                1230

Pro Leu Tyr Lys Lys Met Glu Ala Val Lys Leu Arg Asp Leu Lys
        1235                1240                1245

Thr Tyr Ser Val Gln Leu Lys Leu Tyr Asp Asp Lys Asn Ala Ser
        1250                1255                1260

Leu Gly Leu Val Gly Thr His Asn Gly Gln Ile Gly Asn Asp Pro
        1265                1270                1275

Asn Arg Asp Ile Leu Ile Ala Ser Asn Trp Tyr Phe Asn His Leu
        1280                1285                1290

Lys Asp Lys Ile Leu Gly Cys Asp Trp Tyr Phe Val Pro Thr Asp
        1295                1300                1305

Glu Gly Trp Thr Asn Asp
        1310

<210> SEQ ID NO 2
<211> LENGTH: 456
<212> TYPE: PRT
<213> ORGANISM: Clostridium tetani
```

<400> SEQUENCE: 2

```
Pro Ile Thr Ile Asn Asn Phe Arg Tyr Ser Asp Pro Val Asn Asp
1               5                   10                  15

Thr Ile Ile Met Met Glu Pro Pro Tyr Cys Lys Gly Leu Asp Ile Tyr
            20                  25                  30

Tyr Lys Ala Phe Lys Ile Thr Asp Arg Ile Trp Ile Val Pro Glu Arg
        35                  40                  45

Tyr Glu Phe Gly Thr Lys Pro Glu Asp Phe Asn Pro Pro Ser Ser Leu
    50                  55                  60

Ile Glu Gly Ala Ser Glu Tyr Tyr Asp Pro Asn Tyr Leu Arg Thr Asp
65                  70                  75                  80

Ser Asp Lys Asp Arg Phe Leu Gln Thr Met Val Lys Leu Phe Asn Arg
                85                  90                  95

Ile Lys Asn Asn Val Ala Gly Glu Ala Leu Leu Asp Lys Ile Ile Asn
            100                 105                 110

Ala Ile Pro Tyr Leu Gly Asn Ser Tyr Ser Leu Leu Asp Lys Phe Asp
        115                 120                 125

Thr Asn Ser Asn Ser Val Ser Phe Asn Leu Leu Glu Gln Asp Pro Ser
130                 135                 140

Gly Ala Thr Thr Lys Ser Ala Met Leu Thr Asn Leu Ile Ile Phe Gly
145                 150                 155                 160

Pro Gly Pro Val Leu Asn Lys Asn Glu Val Arg Gly Ile Val Leu Arg
                165                 170                 175

Val Asp Asn Lys Asn Tyr Phe Pro Cys Arg Asp Gly Phe Gly Ser Ile
            180                 185                 190

Met Gln Met Ala Phe Cys Pro Glu Tyr Val Pro Thr Phe Asp Asn Val
        195                 200                 205

Ile Glu Asn Ile Thr Ser Leu Thr Ile Gly Lys Ser Lys Tyr Phe Gln
    210                 215                 220

Asp Pro Ala Leu Leu Leu Met His Glu Leu Ile His Val Leu His Gly
225                 230                 235                 240

Leu Tyr Gly Met Gln Val Ser Ser His Glu Ile Ile Pro Ser Lys Gln
                245                 250                 255

Glu Ile Tyr Met Gln His Thr Tyr Pro Ile Ser Ala Glu Glu Leu Phe
            260                 265                 270

Thr Phe Gly Gly Gln Asp Ala Asn Leu Ile Ser Ile Asp Ile Lys Asn
        275                 280                 285

Asp Leu Tyr Glu Lys Thr Leu Asn Asp Tyr Lys Ala Ile Ala Asn Lys
290                 295                 300

Leu Ser Gln Val Thr Ser Cys Asn Asp Pro Asn Ile Asp Ile Asp Ser
305                 310                 315                 320

Tyr Lys Gln Ile Tyr Gln Gln Lys Tyr Gln Phe Asp Lys Asp Ser Asn
                325                 330                 335

Gly Gln Tyr Ile Val Asn Glu Asp Lys Phe Gln Ile Leu Tyr Asn Ser
            340                 345                 350

Ile Met Tyr Gly Phe Thr Glu Ile Glu Leu Gly Lys Lys Phe Asn Ile
        355                 360                 365

Lys Thr Arg Leu Ser Tyr Phe Ser Met Asn His Asp Pro Val Lys Ile
        370                 375                 380

Pro Asn Leu Leu Asp Asp Thr Ile Tyr Asn Asp Thr Glu Gly Phe Asn
385                 390                 395                 400

Ile Glu Ser Lys Asp Leu Lys Ser Glu Tyr Lys Gly Gln Asn Met Arg
                405                 410                 415
```

```
Val Asn Thr Asn Ala Phe Arg Asn Val Asp Gly Ser Gly Leu Val Ser
            420                 425                 430

Lys Leu Ile Gly Leu Cys Lys Lys Ile Ile Pro Pro Thr Asn Ile Arg
            435                 440                 445

Glu Asn Leu Tyr Asn Arg Thr Ala
            450                 455

<210> SEQ ID NO 3
<211> LENGTH: 858
<212> TYPE: PRT
<213> ORGANISM: Clostridium tetani

<400> SEQUENCE: 3

Ser Leu Thr Asp Leu Gly Gly Glu Leu Cys Ile Lys Ile Lys Asn Glu
1               5                   10                  15

Asp Leu Thr Phe Ile Ala Glu Lys Asn Ser Phe Ser Glu Glu Pro Phe
            20                  25                  30

Gln Asp Glu Ile Val Ser Tyr Asn Thr Lys Asn Lys Pro Leu Asn Phe
            35                  40                  45

Asn Tyr Ser Leu Asp Lys Ile Ile Val Asp Tyr Asn Leu Gln Ser Lys
        50                  55                  60

Ile Thr Leu Pro Asn Asp Arg Thr Thr Pro Val Thr Lys Gly Ile Pro
65                  70                  75                  80

Tyr Ala Pro Glu Tyr Lys Ser Asn Ala Ala Ser Thr Ile Glu Ile His
                85                  90                  95

Asn Ile Asp Asp Asn Thr Ile Tyr Gln Tyr Leu Tyr Ala Gln Lys Ser
            100                 105                 110

Pro Thr Thr Leu Gln Arg Ile Thr Met Thr Asn Ser Val Asp Asp Ala
            115                 120                 125

Leu Ile Asn Ser Thr Lys Ile Tyr Ser Tyr Phe Pro Ser Val Ile Ser
        130                 135                 140

Lys Val Asn Gln Gly Ala Gln Gly Ile Leu Phe Leu Gln Trp Val Arg
145                 150                 155                 160

Asp Ile Ile Asp Asp Phe Thr Asn Glu Ser Ser Gln Lys Thr Thr Ile
                165                 170                 175

Asp Lys Ile Ser Asp Val Ser Thr Ile Val Pro Tyr Ile Gly Pro Ala
            180                 185                 190

Leu Asn Ile Val Lys Gln Gly Tyr Glu Gly Asn Phe Ile Gly Ala Leu
        195                 200                 205

Glu Thr Thr Gly Val Val Leu Leu Leu Glu Tyr Ile Pro Glu Ile Thr
    210                 215                 220

Leu Pro Val Ile Ala Ala Leu Ser Ile Ala Glu Ser Ser Thr Gln Lys
225                 230                 235                 240

Glu Lys Ile Ile Lys Thr Ile Asp Asn Phe Leu Glu Lys Arg Tyr Glu
                245                 250                 255

Lys Trp Ile Glu Val Tyr Lys Leu Val Lys Ala Lys Trp Leu Gly Thr
            260                 265                 270

Val Asn Thr Gln Phe Gln Lys Arg Ser Tyr Gln Met Tyr Arg Ser Leu
        275                 280                 285

Glu Tyr Gln Val Asp Ala Ile Lys Lys Ile Ile Asp Tyr Glu Tyr Lys
    290                 295                 300

Ile Tyr Ser Gly Pro Asp Lys Glu Gln Ile Ala Asp Glu Ile Asn Asn
305                 310                 315                 320

Leu Lys Asn Lys Leu Glu Glu Lys Ala Asn Lys Ala Met Ile Asn Ile
```

```
                    325                 330                 335
Asn Ile Phe Met Arg Glu Ser Ser Arg Ser Phe Leu Val Asn Gln Met
                340                 345                 350
Ile Asn Glu Ala Lys Lys Gln Leu Leu Glu Phe Asp Thr Gln Ser Lys
                355                 360                 365
Asn Ile Leu Met Gln Tyr Ile Lys Ala Asn Ser Lys Phe Ile Gly Ile
                370                 375                 380
Thr Glu Leu Lys Lys Leu Glu Ser Lys Ile Asn Lys Val Phe Ser Thr
385                 390                 395                 400
Pro Ile Pro Phe Ser Tyr Ser Lys Asn Leu Asp Cys Trp Val Asp Asn
                405                 410                 415
Glu Glu Asp Ile Asp Val Ile Leu Lys Lys Ser Thr Ile Leu Asn Leu
                420                 425                 430
Asp Ile Asn Asn Asp Ile Ile Ser Asp Ile Ser Gly Phe Asn Ser Ser
                435                 440                 445
Val Ile Thr Tyr Pro Asp Ala Gln Leu Val Pro Gly Ile Asn Gly Lys
                450                 455                 460
Ala Ile His Leu Val Asn Asn Glu Ser Ser Glu Val Ile Val His Lys
465                 470                 475                 480
Ala Met Asp Ile Glu Tyr Asn Asp Met Phe Asn Asn Phe Thr Val Ser
                485                 490                 495
Phe Trp Leu Arg Val Pro Lys Val Ser Ala Ser His Leu Glu Gln Tyr
                500                 505                 510
Gly Thr Asn Glu Tyr Ser Ile Ile Ser Ser Met Lys Lys His Ser Leu
                515                 520                 525
Ser Ile Gly Ser Gly Trp Ser Val Ser Leu Lys Gly Asn Asn Leu Ile
                530                 535                 540
Trp Thr Leu Lys Asp Ser Ala Gly Glu Val Arg Gln Ile Thr Phe Arg
545                 550                 555                 560
Asp Leu Pro Asp Lys Phe Asn Ala Tyr Leu Ala Asn Lys Trp Val Phe
                565                 570                 575
Ile Thr Ile Thr Asn Asp Arg Leu Ser Ser Ala Asn Leu Tyr Ile Asn
                580                 585                 590
Gly Val Leu Met Gly Ser Ala Glu Ile Thr Gly Leu Gly Ala Ile Arg
                595                 600                 605
Glu Asp Asn Asn Ile Thr Leu Lys Leu Asp Arg Cys Asn Asn Asn Asn
                610                 615                 620
Gln Tyr Val Ser Ile Asp Lys Phe Arg Ile Phe Cys Lys Ala Leu Asn
625                 630                 635                 640
Pro Lys Glu Ile Glu Lys Leu Tyr Thr Ser Tyr Leu Ser Ile Thr Phe
                645                 650                 655
Leu Arg Asp Phe Trp Gly Asn Pro Leu Arg Tyr Asp Thr Glu Tyr Tyr
                660                 665                 670
Leu Ile Pro Val Ala Ser Ser Lys Asp Val Gln Leu Lys Asn Ile
                675                 680                 685
Thr Asp Tyr Met Tyr Leu Thr Asn Ala Pro Ser Tyr Thr Asn Gly Lys
                690                 695                 700
Leu Asn Ile Tyr Tyr Arg Arg Leu Tyr Asn Gly Leu Lys Phe Ile Ile
705                 710                 715                 720
Lys Arg Tyr Thr Pro Asn Asn Glu Ile Asp Ser Phe Val Lys Ser Gly
                725                 730                 735
Asp Phe Ile Lys Leu Tyr Val Ser Tyr Asn Asn Asn Glu His Ile Val
                740                 745                 750
```

```
Gly Tyr Pro Lys Asp Gly Asn Ala Phe Asn Asn Leu Asp Arg Ile Leu
            755                 760                 765

Arg Val Gly Tyr Asn Ala Pro Gly Ile Pro Leu Tyr Lys Lys Met Glu
    770                 775                 780

Ala Val Lys Leu Arg Asp Leu Lys Thr Tyr Ser Val Gln Leu Lys Leu
785                 790                 795                 800

Tyr Asp Asp Lys Asn Ala Ser Leu Gly Leu Val Gly Thr His Asn Gly
                805                 810                 815

Gln Ile Gly Asn Asp Pro Asn Arg Asp Ile Leu Ile Ala Ser Asn Trp
            820                 825                 830

Tyr Phe Asn His Leu Lys Asp Lys Ile Leu Gly Cys Asp Trp Tyr Phe
                835                 840                 845

Val Pro Thr Asp Glu Gly Trp Thr Asn Asp
    850                 855

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Ile Gly Ile Thr Glu Leu Lys Lys Leu
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Ile Thr Glu Leu Lys Lys Leu Glu Ser
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Gly Ile Thr Glu Leu Lys Lys Leu Glu
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Lys Phe Ile Gly Ile Thr Glu Leu Lys Lys Leu
1               5                   10
```

```
<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Ile Gly Ile Thr Glu Leu Lys Lys Leu Glu Ser
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ile Thr Glu Leu Lys Lys Leu Glu Ser Lys Ile
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Tyr Ile Lys Ala Asn Ser Lys Phe Ile Gly Ile Thr Glu
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Asn Ser Lys Phe Ile Gly Ile Thr Glu Leu Lys Lys Leu
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Lys Phe Ile Gly Ile Thr Glu Leu Lys Lys Leu Glu Ser
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13
```

```
Phe Ile Gly Ile Thr Glu Leu Lys Lys Leu Glu Ser Lys Ile
1               5                   10
```

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Gln Tyr Ile Lys Ala Asn Ser Lys Phe Ile Gly Ile Thr Glu Leu Lys
1               5                   10                  15
```

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Ile Lys Ala Asn Ser Lys Phe Ile Gly Ile Thr Glu Leu Lys Lys Leu
1               5                   10                  15
```

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Ala Asn Ser Lys Phe Ile Gly Ile Thr Glu Leu Lys Lys Leu Glu Ser
1               5                   10                  15
```

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Ser Lys Phe Ile Gly Ile Thr Glu Leu Lys Lys Leu Glu Ser Lys Ile
1               5                   10                  15
```

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Gln Tyr Ile Lys Ala Asn Ser Lys Phe Ile Gly Ile Thr Glu Leu Lys
1               5                   10                  15

Lys Leu
```

<210> SEQ ID NO 19
<211> LENGTH: 18

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Lys Ala Asn Ser Lys Phe Ile Gly Ile Thr Glu Leu Lys Lys Leu
1               5                   10                  15

Glu Ser

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Asn Ser Lys Phe Ile Gly Ile Thr Glu Leu Lys Lys Leu Glu Ser
1               5                   10                  15

Lys Ile

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Tyr Ile Lys Ala Asn Ser Lys Phe Ile Gly Ile Thr Glu Leu Lys
1               5                   10                  15

Lys Leu Glu Ser
            20

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Lys Ala Asn Ser Lys Phe Ile Gly Ile Thr Glu Leu Lys Lys Leu
1               5                   10                  15

Glu Ser Lys Ile
            20

<210> SEQ ID NO 23
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Tyr Ile Lys Ala Asn Ser Lys Phe Ile Gly Ile Thr Glu Leu Lys
1               5                   10                  15

Lys Leu Glu Ser Lys Ile
            20
```

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Phe Ile Gly Ile Thr Glu Leu Lys Lys Leu Glu Ser Lys Ile Asn Lys
1               5                   10                  15

Val Phe

<210> SEQ ID NO 25
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 25

Pro Ile Thr Ile Asn Asn Phe Arg Tyr Ser Asp Pro Val Asn Asn Asp
1               5                   10                  15

Thr Ile Ile Met Met Glu Xaa Lys
            20

<210> SEQ ID NO 26
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 26

Val Asn Asn Asp Thr Ile Ile Met Met Glu Pro Pro Tyr Cys Lys Gly
1               5                   10                  15

Leu Asp Ile Tyr Tyr Lys Xaa Lys
            20

<210> SEQ ID NO 27
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid

```
<220> FEATURE:
<221> NAME/KEY: MOD_RES
<222> LOCATION: (24)..(24)
<223> OTHER INFORMATION: Lys(biotin)-amide

<400> SEQUENCE: 27

Tyr Cys Lys Gly Leu Asp Ile Tyr Tyr Lys Ala Phe Lys Ile Thr Asp
1               5                   10                  15

Arg Ile Trp Ile Val Pro Xaa Lys
            20

<210> SEQ ID NO 28
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 28

Lys Ile Thr Asp Arg Ile Trp Ile Val Pro Glu Arg Tyr Glu Phe Gly
1               5                   10                  15

Thr Lys Pro Glu Asp Phe Xaa Lys
            20

<210> SEQ ID NO 29
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 29

Tyr Glu Phe Gly Thr Lys Pro Glu Asp Phe Asn Pro Pro Ser Ser Leu
1               5                   10                  15

Ile Glu Gly Ala Ser Glu Xaa Lys
            20

<210> SEQ ID NO 30
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide
```

```
<400> SEQUENCE: 30

Pro Ser Ser Leu Ile Glu Gly Ala Ser Glu Tyr Tyr Asp Pro Asn Tyr
1               5                   10                  15

Leu Arg Thr Asp Ser Asp Xaa Lys
            20

<210> SEQ ID NO 31
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 31

Asp Pro Asn Tyr Leu Arg Thr Asp Ser Asp Lys Asp Arg Phe Leu Gln
1               5                   10                  15

Thr Met Val Lys Leu Phe Xaa Lys
            20

<210> SEQ ID NO 32
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 32

Arg Phe Leu Gln Thr Met Val Lys Leu Phe Asn Arg Ile Lys Asn Asn
1               5                   10                  15

Val Ala Gly Glu Ala Leu Xaa Lys
            20

<210> SEQ ID NO 33
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 33

Ile Lys Asn Asn Val Ala Gly Glu Ala Leu Leu Asp Lys Ile Ile Asn
```

```
1               5                   10                  15

Ala Ile Pro Tyr Leu Gly Xaa Lys
            20

<210> SEQ ID NO 34
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 34

Lys Ile Ile Asn Ala Ile Pro Tyr Leu Gly Asn Ser Tyr Ser Leu Leu
1               5                   10                  15

Asp Lys Phe Asp Thr Asn Xaa Lys
            20

<210> SEQ ID NO 35
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 35

Tyr Ser Leu Leu Asp Lys Phe Asp Thr Asn Ser Asn Ser Val Ser Phe
1               5                   10                  15

Asn Leu Leu Glu Gln Asp Xaa Lys
            20

<210> SEQ ID NO 36
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 36

Ser Val Ser Phe Asn Leu Leu Glu Gln Asp Pro Ser Gly Ala Thr Thr
1               5                   10                  15

Lys Ser Ala Met Leu Thr Xaa Lys
            20
```

```
<210> SEQ ID NO 37
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 37

Gly Ala Thr Thr Lys Ser Ala Met Leu Thr Asn Leu Ile Ile Phe Gly
1               5                   10                  15

Pro Gly Pro Val Leu Asn Xaa Lys
            20

<210> SEQ ID NO 38
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 38

Ile Ile Phe Gly Pro Gly Pro Val Leu Asn Lys Asn Glu Val Arg Gly
1               5                   10                  15

Ile Val Leu Arg Val Asp Xaa Lys
            20

<210> SEQ ID NO 39
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 39

Glu Val Arg Gly Ile Val Leu Arg Val Asp Asn Lys Asn Tyr Phe Pro
1               5                   10                  15

Cys Arg Asp Gly Phe Gly Xaa Lys
            20

<210> SEQ ID NO 40
<211> LENGTH: 24
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 40

Asn Tyr Phe Pro Cys Arg Asp Gly Phe Gly Ser Ile Met Gln Met Ala
1               5                   10                  15

Phe Cys Pro Glu Tyr Val Xaa Lys
            20

<210> SEQ ID NO 41
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 41

Met Gln Met Ala Phe Cys Pro Glu Tyr Val Pro Thr Phe Asp Asn Val
1               5                   10                  15

Ile Glu Asn Ile Thr Ser Xaa Lys
            20

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 42

Phe Asp Asn Val Ile Glu Asn Ile Thr Ser Leu Thr Ile Gly Lys Ser
1               5                   10                  15

Lys Tyr Phe Gln Asp Pro Xaa Lys
            20

<210> SEQ ID NO 43
<211> LENGTH: 24
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 43

Ile Gly Lys Ser Lys Tyr Phe Gln Asp Pro Ala Leu Leu Leu Met His
1               5                   10                  15

Glu Leu Ile His Val Leu Xaa Lys
            20

<210> SEQ ID NO 44
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 44

Leu Leu Met His Glu Leu Ile His Val Leu His Gly Leu Tyr Gly Met
1               5                   10                  15

Gln Val Ser Ser His Glu Xaa Lys
            20

<210> SEQ ID NO 45
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 45

Leu Tyr Gly Met Gln Val Ser Ser His Glu Ile Ile Pro Ser Lys Gln
1               5                   10                  15

Glu Ile Tyr Met Gln His Xaa Lys
            20

<210> SEQ ID NO 46
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
```

```
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 46

Pro Ser Lys Gln Glu Ile Tyr Met Gln His Thr Tyr Pro Ile Ser Ala
1               5                   10                  15

Glu Glu Leu Phe Thr Phe Xaa Lys
            20

<210> SEQ ID NO 47
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 47

Pro Ile Ser Ala Glu Glu Leu Phe Thr Phe Gly Gly Gln Asp Ala Asn
1               5                   10                  15

Leu Ile Ser Ile Asp Ile Xaa Lys
            20

<210> SEQ ID NO 48
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 48

Gln Asp Ala Asn Leu Ile Ser Ile Asp Ile Lys Asn Asp Leu Tyr Glu
1               5                   10                  15

Lys Thr Leu Asn Asp Tyr Xaa Lys
            20

<210> SEQ ID NO 49
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
```

<223> OTHER INFORMATION: Lys(biotin)-amide

<400> SEQUENCE: 49

Asp Leu Tyr Glu Lys Thr Leu Asn Asp Tyr Lys Ala Ile Ala Asn Lys
1               5                   10                  15

Leu Ser Gln Val Thr Ser Xaa Lys
            20

<210> SEQ ID NO 50
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 50

Ile Ala Asn Lys Leu Ser Gln Val Thr Ser Cys Asn Asp Pro Asn Ile
1               5                   10                  15

Asp Ile Asp Ser Tyr Lys Xaa Lys
            20

<210> SEQ ID NO 51
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 51

Asp Pro Asn Ile Asp Ile Asp Ser Tyr Lys Gln Ile Tyr Gln Gln Lys
1               5                   10                  15

Tyr Gln Phe Asp Lys Asp Xaa Lys
            20

<210> SEQ ID NO 52
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 52

```
Tyr Gln Gln Lys Tyr Gln Phe Asp Lys Asp Ser Asn Gly Gln Tyr Ile
1               5                   10                  15

Val Asn Glu Asp Lys Phe Xaa Lys
            20
```

<210> SEQ ID NO 53
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 53

```
Gly Gln Tyr Ile Val Asn Glu Asp Lys Phe Gln Ile Leu Tyr Asn Ser
1               5                   10                  15

Ile Met Tyr Gly Phe Thr Xaa Lys
            20
```

<210> SEQ ID NO 54
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 54

```
Leu Tyr Asn Ser Ile Met Tyr Gly Phe Thr Glu Ile Glu Leu Gly Lys
1               5                   10                  15

Lys Phe Asn Ile Lys Thr Xaa Lys
            20
```

<210> SEQ ID NO 55
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 55

```
Glu Leu Gly Lys Lys Phe Asn Ile Lys Thr Arg Leu Ser Tyr Phe Ser
1               5                   10                  15

Met Asn His Asp Pro Val Xaa Lys
```

```
<210> SEQ ID NO 56
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 56

Ser Tyr Phe Ser Met Asn His Asp Pro Val Lys Ile Pro Asn Leu Leu
1               5                   10                  15

Asp Asp Thr Ile Tyr Asn Xaa Lys
            20

<210> SEQ ID NO 57
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 57

Pro Asn Leu Leu Asp Asp Thr Ile Tyr Asn Asp Thr Glu Gly Phe Asn
1               5                   10                  15

Ile Glu Ser Lys Asp Leu Xaa Lys
            20

<210> SEQ ID NO 58
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 58

Glu Gly Phe Asn Ile Glu Ser Lys Asp Leu Lys Ser Glu Tyr Lys Gly
1               5                   10                  15

Gln Asn Met Arg Val Asn Xaa Lys
            20

<210> SEQ ID NO 59
```

```
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 59

Glu Tyr Lys Gly Gln Asn Met Arg Val Asn Thr Asn Ala Phe Arg Asn
1               5                   10                  15

Val Asp Gly Ser Gly Leu Xaa Lys
            20

<210> SEQ ID NO 60
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 60

Ala Phe Arg Asn Val Asp Gly Ser Gly Leu Val Ser Lys Leu Ile Gly
1               5                   10                  15

Leu Cys Lys Lys Ile Ile Xaa Lys
            20

<210> SEQ ID NO 61
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 61

Lys Leu Ile Gly Leu Cys Lys Lys Ile Ile Pro Pro Thr Asn Ile Arg
1               5                   10                  15

Glu Asn Leu Tyr Asn Arg Xaa Lys
            20

<210> SEQ ID NO 62
<211> LENGTH: 24
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 62

Ile Gly Leu Cys Lys Lys Ile Ile Pro Pro Thr Asn Ile Arg Glu Asn
 1               5                  10                  15

Leu Tyr Asn Arg Thr Ala Xaa Lys
                20

<210> SEQ ID NO 63
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 63

Ser Leu Thr Asp Leu Gly Gly Glu Leu Cys Ile Lys Ile Lys Asn Glu
 1               5                  10                  15

Asp Leu Thr Phe Ile Ala Xaa Lys
                20

<210> SEQ ID NO 64
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 64

Ile Lys Asn Glu Asp Leu Thr Phe Ile Ala Glu Lys Asn Ser Phe Ser
 1               5                  10                  15

Glu Glu Pro Phe Gln Asp Xaa Lys
                20

<210> SEQ ID NO 65
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 65

Asn Ser Phe Ser Glu Glu Pro Phe Gln Asp Glu Ile Val Ser Tyr Asn
1               5                   10                  15

Thr Lys Asn Lys Pro Leu Xaa Lys
            20

<210> SEQ ID NO 66
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 66

Val Ser Tyr Asn Thr Lys Asn Lys Pro Leu Asn Phe Asn Tyr Ser Leu
1               5                   10                  15

Asp Lys Ile Ile Val Asp Xaa Lys
            20

<210> SEQ ID NO 67
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 67

Asn Tyr Ser Leu Asp Lys Ile Ile Val Asp Tyr Asn Leu Gln Ser Lys
1               5                   10                  15

Ile Thr Leu Pro Asn Asp Xaa Lys
            20

<210> SEQ ID NO 68
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
```

-continued

<222> LOCATION: (24)..(24)
<223> OTHER INFORMATION: Lys(biotin)-amide

<400> SEQUENCE: 68

Leu Gln Ser Lys Ile Thr Leu Pro Asn Asp Arg Thr Thr Pro Val Thr
1               5                   10                  15

Lys Gly Ile Pro Tyr Ala Xaa Lys
            20

<210> SEQ ID NO 69
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 69

Thr Pro Val Thr Lys Gly Ile Pro Tyr Ala Pro Glu Tyr Lys Ser Asn
1               5                   10                  15

Ala Ala Ser Thr Ile Glu Xaa Lys
            20

<210> SEQ ID NO 70
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 70

Tyr Lys Ser Asn Ala Ala Ser Thr Ile Glu Ile His Asn Ile Asp Asp
1               5                   10                  15

Asn Thr Ile Tyr Gln Tyr Xaa Lys
            20

<210> SEQ ID NO 71
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 71

```
Asn Ile Asp Asp Asn Thr Ile Tyr Gln Tyr Leu Tyr Ala Gln Lys Ser
1               5                   10                  15

Pro Thr Thr Leu Gln Arg Xaa Lys
            20
```

<210> SEQ ID NO 72
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 72

```
Ala Gln Lys Ser Pro Thr Thr Leu Gln Arg Ile Thr Met Thr Asn Ser
1               5                   10                  15

Val Asp Asp Ala Leu Ile Xaa Lys
            20
```

<210> SEQ ID NO 73
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 73

```
Met Thr Asn Ser Val Asp Asp Ala Leu Ile Asn Ser Thr Lys Ile Tyr
1               5                   10                  15

Ser Tyr Phe Pro Ser Val Xaa Lys
            20
```

<210> SEQ ID NO 74
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 74

```
Thr Lys Ile Tyr Ser Tyr Phe Pro Ser Val Ile Ser Lys Val Asn Gln
1               5                   10                  15
```

Gly Ala Gln Gly Ile Leu Xaa Lys
            20

<210> SEQ ID NO 75
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 75

Lys Val Asn Gln Gly Ala Gln Gly Ile Leu Phe Leu Gln Trp Val Arg
1               5                   10                  15

Asp Ile Ile Asp Asp Phe Xaa Lys
            20

<210> SEQ ID NO 76
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 76

Gln Trp Val Arg Asp Ile Ile Asp Asp Phe Thr Asn Glu Ser Ser Gln
1               5                   10                  15

Lys Thr Thr Ile Asp Lys Xaa Lys
            20

<210> SEQ ID NO 77
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 77

Glu Ser Ser Gln Lys Thr Thr Ile Asp Lys Ile Ser Asp Val Ser Thr
1               5                   10                  15

Ile Val Pro Tyr Ile Gly Xaa Lys
            20

```
<210> SEQ ID NO 78
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 78

Asp Val Ser Thr Ile Val Pro Tyr Ile Gly Pro Ala Leu Asn Ile Val
1               5                   10                  15

Lys Gln Gly Tyr Glu Gly Xaa Lys
            20

<210> SEQ ID NO 79
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 79

Leu Asn Ile Val Lys Gln Gly Tyr Glu Gly Asn Phe Ile Gly Ala Leu
1               5                   10                  15

Glu Thr Thr Gly Val Val Xaa Lys
            20

<210> SEQ ID NO 80
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 80

Ile Gly Ala Leu Glu Thr Thr Gly Val Val Leu Leu Leu Glu Tyr Ile
1               5                   10                  15

Pro Glu Ile Thr Leu Pro Xaa Lys
            20

<210> SEQ ID NO 81
<211> LENGTH: 24
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 81

Leu Glu Tyr Ile Pro Glu Ile Thr Leu Pro Val Ile Ala Ala Leu Ser
1               5                   10                  15

Ile Ala Glu Ser Ser Thr Xaa Lys
            20

<210> SEQ ID NO 82
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 82

Ala Ala Leu Ser Ile Ala Glu Ser Ser Thr Gln Lys Glu Lys Ile Ile
1               5                   10                  15

Lys Thr Ile Asp Asn Phe Xaa Lys
            20

<210> SEQ ID NO 83
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 83

Glu Lys Ile Ile Lys Thr Ile Asp Asn Phe Leu Glu Lys Arg Tyr Glu
1               5                   10                  15

Lys Trp Ile Glu Val Tyr Xaa Lys
            20

<210> SEQ ID NO 84
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 84

Lys Arg Tyr Glu Lys Trp Ile Glu Val Tyr Lys Leu Val Lys Ala Lys
1               5                   10                  15

Trp Leu Gly Thr Val Asn Xaa Lys
            20

<210> SEQ ID NO 85
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 85

Val Lys Ala Lys Trp Leu Gly Thr Val Asn Thr Gln Phe Gln Lys Arg
1               5                   10                  15

Ser Tyr Gln Met Tyr Arg Xaa Lys
            20

<210> SEQ ID NO 86
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 86

Phe Gln Lys Arg Ser Tyr Gln Met Tyr Arg Ser Leu Glu Tyr Gln Val
1               5                   10                  15

Asp Ala Ile Lys Lys Ile Xaa Lys
            20

<210> SEQ ID NO 87
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
```

```
<221> NAME/KEY: MOD_RES
<222> LOCATION: (24)..(24)
<223> OTHER INFORMATION: Lys(biotin)-amide

<400> SEQUENCE: 87

Glu Tyr Gln Val Asp Ala Ile Lys Lys Ile Ile Asp Tyr Glu Tyr Lys
1               5                   10                  15

Ile Tyr Ser Gly Pro Asp Xaa Lys
            20

<210> SEQ ID NO 88
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 88

Tyr Glu Tyr Lys Ile Tyr Ser Gly Pro Asp Lys Glu Gln Ile Ala Asp
1               5                   10                  15

Glu Ile Asn Asn Leu Lys Xaa Lys
            20

<210> SEQ ID NO 89
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 89

Gln Ile Ala Asp Glu Ile Asn Asn Leu Lys Asn Lys Leu Glu Glu Lys
1               5                   10                  15

Ala Asn Lys Ala Met Ile Xaa Lys
            20

<210> SEQ ID NO 90
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide
```

```
<400> SEQUENCE: 90

Leu Glu Glu Lys Ala Asn Lys Ala Met Ile Asn Ile Asn Ile Phe Met
1               5                   10                  15

Arg Glu Ser Ser Arg Ser Xaa Lys
            20

<210> SEQ ID NO 91
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 91

Asn Ile Phe Met Arg Glu Ser Ser Arg Ser Phe Leu Val Asn Gln Met
1               5                   10                  15

Ile Asn Glu Ala Lys Lys Xaa Lys
            20

<210> SEQ ID NO 92
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 92

Val Asn Gln Met Ile Asn Glu Ala Lys Lys Gln Leu Leu Glu Phe Asp
1               5                   10                  15

Thr Gln Ser Lys Asn Ile Xaa Lys
            20

<210> SEQ ID NO 93
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 93

Leu Glu Phe Asp Thr Gln Ser Lys Asn Ile Leu Met Gln Tyr Ile Lys
1               5                   10                  15
```

```
Ala Asn Ser Lys Phe Ile Xaa Lys
            20

<210> SEQ ID NO 94
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 94

Gln Tyr Ile Lys Ala Asn Ser Lys Phe Ile Gly Ile Thr Glu Leu Lys
1               5                   10                  15

Lys Leu Glu Ser Lys Ile Xaa Lys
            20

<210> SEQ ID NO 95
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 95

Thr Glu Leu Lys Lys Leu Glu Ser Lys Ile Asn Lys Val Phe Ser Thr
1               5                   10                  15

Pro Ile Pro Phe Ser Tyr Xaa Lys
            20

<210> SEQ ID NO 96
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 96

Val Phe Ser Thr Pro Ile Pro Phe Ser Tyr Ser Lys Asn Leu Asp Cys
1               5                   10                  15

Trp Val Asp Asn Glu Glu Xaa Lys
            20
```

```
<210> SEQ ID NO 97
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 97

Asn Leu Asp Cys Trp Val Asp Asn Glu Glu Asp Ile Asp Val Ile Leu
1               5                   10                  15

Lys Lys Ser Thr Ile Leu Xaa Lys
            20

<210> SEQ ID NO 98
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 98

Asp Val Ile Leu Lys Lys Ser Thr Ile Leu Asn Leu Asp Ile Asn Asn
1               5                   10                  15

Asp Ile Ile Ser Asp Ile Xaa Lys
            20

<210> SEQ ID NO 99
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 99

Asp Ile Asn Asn Asp Ile Ile Ser Asp Ile Ser Gly Phe Asn Ser Ser
1               5                   10                  15

Val Ile Thr Tyr Pro Asp Xaa Lys
            20

<210> SEQ ID NO 100
<211> LENGTH: 24
<212> TYPE: PRT
```

<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 100

Phe Asn Ser Ser Val Ile Thr Tyr Pro Asp Ala Gln Leu Val Pro Gly
1               5                   10                  15

Ile Asn Gly Lys Ala Ile Xaa Lys
            20

<210> SEQ ID NO 101
<211> LENGTH: 24
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 101

Leu Val Pro Gly Ile Asn Gly Lys Ala Ile His Leu Val Asn Asn Glu
1               5                   10                  15

Ser Ser Glu Val Ile Val Xaa Lys
            20

<210> SEQ ID NO 102
<211> LENGTH: 24
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 102

Val Asn Asn Glu Ser Ser Glu Val Ile Val His Lys Ala Met Asp Ile
1               5                   10                  15

Glu Tyr Asn Asp Met Phe Xaa Lys
            20

<210> SEQ ID NO 103
<211> LENGTH: 24
<212> TYPE: PRT
<213> ORGANISM: Artificial Sequence
<220> FEATURE:
<223> OTHER INFORMATION: Description of Artificial Sequence: Synthetic
    peptide

```
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 103

Ala Met Asp Ile Glu Tyr Asn Asp Met Phe Asn Asn Phe Thr Val Ser
1               5                   10                  15

Phe Trp Leu Arg Val Pro Xaa Lys
            20

<210> SEQ ID NO 104
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 104

Phe Thr Val Ser Phe Trp Leu Arg Val Pro Lys Val Ser Ala Ser His
1               5                   10                  15

Leu Glu Gln Tyr Gly Thr Xaa Lys
            20

<210> SEQ ID NO 105
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 105

Ser Ala Ser His Leu Glu Gln Tyr Gly Thr Asn Glu Tyr Ser Ile Ile
1               5                   10                  15

Ser Ser Met Lys Lys His Xaa Lys
            20

<210> SEQ ID NO 106
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
```

```
<220> FEATURE:
<221> NAME/KEY: MOD_RES
<222> LOCATION: (24)..(24)
<223> OTHER INFORMATION: Lys(biotin)-amide

<400> SEQUENCE: 106

Tyr Ser Ile Ile Ser Ser Met Lys Lys His Ser Leu Ser Ile Gly Ser
1               5                   10                  15

Gly Trp Ser Val Ser Leu Xaa Lys
            20

<210> SEQ ID NO 107
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 107

Ser Ile Gly Ser Gly Trp Ser Val Ser Leu Lys Gly Asn Asn Leu Ile
1               5                   10                  15

Trp Thr Leu Lys Asp Ser Xaa Lys
            20

<210> SEQ ID NO 108
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 108

Asn Asn Leu Ile Trp Thr Leu Lys Asp Ser Ala Gly Glu Val Arg Gln
1               5                   10                  15

Ile Thr Phe Arg Asp Leu Xaa Lys
            20

<210> SEQ ID NO 109
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide
```

<400> SEQUENCE: 109

Glu Val Arg Gln Ile Thr Phe Arg Asp Leu Pro Asp Lys Phe Asn Ala
1               5                   10                  15

Tyr Leu Ala Asn Lys Trp Xaa Lys
            20

<210> SEQ ID NO 110
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 110

Lys Phe Asn Ala Tyr Leu Ala Asn Lys Trp Val Phe Ile Thr Ile Thr
1               5                   10                  15

Asn Asp Arg Leu Ser Ser Xaa Lys
            20

<210> SEQ ID NO 111
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 111

Ile Thr Ile Thr Asn Asp Arg Leu Ser Ser Ala Asn Leu Tyr Ile Asn
1               5                   10                  15

Gly Val Leu Met Gly Ser Xaa Lys
            20

<210> SEQ ID NO 112
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 112

Leu Tyr Ile Asn Gly Val Leu Met Gly Ser Ala Glu Ile Thr Gly Leu

```
1               5                   10                  15

Gly Ala Ile Arg Glu Asp Xaa Lys
            20

<210> SEQ ID NO 113
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 113

Ile Thr Gly Leu Gly Ala Ile Arg Glu Asp Asn Asn Ile Thr Leu Lys
1               5                   10                  15

Leu Asp Arg Cys Asn Asn Xaa Lys
            20

<210> SEQ ID NO 114
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 114

Ile Thr Leu Lys Leu Asp Arg Cys Asn Asn Asn Gln Tyr Val Ser
1               5                   10                  15

Ile Asp Lys Phe Arg Ile Xaa Lys
            20

<210> SEQ ID NO 115
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 115

Gln Tyr Val Ser Ile Asp Lys Phe Arg Ile Phe Cys Lys Ala Leu Asn
1               5                   10                  15

Pro Lys Glu Ile Glu Lys Xaa Lys
            20
```

```
<210> SEQ ID NO 116
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 116

Lys Ala Leu Asn Pro Lys Glu Ile Glu Lys Leu Tyr Thr Ser Tyr Leu
1               5                   10                  15

Ser Ile Thr Phe Leu Arg Xaa Lys
            20

<210> SEQ ID NO 117
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 117

Thr Ser Tyr Leu Ser Ile Thr Phe Leu Arg Asp Phe Trp Gly Asn Pro
1               5                   10                  15

Leu Arg Tyr Asp Thr Glu Xaa Lys
            20

<210> SEQ ID NO 118
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 118

Trp Gly Asn Pro Leu Arg Tyr Asp Thr Glu Tyr Tyr Leu Ile Pro Val
1               5                   10                  15

Ala Ser Ser Ser Lys Asp Xaa Lys
            20

<210> SEQ ID NO 119
<211> LENGTH: 24
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 119

Leu Ile Pro Val Ala Ser Ser Ser Lys Asp Val Gln Leu Lys Asn Ile
1               5                   10                  15

Thr Asp Tyr Met Tyr Leu Xaa Lys
            20

<210> SEQ ID NO 120
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 120

Leu Lys Asn Ile Thr Asp Tyr Met Tyr Leu Thr Asn Ala Pro Ser Tyr
1               5                   10                  15

Thr Asn Gly Lys Leu Asn Xaa Lys
            20

<210> SEQ ID NO 121
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 121

Ala Pro Ser Tyr Thr Asn Gly Lys Leu Asn Ile Tyr Tyr Arg Arg Leu
1               5                   10                  15

Tyr Asn Gly Leu Lys Phe Xaa Lys
            20

<210> SEQ ID NO 122
<211> LENGTH: 24
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 122

Tyr Arg Arg Leu Tyr Asn Gly Leu Lys Phe Ile Ile Lys Arg Tyr Thr
1               5                   10                  15

Pro Asn Asn Glu Ile Asp Xaa Lys
            20

<210> SEQ ID NO 123
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 123

Lys Arg Tyr Thr Pro Asn Asn Glu Ile Asp Ser Phe Val Lys Ser Gly
1               5                   10                  15

Asp Phe Ile Lys Leu Tyr Xaa Lys
            20

<210> SEQ ID NO 124
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 124

Val Lys Ser Gly Asp Phe Ile Lys Leu Tyr Val Ser Tyr Asn Asn Asn
1               5                   10                  15

Glu His Ile Val Gly Tyr Xaa Lys
            20

<210> SEQ ID NO 125
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
```

```
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 125

Tyr Asn Asn Asn Glu His Ile Val Gly Tyr Pro Lys Asp Gly Asn Ala
1               5                   10                  15

Phe Asn Asn Leu Asp Arg Xaa Lys
            20

<210> SEQ ID NO 126
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 126

Asp Gly Asn Ala Phe Asn Asn Leu Asp Arg Ile Leu Arg Val Gly Tyr
1               5                   10                  15

Asn Ala Pro Gly Ile Pro Xaa Lys
            20

<210> SEQ ID NO 127
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 127

Arg Val Gly Tyr Asn Ala Pro Gly Ile Pro Leu Tyr Lys Lys Met Glu
1               5                   10                  15

Ala Val Lys Leu Arg Asp Xaa Lys
            20

<210> SEQ ID NO 128
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
```

<223> OTHER INFORMATION: Lys(biotin)-amide

<400> SEQUENCE: 128

Lys Lys Met Glu Ala Val Lys Leu Arg Asp Leu Lys Thr Tyr Ser Val
1               5                   10                  15

Gln Leu Lys Leu Tyr Asp Xaa Lys
            20

<210> SEQ ID NO 129
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 129

Thr Tyr Ser Val Gln Leu Lys Leu Tyr Asp Asp Lys Asn Ala Ser Leu
1               5                   10                  15

Gly Leu Val Gly Thr His Xaa Lys
            20

<210> SEQ ID NO 130
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 130

Asn Ala Ser Leu Gly Leu Val Gly Thr His Asn Gly Gln Ile Gly Asn
1               5                   10                  15

Asp Pro Asn Arg Asp Ile Xaa Lys
            20

<210> SEQ ID NO 131
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 131

```
Gln Ile Gly Asn Asp Pro Asn Arg Asp Ile Leu Ile Ala Ser Asn Trp
1               5                   10                  15

Tyr Phe Asn His Leu Lys Xaa Lys
                20
```

<210> SEQ ID NO 132
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 132

```
Ala Ser Asn Trp Tyr Phe Asn His Leu Lys Asp Lys Ile Leu Gly Cys
1               5                   10                  15

Asp Trp Tyr Phe Val Pro Xaa Lys
                20
```

<210> SEQ ID NO 133
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys(biotin)-amide

<400> SEQUENCE: 133

```
Leu Lys Asp Lys Ile Leu Gly Cys Asp Trp Tyr Phe Val Pro Thr Asp
1               5                   10                  15

Glu Gly Trp Thr Asn Asp Xaa Lys
                20
```

<210> SEQ ID NO 134
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

```
Ile Lys Ala Asn Ser Lys Phe Ile Gly Ile Thr Glu Leu Lys
1               5                   10
```

<210> SEQ ID NO 135
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 135

Ala Asn Ser Lys Phe Ile Gly Ile Thr Glu Leu Lys
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ile Lys Ala Asn Ser Lys Phe Ile Gly Ile Thr Glu
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gln Tyr Ile Lys Ala Asn Ser Lys Phe Ile Gly Ile
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Thr Glu Leu Lys Lys Leu Glu Ser Lys Ile
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ser Lys Phe Ile Gly Ile Thr Glu Leu Lys
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Asn Ser Lys Phe Ile Gly Ile Thr Glu
1               5                   10

<210> SEQ ID NO 141
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 141

Ile Lys Ala Asn Ser Lys Phe Ile Gly Ile
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gln Tyr Ile Lys Ala Asn Ser Lys Phe Ile
1               5                   10

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Leu Lys Lys Leu Glu Ser Lys Ile
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Thr Glu Leu Lys Lys Leu Glu Ser
1               5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Ile Thr Glu Leu Lys Lys Leu
1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Phe Ile Gly Ile Thr Glu Leu Lys
1               5
```

```
<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ser Lys Phe Ile Gly Ile Thr Glu
1               5

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ala Asn Ser Lys Phe Ile Gly Ile
1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ile Lys Ala Asn Ser Lys Phe Ile
1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gln Tyr Ile Lys Ala Asn Ser Lys
1               5

<210> SEQ ID NO 151
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Aminohexanoic acid
<220> FEATURE:
<221> NAME/KEY: MOD_RES
<222> LOCATION: (22)..(22)
<223> OTHER INFORMATION: Lys(biotin)-amide

<400> SEQUENCE: 151

Phe Ile Gly Ile Thr Glu Leu Lys Lys Leu Glu Ser Lys Ile Asn Lys
1               5                   10                  15
```

```
Val Phe Ser Thr Xaa Lys
            20

<210> SEQ ID NO 152
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Aminohexanoic acid
<220> FEATURE:
<221> NAME/KEY: MOD_RES
<222> LOCATION: (21)..(21)
<223> OTHER INFORMATION: Lys(biotin)-amide

<400> SEQUENCE: 152

Phe Ile Gly Ile Thr Glu Leu Lys Lys Leu Glu Ser Lys Ile Asn Lys
1               5                   10                  15

Val Phe Ser Xaa Lys
            20

<210> SEQ ID NO 153
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys(biotin)-amide

<400> SEQUENCE: 153

Phe Ile Gly Ile Thr Glu Leu Lys Lys Leu Glu Ser Lys Ile Asn Lys
1               5                   10                  15

Val Phe Xaa Lys
            20

<210> SEQ ID NO 154
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Aminohexanoic acid
<220> FEATURE:
<221> NAME/KEY: MOD_RES
<222> LOCATION: (19)..(19)
<223> OTHER INFORMATION: Lys(biotin)-amide

<400> SEQUENCE: 154

Phe Ile Gly Ile Thr Glu Leu Lys Lys Leu Glu Ser Lys Ile Asn Lys
1               5                   10                  15

Val Xaa Lys

<210> SEQ ID NO 155
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Aminohexanoic acid
<220> FEATURE:
<221> NAME/KEY: MOD_RES
<222> LOCATION: (18)..(18)
<223> OTHER INFORMATION: Lys(biotin)-amide

<400> SEQUENCE: 155

Phe Ile Gly Ile Thr Glu Leu Lys Lys Leu Glu Ser Lys Ile Asn Lys
1               5                   10                  15

Xaa Lys

<210> SEQ ID NO 156
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Aminohexanoic acid
<220> FEATURE:
<221> NAME/KEY: MOD_RES
<222> LOCATION: (17)..(17)
<223> OTHER INFORMATION: Lys(biotin)-amide

<400> SEQUENCE: 156

Phe Ile Gly Ile Thr Glu Leu Lys Lys Leu Glu Ser Lys Ile Asn Xaa
1               5                   10                  15

Lys

<210> SEQ ID NO 157
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys(biotin)-amide

<400> SEQUENCE: 157

Ile Gly Ile Thr Glu Leu Lys Lys Leu Glu Ser Lys Ile Asn Xaa Lys
1               5                   10                  15

<210> SEQ ID NO 158
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
```

<223> OTHER INFORMATION: Aminohexanoic acid
<220> FEATURE:
<221> NAME/KEY: MOD_RES
<222> LOCATION: (16)..(16)
<223> OTHER INFORMATION: Lys(biotin)-amide

<400> SEQUENCE: 158

Gly Ile Thr Glu Leu Lys Lys Leu Glu Ser Lys Ile Asn Lys Xaa Lys
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys(biotin)-amide

<400> SEQUENCE: 159

Ile Thr Glu Leu Lys Lys Leu Glu Ser Lys Ile Asn Lys Val Xaa Lys
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys(biotin)-amide

<400> SEQUENCE: 160

Thr Glu Leu Lys Lys Leu Glu Ser Lys Ile Asn Lys Val Phe Xaa Lys
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys(biotin)-amide

<400> SEQUENCE: 161

Glu Leu Lys Lys Leu Glu Ser Lys Ile Asn Lys Val Phe Ser Xaa Lys
1               5                   10                  15

<210> SEQ ID NO 162

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys(biotin)-amide

<400> SEQUENCE: 162

Leu Lys Lys Leu Glu Ser Lys Ile Asn Lys Val Phe Ser Thr Xaa Lys
1               5                   10                  15

<210> SEQ ID NO 163
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys(formyl)
<220> FEATURE:
<221> NAME/KEY: MOD_RES
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys(biotin)-amide

<400> SEQUENCE: 163

Phe Ile Gly Ile Thr Glu Leu Lys Lys Leu Glu Ser Lys Ile Xaa Lys
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Lys(formyl)
<220> FEATURE:
<221> NAME/KEY: MOD_RES
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys(biotin)-amide

<400> SEQUENCE: 164

Phe Ile Gly Ile Thr Glu Leu Lys Lys Leu Glu Ser Lys Ile Xaa Lys
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MOD_RES
<222> LOCATION: (13)..(13)
<223> OTHER INFORMATION: Lys(formyl)
<220> FEATURE:
<221> NAME/KEY: MOD_RES
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys(biotin)-amide

<400> SEQUENCE: 165

Phe Ile Gly Ile Thr Glu Leu Lys Lys Leu Glu Ser Lys Ile Xaa Lys
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: Lys(formyl)
<220> FEATURE:
<221> NAME/KEY: MOD_RES
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys(biotin)-amide

<400> SEQUENCE: 166

Phe Ile Gly Ile Thr Glu Leu Lys Lys Leu Glu Ser Lys Ile Xaa Lys
1               5                   10                  15

<210> SEQ ID NO 167
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys(formyl)
<220> FEATURE:
<221> NAME/KEY: MOD_RES
<222> LOCATION: (13)..(13)
<223> OTHER INFORMATION: Lys(formyl)
<220> FEATURE:
<221> NAME/KEY: MOD_RES
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys(biotin)-amide

<400> SEQUENCE: 167

Phe Ile Gly Ile Thr Glu Leu Lys Lys Leu Glu Ser Lys Ile Xaa Lys
1               5                   10                  15

<210> SEQ ID NO 168
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Lys(formyl)
<220> FEATURE:
<221> NAME/KEY: MOD_RES
<222> LOCATION: (13)..(13)
<223> OTHER INFORMATION: Lys(formyl)
<220> FEATURE:
<221> NAME/KEY: MOD_RES
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys(biotin)-amide

<400> SEQUENCE: 168

Phe Ile Gly Ile Thr Glu Leu Lys Lys Leu Glu Ser Lys Ile Xaa Lys
1               5                   10                  15

<210> SEQ ID NO 169
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: Lys(formyl)
<220> FEATURE:
<221> NAME/KEY: MOD_RES
<222> LOCATION: (13)..(13)
<223> OTHER INFORMATION: Lys(formyl)
<220> FEATURE:
<221> NAME/KEY: MOD_RES
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys(biotin)-amide

<400> SEQUENCE: 169

Phe Ile Gly Ile Thr Glu Leu Lys Lys Leu Glu Ser Lys Ile Xaa Lys
1               5                   10                  15

<210> SEQ ID NO 170
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin
<220> FEATURE:
<221> NAME/KEY: MOD_RES
<222> LOCATION: (1)..(2)
<223> OTHER INFORMATION: Aminohexanoic acid

<400> SEQUENCE: 170

Xaa Xaa Ser Lys Phe Ile Gly Ile Thr Glu Leu Lys Lys Leu Glu Ser
1               5                   10                  15

Lys Ile Asn Lys Val Phe
            20
```

```
<210> SEQ ID NO 171
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin
<220> FEATURE:
<221> NAME/KEY: MOD_RES
<222> LOCATION: (1)..(2)
<223> OTHER INFORMATION: Aminohexanoic acid

<400> SEQUENCE: 171

Xaa Xaa Phe Ile Gly Ile Thr Glu Leu Lys Lys Leu Glu Ser Lys Ile
1               5                   10                  15

Asn Lys Val Phe
            20

<210> SEQ ID NO 172
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(20)
<223> OTHER INFORMATION: Aminohexanoic acid
<220> FEATURE:
<221> NAME/KEY: MOD_RES
<222> LOCATION: (21)..(21)
<223> OTHER INFORMATION: Lys-biotin

<400> SEQUENCE: 172

Phe Ile Gly Ile Thr Glu Leu Lys Lys Leu Glu Ser Lys Ile Asn Lys
1               5                   10                  15

Val Phe Xaa Xaa Lys
            20

<210> SEQ ID NO 173
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 173

Phe Ile Gly Ile Thr Glu Leu Lys Lys Leu Glu Ser Lys Ile Asn Lys
1               5                   10                  15

Val Xaa Xaa Lys
            20

<210> SEQ ID NO 174
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (17)..(18)
<223> OTHER INFORMATION: Aminohexanoic acid
<220> FEATURE:
<221> NAME/KEY: MOD_RES
<222> LOCATION: (19)..(19)
<223> OTHER INFORMATION: Lys-biotin

<400> SEQUENCE: 174

Phe Ile Gly Ile Thr Glu Leu Lys Lys Leu Glu Ser Lys Ile Asn Lys
1               5                   10                  15

Xaa Xaa Lys

<210> SEQ ID NO 175
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(17)
<223> OTHER INFORMATION: Aminohexanoic acid
<220> FEATURE:
<221> NAME/KEY: MOD_RES
<222> LOCATION: (18)..(18)
<223> OTHER INFORMATION: Lys-biotin

<400> SEQUENCE: 175

Phe Ile Gly Ile Thr Glu Leu Lys Lys Leu Glu Ser Lys Ile Asn Xaa
1               5                   10                  15

Xaa Lys

<210> SEQ ID NO 176
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(16)
<223> OTHER INFORMATION: Aminohexanoic acid
<220> FEATURE:
<221> NAME/KEY: MOD_RES
<222> LOCATION: (17)..(17)
<223> OTHER INFORMATION: Lys-biotin

<400> SEQUENCE: 176

Phe Ile Gly Ile Thr Glu Leu Lys Lys Leu Glu Ser Lys Ile Xaa Xaa
1               5                   10                  15

Lys

<210> SEQ ID NO 177
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
```

-continued

```
<221> NAME/KEY: MOD_RES
<222> LOCATION: (24)..(24)
<223> OTHER INFORMATION: Lys-biotin

<400> SEQUENCE: 177

Gln Tyr Ile Lys Ala Asn Ser Lys Phe Ile Gly Ile Thr Glu Leu Lys
1               5                   10                  15

Lys Leu Glu Ser Lys Ile Xaa Lys
            20

<210> SEQ ID NO 178
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys-biotin

<400> SEQUENCE: 178

Ser Leu Thr Asp Leu Gly Gly Glu Leu Cys Ile Lys Ile Lys Asn Glu
1               5                   10                  15

Asp Leu Thr Phe Ile Ala Xaa Lys
            20

<210> SEQ ID NO 179
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 179

Phe Ile Gly Ile Thr Glu Leu Lys Lys Leu Glu Ser Lys Ile Asn Lys
1               5                   10                  15

Val Phe Xaa Lys
            20

<210> SEQ ID NO 180
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin
```

-continued

```
<400> SEQUENCE: 180

Ala Ile Gly Ile Thr Glu Leu Lys Lys Leu Glu Ser Lys Ile Asn Lys
1               5                   10                  15

Val Phe Xaa Lys
            20

<210> SEQ ID NO 181
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 181

Phe Ala Gly Ile Thr Glu Leu Lys Lys Leu Glu Ser Lys Ile Asn Lys
1               5                   10                  15

Val Phe Xaa Lys
            20

<210> SEQ ID NO 182
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 182

Phe Ile Ala Ile Thr Glu Leu Lys Lys Leu Glu Ser Lys Ile Asn Lys
1               5                   10                  15

Val Phe Xaa Lys
            20

<210> SEQ ID NO 183
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 183

Phe Ile Gly Ala Thr Glu Leu Lys Lys Leu Glu Ser Lys Ile Asn Lys
1               5                   10                  15
```

```
Val Phe Xaa Lys
            20

<210> SEQ ID NO 184
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 184

Phe Ile Gly Ile Ala Glu Leu Lys Lys Leu Glu Ser Lys Ile Asn Lys
1               5                   10                  15

Val Phe Xaa Lys
            20

<210> SEQ ID NO 185
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 185

Phe Ile Gly Ile Thr Ala Leu Lys Lys Leu Glu Ser Lys Ile Asn Lys
1               5                   10                  15

Val Phe Xaa Lys
            20

<210> SEQ ID NO 186
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 186

Phe Ile Gly Ile Thr Glu Ala Lys Lys Leu Glu Ser Lys Ile Asn Lys
1               5                   10                  15

Val Phe Xaa Lys
            20
```

```
<210> SEQ ID NO 187
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 187

Phe Ile Gly Ile Thr Glu Leu Ala Lys Leu Glu Ser Lys Ile Asn Lys
1               5                   10                  15

Val Phe Xaa Lys
            20

<210> SEQ ID NO 188
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 188

Phe Ile Gly Ile Thr Glu Leu Lys Ala Leu Glu Ser Lys Ile Asn Lys
1               5                   10                  15

Val Phe Xaa Lys
            20

<210> SEQ ID NO 189
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 189

Phe Ile Gly Ile Thr Glu Leu Lys Lys Ala Glu Ser Lys Ile Asn Lys
1               5                   10                  15

Val Phe Xaa Lys
            20

<210> SEQ ID NO 190
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 190

Phe Ile Gly Ile Thr Glu Leu Lys Lys Leu Ala Ser Lys Ile Asn Lys
1               5                   10                  15

Val Phe Xaa Lys
            20

<210> SEQ ID NO 191
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 191

Phe Ile Gly Ile Thr Glu Leu Lys Lys Leu Glu Ala Lys Ile Asn Lys
1               5                   10                  15

Val Phe Xaa Lys
            20

<210> SEQ ID NO 192
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 192

Phe Ile Gly Ile Thr Glu Leu Lys Lys Leu Glu Ser Ala Ile Asn Lys
1               5                   10                  15

Val Phe Xaa Lys
            20

<210> SEQ ID NO 193
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 193

Phe Ile Gly Ile Thr Glu Leu Lys Lys Leu Glu Ser Lys Ala Asn Lys
1               5                   10                  15
Val Phe Xaa Lys
            20

<210> SEQ ID NO 194
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 194

Phe Ile Gly Ile Thr Glu Leu Lys Lys Leu Glu Ser Lys Ile Ala Lys
1               5                   10                  15
Val Phe Xaa Lys
            20

<210> SEQ ID NO 195
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 195

Phe Ile Gly Ile Thr Glu Leu Lys Lys Leu Glu Ser Lys Ile Asn Ala
1               5                   10                  15
Val Phe Xaa Lys
            20

<210> SEQ ID NO 196
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
```

```
<220> FEATURE:
<221> NAME/KEY: MOD_RES
<222> LOCATION: (20)..(20)
<223> OTHER INFORMATION: Lys-biotin

<400> SEQUENCE: 196

Phe Ile Gly Ile Thr Glu Leu Lys Lys Leu Glu Ser Lys Ile Asn Lys
1               5                   10                  15

Ala Phe Xaa Lys
            20

<210> SEQ ID NO 197
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 197

Phe Ile Gly Ile Thr Glu Leu Lys Lys Leu Glu Ser Lys Ile Asn Lys
1               5                   10                  15

Val Ala Xaa Lys
            20

<210> SEQ ID NO 198
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 198

Phe Ile Gly Ile Thr Glu Leu Lys Lys Leu Glu Ser Lys Ile Asn Lys
1               5                   10                  15

Val Phe Xaa Lys
            20

<210> SEQ ID NO 199
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin
```

<400> SEQUENCE: 199

Tyr Ile Gly Ile Thr Glu Leu Lys Lys Leu Glu Ser Lys Ile Asn Lys
1               5                   10                  15

Val Phe Xaa Lys
            20

<210> SEQ ID NO 200
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 200

Phe Leu Gly Ile Thr Glu Leu Lys Lys Leu Glu Ser Lys Ile Asn Lys
1               5                   10                  15

Val Phe Xaa Lys
            20

<210> SEQ ID NO 201
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 201

Phe Ile Ser Ile Thr Glu Leu Lys Lys Leu Glu Ser Lys Ile Asn Lys
1               5                   10                  15

Val Phe Xaa Lys
            20

<210> SEQ ID NO 202
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 202

Phe Ile Gly Leu Thr Glu Leu Lys Lys Leu Glu Ser Lys Ile Asn Lys

```
1               5                   10                  15
Val Phe Xaa Lys
            20

<210> SEQ ID NO 203
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 203

Phe Ile Gly Ile Ser Glu Leu Lys Lys Leu Glu Ser Lys Ile Asn Lys
1               5                   10                  15

Val Phe Xaa Lys
            20

<210> SEQ ID NO 204
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 204

Phe Ile Gly Ile Thr Asp Leu Lys Lys Leu Glu Ser Lys Ile Asn Lys
1               5                   10                  15

Val Phe Xaa Lys
            20

<210> SEQ ID NO 205
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 205

Phe Ile Gly Ile Thr Glu Ile Lys Lys Leu Glu Ser Lys Ile Asn Lys
1               5                   10                  15

Val Phe Xaa Lys
            20
```

<210> SEQ ID NO 206
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 206

Phe Ile Gly Ile Thr Glu Leu Arg Lys Leu Glu Ser Lys Ile Asn Lys
1               5                   10                  15

Val Phe Xaa Lys
            20

<210> SEQ ID NO 207
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 207

Phe Ile Gly Ile Thr Glu Leu Lys Arg Leu Glu Ser Lys Ile Asn Lys
1               5                   10                  15

Val Phe Xaa Lys
            20

<210> SEQ ID NO 208
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 208

Phe Ile Gly Ile Thr Glu Leu Lys Lys Ile Glu Ser Lys Ile Asn Lys
1               5                   10                  15

Val Phe Xaa Lys
            20

<210> SEQ ID NO 209
<211> LENGTH: 20

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 209

Phe Ile Gly Ile Thr Glu Leu Lys Lys Leu Asp Ser Lys Ile Asn Lys
1               5                   10                  15
Val Phe Xaa Lys
            20

<210> SEQ ID NO 210
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 210

Phe Ile Gly Ile Thr Glu Leu Lys Lys Leu Glu Thr Lys Ile Asn Lys
1               5                   10                  15
Val Phe Xaa Lys
            20

<210> SEQ ID NO 211
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 211

Phe Ile Gly Ile Thr Glu Leu Lys Lys Leu Glu Ser Arg Ile Asn Lys
1               5                   10                  15
Val Phe Xaa Lys
            20

<210> SEQ ID NO 212
<211> LENGTH: 20
<212> TYPE: PRT
<213> ORGANISM: Artificial Sequence
<220> FEATURE:
<223> OTHER INFORMATION: Description of Artificial Sequence: Synthetic
```

```
                    peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 212

Phe Ile Gly Ile Thr Glu Leu Lys Lys Leu Glu Ser Lys Leu Asn Lys
1               5                   10                  15

Val Phe Xaa Lys
            20

<210> SEQ ID NO 213
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 213

Phe Ile Gly Ile Thr Glu Leu Lys Lys Leu Glu Ser Lys Ile Gln Lys
1               5                   10                  15

Val Phe Xaa Lys
            20

<210> SEQ ID NO 214
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 214

Phe Ile Gly Ile Thr Glu Leu Lys Lys Leu Glu Ser Lys Ile Asn Arg
1               5                   10                  15

Val Phe Xaa Lys
            20

<210> SEQ ID NO 215
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
```

```
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 215

Phe Ile Gly Ile Thr Glu Leu Lys Lys Leu Glu Ser Lys Ile Asn Lys
1               5                   10                  15

Leu Phe Xaa Lys
            20

<210> SEQ ID NO 216
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 216

Phe Ile Gly Ile Thr Glu Leu Lys Lys Leu Glu Ser Lys Ile Asn Lys
1               5                   10                  15

Val Tyr Xaa Lys
            20

<210> SEQ ID NO 217
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Phe Ile Gly Ile Thr Glu Leu Lys Lys Leu Glu Ser Lys Ile Asn Lys
1               5                   10                  15

Val Phe Ala Ala Lys Tyr Ala Arg Val Arg Ala Lys Cys
            20                  25

<210> SEQ ID NO 218
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Azidohexanoyl group

<400> SEQUENCE: 218

Leu Glu Gln Leu Glu Ser Ile Ile Asn Phe Glu Lys Leu Ala Ala Ala
1               5                   10                  15

Ala Ala Lys

<210> SEQ ID NO 219
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 219

Ser Ile Ile Asn Phe Glu Lys Leu
1               5

<210> SEQ ID NO 220
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gly Ile Thr Glu Leu
1               5

<210> SEQ ID NO 221
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gly Ile Thr Glu
1

<210> SEQ ID NO 222
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Phe Ile Gly Ile Thr
1               5

<210> SEQ ID NO 223
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aminohexanoic acid
<220> FEATURE:
<221> NAME/KEY: MOD_RES
<222> LOCATION: (24)..(24)
<223> OTHER INFORMATION: Lys-biotin

<400> SEQUENCE: 223

Gln Tyr Ile Lys Ala Asn Ser Lys Phe Ile Gly Ile Thr Glu Leu Lys
1               5                   10                  15

Lys Leu Glu Ser Lys Ile Xaa Lys
            20

<210> SEQ ID NO 224
<211> LENGTH: 22
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Aminohexanoic acid
<220> FEATURE:
<221> NAME/KEY: MOD_RES
<222> LOCATION: (22)..(22)
<223> OTHER INFORMATION: Lys-biotin

<400> SEQUENCE: 224

Ile Lys Ala Asn Ser Lys Phe Ile Gly Ile Thr Glu Leu Lys Lys Leu
1               5                   10                  15

Glu Ser Lys Ile Xaa Lys
                20

<210> SEQ ID NO 225
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Aminohexanoic acid
<220> FEATURE:
<221> NAME/KEY: MOD_RES
<222> LOCATION: (22)..(22)
<223> OTHER INFORMATION: Lys-biotin

<400> SEQUENCE: 225

Gln Tyr Ile Lys Ala Asn Ser Lys Phe Ile Gly Ile Thr Glu Leu Lys
1               5                   10                  15

Lys Leu Glu Ser Xaa Lys
                20

<210> SEQ ID NO 226
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 226

Ala Asn Ser Lys Phe Ile Gly Ile Thr Glu Leu Lys Lys Leu Glu Ser
1               5                   10                  15

Lys Ile Xaa Lys
            20

<210> SEQ ID NO 227
<211> LENGTH: 20
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 227

Ile Lys Ala Asn Ser Lys Phe Ile Gly Ile Thr Glu Leu Lys Lys Leu
1               5                   10                  15

Glu Ser Xaa Lys
            20

<210> SEQ ID NO 228
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Aminohexanoic acid
<220> FEATURE:
<221> NAME/KEY: MOD_RES
<222> LOCATION: (20)..(20)
<223> OTHER INFORMATION: Lys-biotin

<400> SEQUENCE: 228

Gln Tyr Ile Lys Ala Asn Ser Lys Phe Ile Gly Ile Thr Glu Leu Lys
1               5                   10                  15

Lys Leu Xaa Lys
            20

<210> SEQ ID NO 229
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Aminohexanoic acid
<220> FEATURE:
<221> NAME/KEY: MOD_RES
<222> LOCATION: (18)..(18)
<223> OTHER INFORMATION: Lys-biotin

<400> SEQUENCE: 229

Ser Lys Phe Ile Gly Ile Thr Glu Leu Lys Lys Leu Glu Ser Lys Ile
1               5                   10                  15

Xaa Lys

<210> SEQ ID NO 230
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Aminohexanoic acid
```

```
<220> FEATURE:
<221> NAME/KEY: MOD_RES
<222> LOCATION: (18)..(18)
<223> OTHER INFORMATION: Lys-biotin

<400> SEQUENCE: 230

Ala Asn Ser Lys Phe Ile Gly Ile Thr Glu Leu Lys Lys Leu Glu Ser
1               5                   10                  15

Xaa Lys

<210> SEQ ID NO 231
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Aminohexanoic acid
<220> FEATURE:
<221> NAME/KEY: MOD_RES
<222> LOCATION: (18)..(18)
<223> OTHER INFORMATION: Lys-biotin

<400> SEQUENCE: 231

Ile Lys Ala Asn Ser Lys Phe Ile Gly Ile Thr Glu Leu Lys Lys Leu
1               5                   10                  15

Xaa Lys

<210> SEQ ID NO 232
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Aminohexanoic acid
<220> FEATURE:
<221> NAME/KEY: MOD_RES
<222> LOCATION: (18)..(18)
<223> OTHER INFORMATION: Lys-biotin

<400> SEQUENCE: 232

Gln Tyr Ile Lys Ala Asn Ser Lys Phe Ile Gly Ile Thr Glu Leu Lys
1               5                   10                  15

Xaa Lys

<210> SEQ ID NO 233
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys-biotin

<400> SEQUENCE: 233
```

```
Phe Ile Gly Ile Thr Glu Leu Lys Lys Leu Glu Ser Lys Ile Xaa Lys
1               5                   10                  15
```

<210> SEQ ID NO 234
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys-biotin

<400> SEQUENCE: 234

```
Ser Lys Phe Ile Gly Ile Thr Glu Leu Lys Lys Leu Glu Ser Xaa Lys
1               5                   10                  15
```

<210> SEQ ID NO 235
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys-biotin

<400> SEQUENCE: 235

```
Ala Asn Ser Lys Phe Ile Gly Ile Thr Glu Leu Lys Lys Leu Xaa Lys
1               5                   10                  15
```

<210> SEQ ID NO 236
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys-biotin

<400> SEQUENCE: 236

```
Ile Lys Ala Asn Ser Lys Phe Ile Gly Ile Thr Glu Leu Lys Xaa Lys
1               5                   10                  15
```

<210> SEQ ID NO 237
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (15)..(15)
<223> OTHER INFORMATION: Aminohexanoic acid
<220> FEATURE:
<221> NAME/KEY: MOD_RES
<222> LOCATION: (16)..(16)
<223> OTHER INFORMATION: Lys-biotin

<400> SEQUENCE: 237

Gln Tyr Ile Lys Ala Asn Ser Lys Phe Ile Gly Ile Thr Glu Xaa Lys
1               5                   10                  15

<210> SEQ ID NO 238
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Aminohexanoic acid
<220> FEATURE:
<221> NAME/KEY: MOD_RES
<222> LOCATION: (14)..(14)
<223> OTHER INFORMATION: Lys-biotin

<400> SEQUENCE: 238

Gly Ile Thr Glu Leu Lys Lys Leu Glu Ser Lys Ile Xaa Lys
1               5                   10

<210> SEQ ID NO 239
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Aminohexanoic acid
<220> FEATURE:
<221> NAME/KEY: MOD_RES
<222> LOCATION: (14)..(14)
<223> OTHER INFORMATION: Lys-biotin

<400> SEQUENCE: 239

Phe Ile Gly Ile Thr Glu Leu Lys Lys Leu Glu Ser Xaa Lys
1               5                   10

<210> SEQ ID NO 240
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Aminohexanoic acid
<220> FEATURE:
<221> NAME/KEY: MOD_RES
<222> LOCATION: (14)..(14)
<223> OTHER INFORMATION: Lys-biotin

<400> SEQUENCE: 240

Ser Lys Phe Ile Gly Ile Thr Glu Leu Lys Lys Leu Xaa Lys
1               5                   10
```

```
<210> SEQ ID NO 241
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Aminohexanoic acid
<220> FEATURE:
<221> NAME/KEY: MOD_RES
<222> LOCATION: (14)..(14)
<223> OTHER INFORMATION: Lys-biotin

<400> SEQUENCE: 241

Ala Asn Ser Lys Phe Ile Gly Ile Thr Glu Leu Lys Xaa Lys
1               5                   10

<210> SEQ ID NO 242
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Aminohexanoic acid
<220> FEATURE:
<221> NAME/KEY: MOD_RES
<222> LOCATION: (14)..(14)
<223> OTHER INFORMATION: Lys-biotin

<400> SEQUENCE: 242

Ile Lys Ala Asn Ser Lys Phe Ile Gly Ile Thr Glu Xaa Lys
1               5                   10

<210> SEQ ID NO 243
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Aminohexanoic acid
<220> FEATURE:
<221> NAME/KEY: MOD_RES
<222> LOCATION: (14)..(14)
<223> OTHER INFORMATION: Lys-biotin

<400> SEQUENCE: 243

Gln Tyr Ile Lys Ala Asn Ser Lys Phe Ile Gly Ile Xaa Lys
1               5                   10

<210> SEQ ID NO 244
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Aminohexanoic acid
<220> FEATURE:
<221> NAME/KEY: MOD_RES
```

```
<222> LOCATION: (12)..(12)
<223> OTHER INFORMATION: Lys-biotin

<400> SEQUENCE: 244

Thr Glu Leu Lys Lys Leu Glu Ser Lys Ile Xaa Lys
1               5                   10

<210> SEQ ID NO 245
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Aminohexanoic acid
<220> FEATURE:
<221> NAME/KEY: MOD_RES
<222> LOCATION: (12)..(12)
<223> OTHER INFORMATION: Lys-biotin

<400> SEQUENCE: 245

Gly Ile Thr Glu Leu Lys Lys Leu Glu Ser Xaa Lys
1               5                   10

<210> SEQ ID NO 246
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Aminohexanoic acid
<220> FEATURE:
<221> NAME/KEY: MOD_RES
<222> LOCATION: (12)..(12)
<223> OTHER INFORMATION: Lys-biotin

<400> SEQUENCE: 246

Phe Ile Gly Ile Thr Glu Leu Lys Lys Leu Xaa Lys
1               5                   10

<210> SEQ ID NO 247
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Aminohexanoic acid
<220> FEATURE:
<221> NAME/KEY: MOD_RES
<222> LOCATION: (12)..(12)
<223> OTHER INFORMATION: Lys-biotin

<400> SEQUENCE: 247

Ser Lys Phe Ile Gly Ile Thr Glu Leu Lys Xaa Lys
1               5                   10

<210> SEQ ID NO 248
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Aminohexanoic acid
<220> FEATURE:
<221> NAME/KEY: MOD_RES
<222> LOCATION: (12)..(12)
<223> OTHER INFORMATION: Lys-biotin

<400> SEQUENCE: 248

Ala Asn Ser Lys Phe Ile Gly Ile Thr Glu Xaa Lys
1               5                   10

<210> SEQ ID NO 249
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Aminohexanoic acid
<220> FEATURE:
<221> NAME/KEY: MOD_RES
<222> LOCATION: (12)..(12)
<223> OTHER INFORMATION: Lys-biotin

<400> SEQUENCE: 249

Ile Lys Ala Asn Ser Lys Phe Ile Gly Ile Xaa Lys
1               5                   10

<210> SEQ ID NO 250
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Aminohexanoic acid
<220> FEATURE:
<221> NAME/KEY: MOD_RES
<222> LOCATION: (12)..(12)
<223> OTHER INFORMATION: Lys-biotin

<400> SEQUENCE: 250

Gln Tyr Ile Lys Ala Asn Ser Lys Phe Ile Xaa Lys
1               5                   10

<210> SEQ ID NO 251
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Aminohexanoic acid
<220> FEATURE:
<221> NAME/KEY: MOD_RES
<222> LOCATION: (10)..(10)
<223> OTHER INFORMATION: Lys-biotin

<400> SEQUENCE: 251
```

```
Leu Lys Lys Leu Glu Ser Lys Ile Xaa Lys
1               5                   10

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Aminohexanoic acid
<220> FEATURE:
<221> NAME/KEY: MOD_RES
<222> LOCATION: (10)..(10)
<223> OTHER INFORMATION: Lys-biotin

<400> SEQUENCE: 252

Thr Glu Leu Lys Lys Leu Glu Ser Xaa Lys
1               5                   10

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Aminohexanoic acid
<220> FEATURE:
<221> NAME/KEY: MOD_RES
<222> LOCATION: (10)..(10)
<223> OTHER INFORMATION: Lys-biotin

<400> SEQUENCE: 253

Gly Ile Thr Glu Leu Lys Lys Leu Xaa Lys
1               5                   10

<210> SEQ ID NO 254
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Aminohexanoic acid
<220> FEATURE:
<221> NAME/KEY: MOD_RES
<222> LOCATION: (10)..(10)
<223> OTHER INFORMATION: Lys-biotin

<400> SEQUENCE: 254

Phe Ile Gly Ile Thr Glu Leu Lys Xaa Lys
1               5                   10

<210> SEQ ID NO 255
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (9)..(9)
<223> OTHER INFORMATION: Aminohexanoic acid
<220> FEATURE:
<221> NAME/KEY: MOD_RES
<222> LOCATION: (10)..(10)
<223> OTHER INFORMATION: Lys-biotin

<400> SEQUENCE: 255

Ser Lys Phe Ile Gly Ile Thr Glu Xaa Lys
1               5                   10

<210> SEQ ID NO 256
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Aminohexanoic acid
<220> FEATURE:
<221> NAME/KEY: MOD_RES
<222> LOCATION: (10)..(10)
<223> OTHER INFORMATION: Lys-biotin

<400> SEQUENCE: 256

Ala Asn Ser Lys Phe Ile Gly Ile Xaa Lys
1               5                   10

<210> SEQ ID NO 257
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Aminohexanoic acid
<220> FEATURE:
<221> NAME/KEY: MOD_RES
<222> LOCATION: (10)..(10)
<223> OTHER INFORMATION: Lys-biotin

<400> SEQUENCE: 257

Ile Lys Ala Asn Ser Lys Phe Ile Xaa Lys
1               5                   10

<210> SEQ ID NO 258
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Aminohexanoic acid
<220> FEATURE:
<221> NAME/KEY: MOD_RES
<222> LOCATION: (10)..(10)
<223> OTHER INFORMATION: Lys-biotin

<400> SEQUENCE: 258

Gln Tyr Ile Lys Ala Asn Ser Lys Xaa Lys
1               5                   10
```

```
<210> SEQ ID NO 259
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin
<220> FEATURE:
<221> NAME/KEY: MOD_RES
<222> LOCATION: (1)..(1)
<223> OTHER INFORMATION: Aminohexanoic acid

<400> SEQUENCE: 259

Xaa Ser Lys Phe Ile Gly Ile Thr Glu Leu Lys Lys Leu Glu Ser Lys
1               5                   10                  15

Ile Asn Lys Val Phe
            20

<210> SEQ ID NO 260
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin
<220> FEATURE:
<221> NAME/KEY: MOD_RES
<222> LOCATION: (1)..(1)
<223> OTHER INFORMATION: Aminohexanoic acid

<400> SEQUENCE: 260

Xaa Phe Ile Gly Ile Thr Glu Leu Lys Lys Leu Glu Ser Lys Ile Asn
1               5                   10                  15

Lys Val Phe

<210> SEQ ID NO 261
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Azidopropionyl group

<400> SEQUENCE: 261

Leu Glu Gln Leu Glu Ser Ile Ile Asn Phe Glu Lys Leu Ala Ala Ala
1               5                   10                  15

Ala Ala Lys

<210> SEQ ID NO 262
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Leu Glu Gln Leu Glu Ser Ile Ile Asn Phe Glu Lys Leu Ala Ala Ala
1               5                   10                  15

Ala Ala Lys
```

US 9,522,962 B2

PEPTIDES, CONJUGATES AND METHOD FOR INCREASING IMMUNOGENICITY OF A VACCINE

CROSS-REFERENCE TO RELATED APPLICATION(S)

This application is the National Phase of International Patent Application No. PCT/NL2011/050180, filed Mar. 15, 2011, published as WO 2011/115483 A1, which claims priority to European Application No. 10156505.9, filed Mar. 15, 2010 and Provisional Application No. 61/317,930, filed Mar. 26, 2010. The contents of these applications are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jun. 5, 2013, is named 069818-7225 SL.txt and is 134,577 bytes in size.

FIELD OF THE INVENTION

The present invention relates to the field of vaccines, such as vaccines against cancer or an infectious disease. In particular, the present invention provides an immunogen comprising a peptide derived from tetanus toxin for induction of potent humoral and cellular immune responses when administered to subjects having antibodies against tetanus toxin.

BACKGROUND OF THE INVENTION

Almost all new vaccines are less effective than required, particularly when infection has already established itself. The best vaccines are based on empirical observations. These are e.g. killed or attenuated micro-organisms. In general such vaccines comprise all components required for the induction of effective and protective immune responses. However, these vaccines are usually poorly defined. Moreover, they contain many unknown components, the mechanism of action is usually largely unknown, they can't be produced reproducible and they thus don't fulfil the criteria for modern drugs. They are only applied because nothing better is available at present. In the case of vaccines against cancer things are even more complicated, because the utilization of material from nature, i.e. cancer cells, is unacceptable.

In order for vaccines to elicit a protective immune response against microbial pathogens a sufficient efficacy of vaccine uptake by antigen presenting cells (APC) such as dendritic cells and macrophages is required. The APC have to internalize the antigens and to transport them to the regional draining lymph nodes where they process and present the antigenic peptides on class I and class II MHC molecules for the activation of CD8+ and CD4+ T cells, respectively (Zinkernagel et al. (1999) Immunol Rev 156: 199-209; Banchereau and Steinman (1998) Nature 392:245-252).

However, due to poor uptake by APC, several vaccines have limited immunogenicity, even though they are comprised of proteins that are antigenic in humans. The poor uptake is probably because many vaccinating proteins in solution, as well as particulate vaccines, lack markers that identify them for internalization and processing by APC and therefore the uptake of such a vaccine is mediated only by random endocytosis into APC and thereby minimal (Abdel-Motal et al. (2009) Vaccine 27:3072-3082).

The immunogenicity of microbial vaccines, such as tetanus toxoid, was shown to be improved when the vaccines are administered as immune complex with their corresponding IgG antibody (Raveth and Clynes (1998) Annu Rev Immunol 16:421-432; Schuurhuis et al. (2002) J Immunol 168: 2240-2246; Gosselin et al. (1992) J Immunol 149:3477-3481). However, a disadvantage is that the immune complex has to be formed with an antibody that has an Fc domain which effectively binds to the Fc-gamma receptor on APC, whereas the Fc domain of many monoclonal antibodies has poor interaction with the Fc-gamma receptor on APC. A further disadvantage is that in the complex immunodominant peptide epitopes may be masked, and thus result in poor immunogenicity.

Another strategy to improve the immunogenicity of vaccines is presented in WO 2008/118487, wherein an influenza virus bearing α-gal epitopes (Galα1-3Galβ1-4(3)GlcNAc-R) is disclosed, resulting in enhanced targeting of the virions to APC and in a heightened humoral and cellular immune response to influenza. However, synthetising α-gal epitopes is more difficult as compared to synthesis of regular peptides and as a consequence more expensive.

Volk et al. (1984, Infect. Immun. 45:604-609) disclose a tetanus toxin fragment comprising the N-terminal half of the toxin heavy chain including the sequence GITELKKL that spans residues 383 to 390 of the toxin heavy chain as depicted in SEQ ID NO:3 herein and antibodies thereto.

Raju et al. (1996, J. Autoimmun. 9:79-88) disclose overlapping synthetic peptides, each 20 residues in length, used to determine the epitope repertoire of human CD4+ T cells. One of the peptides recognized by said cells spans residues 371-390 of the tetanus toxin heavy chain, fully comprising the sequence GITELKKL (residues 383-390 of SEQ ID NO: 3).

Demotz et al. (1989, J. Immunol. 142:394-402) disclose monoclonal antibodies that bind B fragment of tetanus toxin and recombinant fragments 744-1315 and 604-1315 comprising the sequence GITELKKL (residues 383-390 of SEQ ID NO: 3).

Engstrom et al. (J. Immunoassays 16: 231-245) disclose a "peptide 20", comprising the sequence GITEL (SEQ ID NO: 220), that is recognized by human IgG and IgA antibodies.

WO 2004/000873 discloses a conjugate comprising a tetanus epitope derived from the tetanus heavy chain sequence 830-843 comprising the sequence GITE (SEQ ID NO: 221).

Fischer et al. (1994, Mol. Immunol. 31:1141-1148) disclose epitope mapping of antibodies raised in mice and rabbits to tetanus toxoid and that hexapeptides from the region spanning residues 350-400 of the tetanus toxoid heavy chain show high reactivity to the antibodies.

However, none of the prior art teaches or suggests peptides comprising a linear epitope from tetanus toxin against which circulating antibodies are frequently present in the human population. Nor does the prior art teach or suggest the use of these peptides for conjugation to an antigen against which an immune response is desired, in order to increase the efficiency with which this desired immune response can be induced.

Thus, there is still a need in the art for methods and means to increase the immunogenicity of vaccines.

SUMMARY OF THE INVENTION

A first embodiment of the invention relates to a conjugate, comprising a peptide conjugated to an antigen, immunogen or to a vehicle comprising an antigen or immunogen, wherein the peptide comprises: (i) at least 10 amino acid residues of SEQ ID NO:3 that comprise the amino acid sequence GITELKKL (residues 383-390 of SEQ ID NO: 3); or, (ii) an amino acid sequence having at least 80% sequence identity with an amino acid sequence as provided under (i) and wherein the peptide, when subjected to serum samples from at least 10 human subjects that had been vaccinated with tetanus toxoid is in at least 50% of the serum samples bound by antibodies from the serum samples, as determined in a Tettox ELISA; and wherein the peptide is not the tetanus toxin beta chain.

In a second embodiment, the peptide comprises less than 100 amino acid residues.

The third embodiment relates to a conjugate according to the first or second embodiments, wherein the antigen, the immunogen or the vehicle comprising the antigen or immunogen is conjugated to the C-terminus of the peptide.

The fourth embodiment relates to a conjugate according to previous embodiments, wherein 2 to 20 peptides are bound to the antigen, immunogen or the vehicle comprising the antigen or immunogen.

The fifth embodiment relates to a conjugate according to the previous embodiments, for use as a medicament. Preferably the conjugate is for use as a medicament in a subject who has antibodies against tetanus toxin or tetanus toxoid. More preferably, the medicament is a prophylactic or therapeutic vaccine.

The sixth embodiment relates to a conjugate according to any one of the first to fourth embodiments, for use in the prevention or treatment of cancer or an infectious disease in a subject.

The seventh embodiment relates to the use of a conjugate according to any one of the first to fourth embodiments, for the manufacture of a medicament for the prevention or treatment of cancer or an infectious disease in a subject. Preferably the conjugate is for use as a medicament in a subject who has antibodies against tetanus toxin or tetanus toxoid.

In an eigth embodiment, the conjugate is for use as a medicament in a subject to whom a vaccine for generating circulating antibodies to tetanus toxin has been administered at least 2 weeks prior to administering the conjugate.

In a ninth embodiment, the conjugate or its use as medicament are for antibody mediated antigen-targeting.

In a tenth embodiment, the conjugate or its use as medicament are for the treatment of cancer whereby treatment further comprises surgery, chemotherapy and/or radiation therapy.

In an eleventh embodiment, the conjugate or its use as medicament are for treatment of a subject who has antibodies against tetanus toxin or tetanus toxoid has been immunized with tetanus toxoid, has had post-exposure prophylaxis for tetanus and/or has suffered from tetanus.

In a twelfth embodiment, in the conjugates of the invention, the antigen or immunogen comprises a T cell epitope. More preferably, the antigen or immunogen comprises a cytotoxic T cell and/or a T helper cell epitope.

In a thirteenth embodiment, in the conjugates of the invention, the peptide and the antigen, immunogen or the vehicle comprising an antigen or immunogen are conjugated via a linker. Preferably the linker is aminohexanoic acid—biotinylated lysine. In another embodiment, in the conjugates of the invention, the peptide and the antigen, immunogen or the vehicle comprising an antigen or immunogen are conjugated without a linker. In a preferred embodiment, in the conjugates of the invention, the peptide and the antigen, immunogen or the vehicle comprising an antigen or immunogen are conjugated through a covalent bond.

In a fourteenth embodiment, the invention relates to a peptide comprising: (i) at least 12 amino acid residues of SEQ ID NO:3 that comprise the amino acid sequence GITELKKLES (SEQ ID NO: 5); or, (ii) an amino acid sequence of at least 12 amino acid residues having at least 80% sequence identity with an amino acid sequence as provided under (i) and wherein the peptide, when subjected to serum samples from at least 10 human subjects that had been vaccinated with tetanus toxoid is in at least 50% of the serum samples bound by antibodies from the serum samples, as determined in a Tettox ELISA; wherein the peptide comprises less than 100 amino acids.

In a fifteenth embodiment, the invention relates to a peptide comprising: (i) the amino acid sequence as provided in any one of SEQ ID NOS:4-24, 223-235, 237-240, or 245-246; or (ii) an amino acid sequence having at least 80% sequence identity with the amino acid sequence as provided in SEQ ID NOS:4-24, 223-235, 237-240, or 245-246 and wherein the peptide, when subjected to serum samples from at least 10 human subjects that had been vaccinated with tetanus toxoid is in at least 50% of the serum samples bound by antibodies from the serum samples, as determined in a Tettox ELISA.

In a sixteenth embodiment, the invention relates to a peptide according to the fifteenth embodiment, wherein the peptide comprises or consists of the amino acid sequence as provided in SEQ ID NO:24.

In a seventeenth embodiment, the invention relates to a peptide according to a peptide according to any one of the fourteenth to sixteenth embodiments, wherein the peptide comprises less than 50 amino acid residues.

In a eighteenth embodiment, the invention relates to a peptide according to a peptide according to any one of the fourteenth to seventeenth embodiments, wherein the peptide comprises further amino acid residues at the C-terminus of SEQ ID NO:4, SEQ ID NO: 246, or SEQ ID NO:24.

In a nineteenth embodiment, the invention relates to a peptide according to the eighteenth embodiment, wherein the further amino acid residues are not derived from the tetanus toxin beta chain.

DESCRIPTION OF THE INVENTION

Definitions

The term "immune response" as used herein refers to the production of antibodies and/or cells (such as T lymphocytes) that are directed against, or assist in the decomposition or inhibition of, a particular antigenic epitope or particular antigenic epitopes. The phrases "an effective immunoprotective response", "immunoprotection", and like terms, for purposes of the present invention, mean an immune response that is directed against one or more antigenic epitopes of a pathogen or against one or more antigenic epitopes of a cancer cell so as to protect against infection by the pathogen or against cancer in a vaccinated subject. For purposes of the present invention, protection against infection by a pathogen or protection against cancer includes not only the absolute prevention of infection or cancer, but also any detectable reduction in the degree or rate of infection by a pathogen or of the cancer, or any detectable reduction in the severity of the disease or any symptom or condition resulting from infection by the pathogen or cancer in the vaccinated subject, for example as compared to an unvaccinated infected subject. An effective immunoprotective response in the case of cancer also includes clearing up the cancer cells, thereby reducing the size of cancer or even abolishing the cancer. Vaccination in order to achieve this is also called therapeutic vaccination.

An effective immunoprotective response can be induced in subjects that have not previously been infected with the pathogen and/or are not infected with the pathogen or do not yet suffer from cancer at the time of vaccination. An effective immunoprotective response can also be induced in a subject already infected with the pathogen or already suffering from cancer at the time of vaccination.

According to the present invention, the general use herein of the term "antigen" refers to any molecule that binds specifically to an antibody. The term also refers to any molecule or molecular fragment that can be bound by an MHC molecule and presented to a T-cell receptor. Antigens can be e.g. proteinaceous molecules, i.e. polyaminoacid sequences, optionally comprising non-protein groups such as carbohydrate moieties and/or lipid moieties or antigens can be e.g. molecules that are not proteinaceous such as carbohydrates. An antigen can be e.g. any portion of a protein (peptide, partial protein, full-length protein), wherein the protein is naturally occurring or synthetically derived, a cellular composition (whole cell, cell lysate or disrupted cells), an organism (whole organism, lysate or disrupted cells) or a carbohydrate or other molecule, or a portion thereof, that is able to elicit an antigen-specific immune response (humoral and/or cellular immune response) in a particular subject, which immune response preferably is measurable via an assay or method.

The term "antigen" can herein be used interchangeably with the term "immunogen", and is used herein to describe a protein, peptide, cellular composition, organism or other molecule which elicits a humoral and/or cellular immune response (i.e., is antigenic), such that administration of the immunogen to a subject (e.g., via a vaccine of the present invention) mounts an immunogen-specific immune response against the same or similar immunogens/antigens that are encountered within the tissues of the subject. Therefore, to vaccinate a subject against a particular antigen means, in one embodiment, that an immune response is elicited against the antigen or immunogenic portion thereof, as a result of administration of the antigen. Vaccination preferably results in a protective or therapeutic effect, wherein subsequent exposure to the antigen (or a source of the antigen) elicits an immune response against the antigen (or source) that reduces or prevents a disease or condition in the subject. The concept of vaccination is well known in the art. The immune response that is elicited by administration of a prophylactic or therapeutic composition of the present invention can be any detectable change in any facet of the immune status (e.g., cellular response, humoral response, cytokine production), as compared to in the absence of the administration of the vaccine.

An "epitope" is defined herein as a single immunogenic site within a given antigen/immunogen that is sufficient to elicit an immune response in a subject. Those of skill in the art will recognize that T cell epitopes are different in size and composition from B cell epitopes, and that T cell epitopes presented through the Class I MHC pathway differ from epitopes presented through the Class II MHC pathway. Epitopes can be linear sequence or conformational epitopes (conserved binding regions) depending on the type of immune response. An antigen can be as small as a single epitope, or larger, and can include multiple epitopes. As such, the size of an antigen can be as small as about 5-12 amino acids (e.g., a peptide) and as large as: a full length protein, including a multimer and fusion proteins, chimeric proteins, whole cells, whole microorganisms, or portions thereof (e.g., lysates of whole cells or extracts of microorganisms).

As used herein, the term "antibody" means an immunoglobulin molecule or a fragment of an immunoglobulin molecule having the ability to specifically bind to a particular antigen. Antibodies are well known to those of ordinary skill in the science of immunology.

The term "immunogenicity" of a vaccine is herein defined as the ability to induce and activate T-cells (both cytotoxic T cells and T helper cells) and elicit antibody production in a subject.

The term "antibody mediated antigen-targeting" is used herein to indicate an antigen delivery system that uses antibody (such as e.g. IgG) mediated antigen targeting via Fc receptors that are expressed on the cell surface of APC, such as for example DC and macrophages. By making use of antigen-specific antibodies, complexes of these antibodies with the protein antigen can be formed in vitro but also in vivo. These complexes (so-called immune complexes (IC)) can be bound by the APC via these Fc receptors, subsequently taken up, and the antigen will then be processed and a peptide derived thereof will be presented to specific T cells. It is important that in antibody mediated antigen-targeting IC will also activate the APC and that leads to optimal stimulation of the specific T cells (Schuurhuis et al., J Immunol. 168, 2240-2246, 2002). Thus, in antibody mediated antigen-targeting, specific antibodies circulating in human beings are used to selectively target antigens to stimulate the cellular immune system.

The term "peptide" as used herein is defined as a chain of amino acid residues, usually having a defined sequence. As used herein the term peptide is interchangeable with the terms "polypeptide" and "protein". In the context of the present invention, the term "peptide" is defined as being any peptide or protein comprising at least two amino acids linked by a modified or unmodified peptide bond. The term "peptide" refers to short-chain molecules such as oligopeptides or oligomers or to long-chain molecules such as proteins. A peptide according to the present invention can comprise modified amino acids. Thus, the peptide of the present invention can also be modified by natural processes such as post-transcriptional modifications or by a chemical process. Some examples of these modifications are: acetylation, acylation, ADP-ribosylation, amidation, covalent bonding with flavine, covalent bonding with a heme, covalent bonding with a nucleotide or a nucleotide derivative, covalent bonding to a modified or unmodified carbohydrate moiety, bonding with a lipid or a lipid derivative, covalent bonding with a phosphotidylinositol, cross-linking, cyclization, disulfide bond formation, demethylation, cysteine molecule formation, pyroglutamate formation, formylation, gamma-carboxylation, hydroxylation, iodination, methylation, oxidation, phosphorylation, racemization, hydroxylation, etc. Thus, any modification of the peptide which does not have the effect of eliminating the immunogenicity of the peptide, is covered within the scope of the present invention.

The term "sequence identity" is herein defined as a relationship between two or more amino acid (peptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one peptide to the sequence of a second peptide. "Identity" and "similarity" can be readily calculated by various methods, known to those skilled in the art. In a preferred embodiment, sequence identity is determined by comparing the whole length of the sequences as identified herein. Preferred methods to determine identity are designed to give the largest match between the sequences tested. Methods to determine identity and similarity are codified in publicly available computer programs. Preferred computer program methods to determine identity and similarity between two sequences include e.g. the BestFit, BLASTP, BLASTN, and FASTA (Altschul, S. F. et al., J. Mol. Biol. 215:403-410 (1990), publicly available from NCBI and other sources (BLAST Manual, Altschul, S., et al., NCBI NLM NIH Bethesda, Md. 20894). A most preferred algorithm used is EMBOSS Preferred parameters for amino acid sequences comparison using EMBOSS are gap open 10.0, gap extend 0.5, Blosum 62 matrix. Preferred parameters for nucleic acid sequences comparison using EMBOSS are gap open 10.0, gap extend 0.5, DNA full matrix (DNA identity matrix). Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is, alanine, valine, leucine, and isoleucine; a group of amino acids having aliphatic-hydroxyl side chains is serine and threonine; a group of amino acids having amide-containing side chains is asparagine and glutamine; a group of amino acids having acidic side chains is aspartic acid and glutamic acid; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred amino acid substitutions are substitution of an amino acid with an amino acid from the same conservative amino acid group. These conservative amino acid groups are: alanine-valine-leucine-isoleucine-methionine; phenylalanine-tyrosine-tryptophane; lysine-arginine-histidine; asparagine-glutamine; aspartic acid and glutamic acid; serine-threonine; glycine-proline. In this particular case another conservative amino acid substitution group is lysine-formyllysine The terms "tumour" or "cancer" in a subject refers to the presence of cells possessing characteristics such as atypical growth or morphology, including uncontrolled proliferation, immortality, metastatic potential, rapid growth and proliferation rate, and certain characteristic morphological features. Often, cancer cells will be in the form of a tumour, but such cells may also exist in isolation from one another within a subject. "Tumour" includes both benign and malignant neoplasms.

In the context of the invention, a "patient" or "subject" may be an animal (including humans). Preferably, a patient or subject is a human being.

The term "Tettox elisa" is used herein to indicate a specific elisa for tetanus toxoid antibodies, which is further defined elsewhere herein.

DETAILED DESCRIPTION OF THE INVENTION

The present inventors have previously shown that pre-formed immune complexes (IC) are very potent vaccine formulations for efficient priming T cell responses in mice (Schuurhuis et al., J Immunol. 168, 2240-2246, 2002). By complexing the protein antigen ovalbumine (OVA) with antibodies against OVA the inventors were able to efficiently target the antigen to dendritic cells (DC), simultaneously leading to strong DC maturation. These matured DC cross-presented OVA-derived peptides to CD8 T cells in vitro and were highly effective in priming CD8+ T cells upon immunization in mice. Importantly, these T cell responses were able to control tumours in vivo, especially effective when these IC were pre-loaded on DC (Schuurhuis et al., J Immunol 176, 4573-4580, 2006). Immunization with DC loaded with preformed IC resulted in protective tumor immunity but also therapeutic treatment of tumor-bearing mice. The tumor control in vivo was dependent on the presence of activating Fc receptors on DC and the induction of specific CD8+ cytotoxic T cells. These findings show that specific antibody-mediated antigen targeting to DC is a highly effective mode of induction of T cell immunity against cancer.

The inventors of the present invention have now surprisingly found that also pre-existing, circulating antibodies can be used to efficiently prime specific T cell proliferation in mice. Antibodies against the hapten TNP (a trinitrophenyl group attached to a peptide or protein) were induced by immunization with a specific hapten-carrier (TNP-BSA). Subsequently, the immunized mice were challenged with a non-related protein antigen coupled to the same hapten (TNP-OVA). It was found that T cell responses against the non-related protein antigen OVA were induced at a much higher level in these mice compared to control mice that had been vaccinated with BSA without TNP. These findings provide a proof-of-principle that the immunogenicity of a vaccination can be improved by making use of circulating antibodies that are already present at the moment of vaccination. Because of the interspecies differences between mice and man a different group of circulating antibodies must be targeted and therefore, the inventors present a peptide that can be applied in human beings for the improvement of vaccine efficacy and immunogenicity.

This approach mimics as much as possible the natural immune response used by the body's immune system to get rid of invading micro-organisms, in particular micro-organisms that infest and depend on the body's cells such as viruses and intracellular bacteria such as for example tuberculosis bacilli. The vaccine approach of the present invention actually makes optimal use of the two major arms of specific immunity, namely pre-existing antibodies in the blood plasma, and cell-mediated immunity provided by T-cells. The invention utilizes the Fc fragment of antibodies to deliver antigen bound at the other end of the antibody to the antigen-presenting cells. Prior work has shown that this is one of the most efficient ways to target the immunizing antigen to antigen presenting cells (APC), i.e. the cells that initiate immune responses in the body, such as for example dendritic cells (DC) or macrophages. For the present invention, the DC are the most important APC. Without wishing to be bound to any theory, it seems that because antigens eliciting the required cell-mediated immunity are physically linked to the defined amino acids that bind to pre-existing antimicrobial antibodies in the plasma, an extraordinary focusing of antigen of unprecedented efficiency onto APC, e.g. DC, will occur, through binding of the antibody-bound complexes to so-called Fc Receptors on the APC (see FIG. 1). This allows not only very efficient introduction of the target antigens (i.e., virus or tumour target antigens) into the APC, but also induces vigorous activation of the APC. Both events are essential for induction of robust therapeutic cell-mediated immune responses (T-cell responses), required for eradication of abnormal cells, such as tumour cells or virus-infected cells. Indeed, in experiments in mice with antibody-binding compounds, conjugated to peptides eliciting T-cell responses, this approach strongly augmented T-cell responses, compared to responses seen against non-conjugated components.

For historic reasons, modern pharmaco-dynamics and pharmaco-distribution science have hardly been applied to vaccines. Taking into account the complex nature of traditional vaccines, this is no surprise, because tracing the fate in the human body of each of the breakdown products of traditional vaccines, largely composed of heat-killed or attenuated organisms, would constitute a next to impossible task. Such arguments do not apply, however, to a vaccines of the present invention. First, the more drug-like nature of a vaccine according to the present invention allows much better in vivo fate determination of the vaccine. Second, pharmaco-dynamic and pharmaco-distribution studies of the new generation of vaccines are sheer necessity to develop their therapeutic potential in a rational manner. The challenge in designing and testing the new vaccines is how to make them more potent and thus convert them from purely preventive vaccines, that largely rely on neutralizing antibodies, into therapeutic vaccines that possess the potency required to induce strong T-cell responses and cure established persistent infections and diseases caused by infections, such as viral cancer as well as have curative impact on non-infectious conditions such as non-viral cancer.

Peptide

A peptide according to the present invention, preferably is a molecule against which already circulating antibodies are available in the subject wherein the immune response is desired. Tetanus toxin (TTx), also known as tetanospasmin, spasmogenic toxin, TeTx, TeNT and TTX, is one of the most toxic proteins known. TTx is a neurotoxin produced by the vegetative spore of *Clostridium tetani* in anaerobic conditions and causes tetanus in humans. It exists as a heavy and a light chain connected via a disulfide bond between cysteines L438 en H10 and non-covalent interactions. Tetanus toxoid (TTd) is prepared by detoxifying TTx by treatment of the protein with formalin. This treatment results in various modifications of the protein (e.g. formylation of the side chains of lysine residues and the formation of inter- and intramolecular crosslinks). Although TTd is a modified form of TTx (and is thus a different protein) TTd is able to induce protective immunity against tetanus, which implies that antibodies raised by TTd vaccination recognize TTx. The present inventors have searched for linear epitopes of TTd antibodies using non-modified linear peptides from the TTx amino acid sequence. Tetanus toxin has 1314 amino acids (SEQ ID NO:1) and is synthesized by *C. tetani* as a single peptide chain that is proteolyzed to yield two fragments, the light chain (LC; also known as alpha chain) derived from the amino terminus (SEQ ID NO:2), and the heavy chain (HC; also known as beta chain) derived from the carboxyl terminus (SEQ ID NO:3).

Tetanus toxoid (TTd) is used in immunization, such as for example the childhood DTP combination vaccine against three infectious diseases (diphtheria, pertussis (whooping cough), tetanus) or the DTP-poliomyelitis vaccine. Almost all people have been immunized with tetanus toxoid (TTd) early in life, since it is included in the vaccine that is used in the children vaccination program of many countries. In addition, many people have been challenged later in life with TTd, since anti-tetanus vaccination is a common procedure after injuries suspected of being potential cause of a tetanus infection. As a consequence, anti-tetanus toxin/toxoid antibodies are present in a significant part of the human population of industrialised countries. Hence, targeting of conjugates comprising a TTx/TTd epitope, i.e. a peptide according to the invention, to APC may be expected to be effective in such vaccinees, as a result of in situ formation of immune complexes between the anti-tetanus toxin/toxoid antibodies and conjugates comprising a TTx/TTd epitope.

In a first aspect the present invention relates to a peptide comprising: (i) at least 10 amino acid residues of SEQ ID NO:3 that comprise the amino acid sequence GITELKKL (residues 383-390 of SEQ ID NO: 3); or (ii) an amino acid sequence having at least 70, 80, 90 or 100% sequence identity with an amino acid sequence as provided under (i) and wherein the peptide, when subjected to serum samples from at least 10 human subjects that have been vaccinated with a tetanus toxoid is in at least 50% of the serum samples bound by antibodies from the serum samples, as determined in a Tettox ELISA; and wherein the peptide is not the tetanus toxin beta chain. Preferably, the at least 10 amino acid residues of SEQ ID NO:3 in (i) are 10 consecutive amino acids from SEQ ID NO:3. Preferably, an amino acid sequence having at least 70, 80, 90 or 100% sequence identity with an amino acid sequence as provided under (i) is an amino acid sequence of 10 amino acids of which at least 7, 8, 9, or 10 amino acids are identical to 10 consecutive amino acid residues of SEQ ID NO:3 that comprise the amino acid sequence GITELKKL (residues 383-390 of SEQ ID NO: 3).

Preferably, a peptide according to (ii) above, is subjected to serum samples from at least 10, 12, 15, 20, 25, 30, 40, 50, 60, 70, 100, 150, 250 or more human subjects. More preferably, the serum samples are from human subjects that have a high titer of anti-TTd antibodies, e.g. at least 100 International Units (IU) per ml as determined using the Tettox ELISA as described hereafter. In a preferred embodiment, the human subjects are randomly selected human subjects, preferably randomly selected human subjects having a high titer of anti-TTd antibodies as described above.

A Tettox ELISA is preferably performed as follows: a 96-wells plate (preferably from Euro-Diagnostica, Arnhem, The Netherlands) is coated with streptavidin. The streptavidin coated 96 wells plate is blocked with PBS containing 5% BSA (200 µl/well, 1 h, room temperature). Subsequently, the plate is washed three times with PBS containing 0.05% TWEEN20® (polysorbate 20). A biotinylated peptide is coated by 1 h incubation at room temperature with 100 µl/well of a 2 µg/ml solution of the biotinylated peptide in PBS containing 1% BSA. The plate is washed three times with PBS containing 0.05% TWEEN20® (polysorbate 20) followed by incubation for 1 h at room temperature with 100 µl serum from TWEEN20® (polysorbate 20) a human subject as defined above (preferably having a high titer of anti-TTd antibodies) that had been diluted at least 100, 200, 400, 500 or 1000 times and preferably not more than 100,000, 10,000, 7,500, 5,000 or 2,500 times with PBS containing 1% BSA. Then the plate is washed three times with PBS containing 0.05% TWEEN20®(polysorbate 20). Each well is incubated for 1 h at room temperature with a HRP-conjugated IgG antibody (mouse anti-human IgG-HRP monoclonal, clone G18-145, cat no 555788, Becton Dickinson, 100 µl/well of a 1000× dilution in PBS containing 0.05% TWEEN20® (polysorbate 20)) after which the plate is washed three times with PBS containing 0.05% TWEEN20® (polysorbate 20). Development is performed with 2,2'-azino-di-(3-ethylbenzthiazoline sulfonic acid), ABTS+$H_2O_2$ 1/1000, 100 µl/well. Optical density is measured at 415 nm with a BIO-RAD, model 680, microplate reader. In each plate, preferably a negative contol is included, more preferably at least in triplicate. A preferred negative contol is serum from a human subject without detectable anti-TTd antibodies. Another preferred negative control is a solution of BSA. A peptide according to (ii) above is a peptide according to the invention if it is bound by antibodies in at least 40, 45, 50, 55, 60, 65, 70, 75, 80, 85, 87, 90, 91, 92, 93, 94, 95, 96, 97, 98, 99% most preferably 100% of the tested human serum samples. A peptide is considered to be bound by antibodies in a serum sample if the determined optical density for that particular serum sample is at least 2.0, more preferably 2.5, 3.0, 3.5 or more times higher as compared to the optical density that is determined for the negative control.

Alternatively, the peptide under (ii) is a peptide according to the invention if it can be bound by antibodies present in TETAQUIN® (Sanquin, Amsterdam, The Netherlands). In the Tettox ELISA as described above, instead of serum from a human subject, 100 µl TETAQUIN® that had been diluted 800× with PBS containing 1% BSA may be used, in which case the peptide is considered to be bound by antibodies in TETAQUIN® if the determined optical density for the sample is at least 2.0, more preferably 2.5, 3.0, 3.5 or more times higher as compared to the optical density that is determined for the negative control.

Preferably, all measurements in the Tettox ELISA are performed in duplicate, more preferably in triplicate or more.

Preferably, a peptide according to the invention comprises the amino acid sequence of FIGITELKKL (SEQ ID NO:4), GITELKKLES (SEQ ID NO:5) or IGITELKKLE (SEQ ID NO:6). More preferably, a peptide according to the invention consists of the amino acid sequence of FIGITELKKL (SEQ ID NO:4), GITELKKLES (SEQ ID NO:5) or IGITELKKLE (SEQ ID NO:6).

In one embodiment, the present invention relates to a peptide according to the invention, comprising: (i) the amino acid sequence as provided in any one of SEQ ID NO: 4-24; or (ii) an amino acid sequence having at least 70, 80, 90 or 100% sequence identity and/or at least 70, 80, 90 or 100% sequence similarity with the amino acid sequence as provided in SEQ ID NOS: 4-24, 223-235, 237-240, or 245-246 and wherein the peptide, when subjected to serum samples from at least 10 human subjects that had been vaccinated with tetanus toxoid is in at least 50% of the serum samples bound by antibodies from the serum samples, as determined in a Tettox ELISA as described above. Preferably, the peptide does not comprise further amino acid residues at its N-terminus. More preferably, the present invention relates to a peptide according to the invention, wherein the peptide comprises the amino acid sequence as provided in SEQ ID NO:24.

A peptide of the invention comprises or consists of at least 10 amino acid residues, preferably of at least 11, 12, 13, 14, 15, 16, 17, 18, 19, 20, 21, 22, 23, 24, 25, 26, 27, 28, 29, 30, 31, 32, 33, 34, 35, 40, 45, 50, 55, 60 or more amino acid residues.

In yet a further embodiment, the present invention relates to a peptide of the invention, wherein the peptide comprises or consists of less than 100 amino acid residues, more preferably less than 90, 80, 70, 60, 50, 40, 30, 20 amino acid residues. More preferably a peptide according to the invention consists of 18 amino acid residues, and most preferably a peptide according to the invention consists of SEQ ID NO:24.

In another embodiment, in a peptide of the present invention amino acid residues are substituted by other amino acid residues, preferably by conservative amino acid residues as is further defined above. Amino acid residues in a peptide of the invention that are substituted, are preferably the amino acid residues on position 381, 382, 386-390, 392-398 of SEQ ID NO:3.

Alternatively or in combination with at least a previous embodiment, the invention relates to an embodiment, wherein the peptide comprises further amino acid residues at the C-terminus of SEQ ID NOS: 4-24, 223-235, 237-240, or 245-246.

In another embodiment, the present invention relates to a peptide according to the invention, wherein the further amino acid residues are not derived from tetanus toxin or the tetanus toxin beta chain.

In another embodiment, the present invention relates to a peptide of the invention, wherein the peptide consists of the amino acid sequence as described in any one of claims 1-3.

In a further embodiment, the peptide of the invention is a peptide presented in Table 2 and having an OD greater than 0.2, 0.25, 0.35, 0.45, 0.6, 0.75, 0.8, 0.85, 1.0, 1.05, 1.1, or 1.15; a peptide presented in Table 3 and having an OD greater than 0.3, 0.35, 0.4, 0.75, 1.0, 1.15, 1.45, 1.5, 1.55, 1.65, 1.7, 1.85, 1.9, or 2.0; a peptide presented in Table 5 and having an OD greater than 0.16, 0.18, 0.3, 0.38, 0.62, 0.65, 0.7, 0.71, 0.85, 0.88, 0.9, 0.91, or 1.0; or a peptide presented in Table 6 and having an OD with at least one of TETAQUIN® or serum 034960 greater than 0.37, 0.41, 0.7, 0.72, 0.8, 0.83, 0.88, 0.9, 0.95, 0.97, 1.01, 1.02, 1.04, or 1.1. These ODs are determined according to the Tettox Elisa using TETAQUIN® as described elsewhere herein The invention additionally provides a method of preparing the peptides of the invention. A peptide of the invention is preferably produced by chemical synthesis and subsequent purification (e.g. see Examples).

The individual residues of the peptides of the invention protein can be incorporated in the peptide by a peptide bond or peptide bond mimetic. A peptide bond mimetic of the invention includes peptide backbone modifications well known to those skilled in the art. Such modifications include modifications of the amide nitrogen, the α-carbon, amide carbonyl, complete replacement of the amide bond, extensions, deletions or backbone cross-links See, generally, Spatola, Chemistry and Biochemistry of Amino Acids, Peptides and Proteins, Vol. VII (Weinstein ed., 1983). Several peptide backbone modifications are known, these include, ψ $[CH_2S]$, ψ $[CH_2NH]$, ψ $[CSNH_2]$, ψ [NHCO], ψ $[COCH_2]$ and ψ [(E) or (Z) CH═CH]. The nomenclature used above, follows that suggested by Spatola, above. In this context, ψ indicates the absence of an amide bond. The structure that replaces the amide group is specified within the brackets.

Amino acid mimetics may also be incorporated in the peptides. An "amino acid mimetic" as used here is a moiety other than a naturally occurring amino acid that conformationally and functionally serves as a substitute for an amino acid in a peptide of the present invention. Such a moiety serves as a substitute for an amino acid residue if it does not interfere with the ability of the peptide to bind to TTd antibodies in a manner defined herein above. Amino acid mimetics may include non-protein amino acids, such as β-, γ-, δ-amino acids, β-, γ-, δ-imino acids (such as piperidine-4-carboxylic acid) as well as many derivatives of L-α-amino acids. A number of suitable amino acid mimetics are known to the skilled artisan, they include cyclohexylalanine, 3-cyclohexylpropionic acid, L-adamantyl alanine, adamantylacetic acid and the like. In addition, D-amino acids can be regarded as mimetics. Peptide mimetics suitable for peptides of the present invention are discussed by Morgan and Gainor, (1989) Ann. Repts. Med. Chem. 24:243-252.

Conjugate

In another aspect, the present invention relates to a conjugate, comprising a peptide as defined above and an immunogen or a vehicle comprising an immunogen. Preferably, the peptide as defined above is conjugated at its C-terminus to an immunogen or to a vehicle comprising an immunogen.

A conjugate according to the present invention can serve to improve a wide variety of vaccines, including vaccines for prevention and/or treatment of infectious diseases (such as e.g. viral or bacterial vaccines) and of (non-viral) cancers (such as e.g. a tumor vaccine). For example, the invention can advantageously be used in vaccines against viruses like HIV, Ebola and SARS, to prevent parasitic diseases like malaria and against bacteria like multidrug-resistant *S. aureus* (MRSA) and multidrug-resistant tuberculosis. Importantly, it is not the intention of the present invention to use a peptide of the invention to induce protective immunity against tetanus. Rather, the peptides of the invention are used in subjects with pre-existing immunity against tetanus in the form of circulating anti-TTd or anti-TTx antibodies that bind, preferably strongly bind, the peptides of the invention. The peptides of the invention are used in subjects with pre-existing immunity against tetanus for delivery of immunogens and/or vehicles comprising an immunogen to antigen presenting cells (APC) in order to induce and/or enhance immunity against the immunogen in the subject.

The immunogen in the conjugate of the invention may be a peptide, protein fragment, protein, carbohydrate and/or a combination thereof. In one embodiment of the invention the immunogen is a peptide, referred to herein as an immunogenic peptide, to distinguish from the peptide that binds to anti-TTd or anti-TTx antibodies (a TTd-antibody binding peptide).

An immunogenic peptide of the invention is used for inducing and/or enhancing an immune response, preferably a T cell response, elicited by a T cell epitope within a immunogenic peptide of the invention. A preferred T-cell response induced and/or enhanced by an immunogenic peptide of the invention comprise at least one of an HLA class I restricted CTL response and an HLA class II restricted Th response. More preferably the T-cell response consists of both an HLA class I restricted CTL response and simultaneously an HLA class II restricted Th response, and may be advantageously accompanied by a B-cell response.

In one embodiment, an immunogenic peptide of the invention comprises at least a HLA class I epitope and a HLA class II epitope, and/or the at least a HLA class I epitope and a HLA class II epitope are administered together on at least two different immunogenic peptides. Several publications have demonstrated that $CD4^+$ T-cells upon interaction with class II epitope presenting dendritic cells (DC) upregulate CD40 ligand. The interaction of the $CD4^+$ Th cell by its CD40 ligand with the CD40 molecule on the DC leads to activation of the DC. Activated DCs display upregulated costimulatory molecules and secrete CTL-promoting cytokines. This not only allows a more robust $CD8^+$ CTL response induced by such an activated DC that presents MHC class I restricted epitopes, but also a much more robust CTL memory response (Ridge et al. 1998, Nature 393:474; Schoenberger et al. 1998, Nature 393:480; Sun et al. 2004, Nat. Immunol. 5:927). The need for CD40 expression on DC for robust anti-tumour $CD8^+$ CTL responses following vaccination with long (35 aa.) peptides was published in Zwaveling et al. (2002, J. Immunol. 169:350). Recently it was found that without the induction of $CD4^+$ Th responses by MHC class II epitopes contained in the long peptides, the induced $CD8^+$ CTL responses are less vigorous and short lived, completely lacking $CD8^+$ CTL memory.

In one embodiment, an immunogenic peptide of the invention comprises more than one HLA class I epitope and/or more than one HLA class II epitope, and/or the more than one HLA class I epitope and/or the more than one HLA class II epitope are administered together on at least two different immunogenic peptides. In case more than one HLA class I epitope and/or more than one HLA class II epitope are present in an immunogenic peptide of the invention (or administered on at least two different immunogenic peptides), the various different epitopes can be each from one and the same source antigen, or they can be from more than one different source antigen. In case they are from more than one different source antigen, the various antigens can be each from one and the same pathogen or the same tumour/tumour cell, or they can be from more than one different pathogen or from more than one tumour/tumour cell. Antigens from infectious agents (pathogens) or tumour cells from which HLA class I epitopes and/or HLA class II epitopes may be derived for use in a immunogenic peptide of the invention are described herein below.

HLA class I presented cytotoxic T lymphocyte (CTL) epitopes as well as HLA class II T helper epitopes are produced intracellularly, by a sequence of defined intracellular mechanisms. First, the dominant event that defines a T cell epitope is the release of the epitope (or epitope-precursor) from its flanking protein regions in the immunogenic peptides of the invention through enzymatic digestion by cytosolic peptidases. Various peptidases, cytosolic and/or non-cytosolic peptidases (e.g. ER peptidases) can be involved in the proteolytic release of the epitope from its flanking regions in the immunogenic peptide. One such cytosolic peptidases includes e.g. the multicatalytic proteasome (Rock et al., 2004, Nat. Immunol. 5:670), which may be involved in the generation of the N- as well as the C-terminus of CTL epitopes. In particular the proteasome is often involved in the generation of the exact C-terminus of CTL epitopes. The generation of the amino-terminus of a T cell epitope is somewhat flexible because several amino-terminal exo-peptidases (like ERAP1, puromycin sensitive aminopeptidase, bleomycin hydrolase and others) reside in the cytosol and endoplasmic reticulum (ER) and those trimming enzymes have the capacity to shorten an N-terminal elongated epitope-precursor to its precise length. Other peptidase involved in the processing of epitopes from immunogenic peptides include e.g. nardilysin. The generation of the C-terminus of a T cell epitope may be somewhat flexible because the cytosolic thimet oligopeptidase (TOP) (EC 3.4.24.15) has the capacity to shorten an C-terminal elongated epitope-precursor to its precise length by releasing 3-5 amino acids.

In one embodiment, an immunogenic peptide of the invention comprises two or more epitopes as described above arranged as beads-on-string, whereby the epitopes (the beads) are linked directly together and/or are linked through linker sequences. The amino acid sequences flanking or linking the peptides/epitopes preferably comprise proteolytic cleavage sites as described herein. Spacer amino acid sequences flanking or linking the epitopes in the immunogenic peptides of the invention do not need to be present in cases where the proteolytic cleavage site is part of the epitope. However, in other instances spacer amino acid sequences, that do or do not comprise one or more proteolytic cleavage sites, may have a length of 2, 3, 4, 5, 6, 8, 10, 12, 15 or more amino acids. The amino acid sequence of the spacer may or may not be contiguous with the amino acid sequence naturally flanking the epitope in its source antigen.

In a further embodiment of the immunogenic peptides of the invention, the immunogenic peptide comprises an amino acid sequence that does not naturally occur, i.e. that does not exist in nature but that is the result of human intervention and/or design. In this embodiment, an immunogenic peptide will comprise one or more HLA class I epitopes and/or HLA class II epitopes as defined above, whereby such an epitope preferably consists of naturally amino acid sequences of antigens from infectious agents and/or tumours. However, at least one amino acid sequence in the immunogenic peptide that flanks at least one epitope in the immunogenic peptide and/or that links two epitopes in the immunogenic peptide is not from the (naturally occurring or wild type) antigen from which the epitope(s) are derived and/or the linking/flanking amino acid sequence is from other locations within the antigen that are not contiguous with the epitope they flank. In a preferred embodiment the linking/flanking amino acid sequence in a immunogenic peptide of the invention comprise one or more of the protease cleavage motifs as described above. Thus in accordance with the invention (vaccine) immunogenic peptides for inducing a T cell response can be composed comprising one or more HLA class I epitopes and/or HLA class II epitopes, which epitopes may be flanked by and linked together by amino acid sequences comprising protease cleavage motifs as described that will direct efficient proteolytic release of the epitopes from the immunogenic peptides for presentation of the epitopes at the cell surface in the appropriate class I or II MHC molecules.

In a further embodiment the immunogenic peptide of the invention is a synthetic peptide. The use of relatively short peptides is highly preferred for medical purposes as these can be synthesized in vitro efficiently, which is not possible or uneconomical for native proteins larger than about 100 amino acids. Chemical synthesis of peptides is routine practice and various suitable methods are known to the skilled person. In one aspect the invention thus also relates to a method for producing an immunogenic peptide of the invention by chemical synthesis or production in a recombinant host cell. Chemical synthesis of peptides also overcomes the problems associated with recombinant production of intact proteins, which is difficult to standardize and requires extensive purification and quality control measures. Immunogenic peptides with a length that exceeds the length of HLA class I and/or class II epitopes (e.g. having a length as indicated below herein) are particularly advantageous for use as vaccine component because they are large enough to be taken up by professional antigen presenting cells, in particular DC, as explained in WO02/070006 and processed in the DC before cell surface presentation of the contained HLA class I and class II epitopes takes place. Therefore, the disadvantageous induction of T cell tolerance by the systemic presentation of minimal HLA class I epitopes on non-antigen presenting cells (as shown in Toes et al., 1996, Proc. Natl. Acad. Sci. U.S.A 93:7855 and Toes et al., 1996, J. Immunol. 156:3911), is prevented by the application of immunogenic peptides of the invention having a length as indicated herein (as shown in Zwaveling et al., 2002, J. Immunol. 169:350). For the sake of clarity, a immunogenic peptide of the invention preferably comprises at least one of an HLA class I presented epitope and an HLA class II presented epitope. Each of these epitopes are presentable and will bind to the corresponding specific HLA molecule present on the cells after having been processed as described herein. Each HLA epitope may therefore also be named a HLA binding and/or presentable epitope. The length of a immunogenic peptide and/or a synthetic immunogenic peptide of the invention preferably is at least 19, 20, 21, 22, 25, 27, 30, 33, 35, 40 or 45 amino acids and preferably no more than 100, 80, 60, 50 amino acids.

The TTd-antibody binding peptides of the invention in the conjugates of the invention may be conjugated directly to the immunogens, or alternatively, the TTd-antibody binding peptides may be conjugated to pharmaceutically acceptable nanocontainers (vehicle) that comprises the immunogens. In such conjugates, the immunogens may e.g. be encapsulated within nanocontainers, such as nanoparticles, virosomes, liposomes or nanogels, whereby the TTd-antibody binding peptide is preferably conjugated coupled to such a nanocontainer. Such conjugation to the nanocontainer may be either directly or via any of the well-known polymeric conjugation agents such as sphingomyelin, polyethylene glycol (PEG) or other organic polymers. Details of producing such pharmaceutical compositions comprising targeted (PEG) liposomes are described in U.S. Pat. No. 6,372,250. Thus, in a preferred embodiment a conjugate according to the invention is a conjugate wherein the pharmaceutically acceptable vehicle or carrier comprises at least one of: a carrier protein, a nanocontainer, a liposome, a polyplex system, a lipoplex system, and, polyethyleneglycol.

A large variety of methods for conjugation of TTd-antibody binding peptides of the invention with an immunogen or a vehicle comprising an immunogen are known in the art. Such methods are e.g. described by Hermanson (1996, Bioconjugate Techniques, Academic Press), in U.S. Pat. No. 6,180,084 and U.S. Pat. No. 6,264,914 and include e.g. methods used to link haptens to carrier proteins as routinely used in applied immunology (see Harlow and Lane, 1988, "Antibodies: A laboratory manual", Cold Spring Harbor Laboratory Press, Cold Spring Harbor, N.Y.). It is recognised that, in some cases, a TTd-antibody binding peptide or immunogen may lose efficacy or functionality upon conjugation depending, e.g., on the conjugation procedure or the chemical group utilised therein. However, given the large variety of methods for conjugation the skilled person is able to find a conjugation method that does not or least affects the efficacy or functionality of the entities to be conjugated. Suitable methods for conjugation of a peptide with an immunogen or vehicle include e.g. carbodiimide conjugation (Bauminger and Wilchek, 1980, Meth. Enzymol. 70: 151-159). Alternatively, an immunogen or vehicle can be coupled to a TTd-antibody binding peptide as described by Nagy et al., Proc. Natl. Acad. Sci. USA 93:7269-7273 (1996); and Nagy et al., Proc. Natl. Acad. Sci. USA 95:1794-1799 (1998), each of which is incorporated herein by reference. Other methods for conjugating that may suitable be used are e.g. sodium periodate oxidation followed by reductive alkylation of appropriate reactants and glutaraldehyde crosslinking Other convenient ways for crosslinking are chemical coupling via a Staudinger ligation, via Staudinger-Bertozzi ligation, via chemical ligation using a thioester, via [2+3]-Huisgen cycloaddition (click chemistry), via disulfide bridging, and the like. A particularly advantageous method of conjugation may be applied when not only the TTd-antibody binding peptide but also the immunogen or vehicle is a (poly)peptide. In such instances the two entities may be synthesised as a single (poly)peptide chain comprising the amino acid sequences of both the TTd-antibody binding peptide and the immunogen peptide or vehicle. In addition to covalent bonding, in a conjugate according to the invention the immunogen or vehicle may also be directly conjugated to the TTd-antibody binding peptide molecule by non-specific or specific protein-protein interaction, non-covalent bonding and/or coordinating chemical bonding, which conjugation may optionally be effected via a spacer or linker that is bound to the immunogen or vehicle and the TTd-antibody binding peptide.

In a preferred embodiment, a conjugate according to the invention comprises 1-20, more preferably at least 2, 3, 4, 5, 6, 7, 8, 9, 10 and less than 20, 19, 18, 17, 16, 15, 14, 13, 12, 11, 10 peptides that are bound to the antigen, immunogen or the vehicle comprising an antigen or immunogen. More preferably, the conjugate comprises 2-20, more preferably 2-15, 2-10, 2-5, most preferably 3 or 4 peptides that are bound to an antigen, immunogen or the vehicle comprising an antigen or immunogen. In case the conjugate comprises a vehicle comprising an antigen or immunogen and a peptide, the number of peptides can be much higher than 20, for example more than 100, 200, 300, 400, 500, preferably less than 800, 700, 600.

A conjugate of the invention consisting primarily of peptides is preferably soluble in physiologically acceptable watery solutions (e.g. PBS) comprising no more than 60, 50, 40, 35, 20, 10, 5 or 0% DMSO. In such a solution, a conjugate is preferably soluble at a concentration of at least 0.5, 1, 2, 4, or 8 mg conjugate per ml. Alternatively, a mixture of more than one different conjugates of the invention are soluble at a concentration of at least 0.5, 1, 2, 4, or 8 mg peptide per ml in such solutions.

Prophylactic and Therapeutic Use

In another aspect, the present invention relates to a conjugate according to the invention for use as a medicament. More preferably, the present invention relates to a conjugate as defined above for use as a medicament in a subject who has antibodies against tetanus toxin or tetanus toxoid.

In a preferred embodiment, a medicament according to the invention is a prophylactic or therapeutic vaccine, more preferably a prophylactic or therapeutic vaccine against an infectious disease or a cancer.

In a more preferred embodiment, the medicament is for antibody mediated antigen-targeting as is further defined above.

In yet another aspect the present invention relates to a conjugate according to the invention, for use in the prevention or treatment of cancer or an infectious disease in a subject. According to this aspect, the invention also relates to use of a conjugate according to the invention for the manufacture of a medicament for the prevention or treatment of cancer or an infectious disease in a subject.

Thus an immunogen in a conjugate of the invention may comprise HLA class I and/or class II epitopes from a wide range of antigens of tumour and pathogens (infectious agents). E.g. tumour antigens such as MAGE, BAGE, RAGE, GAGE, SSX-2, NY-ESO-1, CT-antigen, CEA, PSA, p53, XAGE and PRAME but also virally induced malignancies, comprising Human papilloma virus (HPV), Kaposi sarcoma herpes virus (KSHV), Epstein Bar virus induced lymphoma's (EBV). Other examples of tumour antigens from which epitopes for use in the present invention may be derived are various ubiquitously expressed self-antigens that are known to be associated with cancer, which include e.g. p53, MDM-2, HDM2 and other proteins playing a role in p53 pathway, molecules such as survivin, telomerase, cytochrome P450 isoform 1B1, Her-2/neu, and CD19 and all so-called house hold proteins. Cancers that may be treated in accordance with the present invention are selected among the following list: lung, colon, esophagus, ovary, pancreas, skin, gastric, head and neck, bladder, sarcoma, prostate, hepatocellular, brain, adrenal, breast, endometrial, mesothelioma, renal, thyroid, hematological, carcinoid, melanoma, parathyroid, cervix, neuroblastoma, Wilms, testes, pituitary and pheochromocytoma cancers.

In addition, an immunogen in a conjugate of the invention may comprise HLA class I and/or class II epitopes from antigens from pathogens and infectious agents such as viruses, bacteria, fungi and protozoa. Some examples of pathogenic viruses causing infections or tumours from which epitopes from antigens may be derived include: hepatitis (A, B, or C), herpes virus (e.g., VZV, HSV-I, HAV-6, HSV-II, and CMV, Epstein Barr virus), adenovirus, SV40 virus (causing mesothelioma), influenza virus, flaviviruses, echovirus, rhinovirus, coxsackie virus, coronavirus, respiratory syncytial virus (RSV), mumps virus, rotavirus, measles virus, rubella virus, parvovirus, vaccinia virus, HTLV virus, dengue virus, molluscum virus, poliovirus, rabies virus, JC virus, arboviral encephalitis virus, and human immunodeficiency virus (HIV virus; e.g., type I and II), Human Papilloma Virus (HPV) infections, more in particular of the high tumour risk types of HPV, comprising HPV-16, 18, 31, 33, 35, 39, 45, 51, 52, 56, 58, 59, and 68 types. Some examples of pathogenic bacteria causing infections from which epitopes from antigens may be derived include: *Listeria, Escherichia, Chlamydia, Rickettsial bacteria, Mycobacteria, Staphylococci, Streptocci, Pneumonococci, Meningococci, Gonococci, Klebsiella, Proteus, Serratia, Pseudomonas, Legionella, Diphtheria, Salmonella, Bacilli*, bacteria causing Cholera, Tetanus, Botulism, Anthrax, Plague, Leptospirosis, and Lymes disease. Some examples of pathogenic fungi causing infections from which epitopes from antigens may be derived include: *Candida* (e.g., *albicans, krusei, glabrata, tropicalis*), *Cryptococcus neoformans, Aspergillus* (e.g., *fumigatus, niger*), fungi of the genus *Mucorales* (*Mucor, Absidia, Rhizopus*), *Sporothrix schenkii, Blastomyces dermatitidis, Paracoccidioides brasiliensis, Coccidioides immitis* and *Histoplasma capsulatum*. Some examples of pathogenic parasites causing infections from which epitopes from antigens may be derived include: *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii* and *Plasmodium falciparis*.

In a preferred embodiment, the subject has antibodies against tetanus toxin or tetanus toxoid.

Alternatively or in combination with an other embodiment, in a preferred embodiment of the invention the medicament is a prophylactic or therapeutic vaccine.

Alternatively or in combination with an other embodiment, in a preferred embodiment of the invention the method further comprises administering a vaccine to induce an immune response to tetanus toxoid. Preferably, the vaccine to induce an immune response to tetanus toxoid is administered at least 1, 2, 3, 4, 5, 6, 7, 8, 9, 10, 20, 30 or more weeks prior to administering the conjugate. Preferably, the vaccine is TTd.

In another embodiment the conjugate is premixed with TETAQUIN® to form immune complexes and subsequently administered.

In the case of a vaccination trial, pre-treatment of subjects by TTd immunization to increase antibody levels against In a preferred embodiment the medicament is for antibody mediated antigen-targeting as is defined above.

In a further aspect, the present invention also relates to a method of treating or preventing of cancer or an infectious disease, comprising the steps of administration to a subject in need thereof an effective amount of a conjugate according to the invention.

In a preferred embodiment the subject to be treated has antibodies against tetanus toxin or tetanus toxoid.

In a more preferred embodiment, the conjugate is administered together with a pharmaceutically acceptable carrier. Pharmaceutically acceptable stabilizing agents, osmotic agents, buffering agents, dispersing agents, and the like may also be incorporated into the pharmaceutical compositions comprising the conjugates of the invention. The preferred form depends on the intended mode of administration and therapeutic application, preferably parenteral. The pharmaceutical carrier can be any compatible, non-toxic substance suitable to deliver the conjugate to a subject. Pharmaceutically acceptable carriers for parenteral delivery are exemplified by sterile buffered 0.9% NaCl or 5% glucose optionally supplemented with a 20% albumin. Preparations for parental administration must be sterile. The parental route for administration of the conjugate is in accord with known methods, e.g. injection or infusion by intravenous, intraperitoneal, intramuscular, intraarterial or intralesional routes. A conjugate according to the invention is preferably administered by bolus injection. A typical pharmaceutical composition for intramuscular injection would be made up to contain, for example, 1-10 ml of phosphate buffered saline and 1 to 100 µg, preferably 10 to 300 µg (of antigen protein) of conjugate of the present invention. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety).

In a further embodiment, a pharmaceutical composition according to the invention further comprises at least one immune response stimulating compound or adjuvant. Advantageously, a pharmaceutical composition according to the invention may additionally comprise one or more synthetic adjuvants. These adjuvants may be admixed to a pharmaceutical composition according to the invention or may be administered separately to the mammal or human to be treated. Particularly preferred are those adjuvants that are known to act via the Toll-like receptors. Immune modifying compounds that are capable of activation of the innate immune system, can be activated particularly well via Toll like receptors (TLR's), including TLR's 1-10 and/or via a RIG-1 (Retinoic acid-inducible gene-1) protein and/or via an endothelin receptor. Compounds capable of activating TLR receptors and modifications and derivatives thereof are well documented in the art. TLR1 may be activated by bacterial lipoproteins and acetylated forms thereof, TLR2 may in addition be activated by Gram positive bacterial glycolipids, LPS, LPA, LTA, fimbriae, outer membrane proteins, heat-shock proteins from bacteria or from the host, and Mycobacterial lipoarabinomannans. TLR3 may be activated by dsRNA, in particular of viral origin, or by the chemical compound poly(I:C). TLR4 may be activated by Gram negative LPS, LTA, Heat shock proteins from the host or from bacterial origin, viral coat or envelope proteins, taxol or derivatives thereof, hyaluronan containing oligosaccharides and fibronectins. TLR5 may be activated with bacterial flagellae or flagellin. TLR6 may be activated by mycobacterial lipoproteins and group B *Streptococcus* heat labile soluble factor (GBS-F) or *Staphylococcus* modulins. TLR7 may be activated by imidazoquinolines. TLR9 may be activated by unmethylated CpG DNA or chromatin—IgG complexes. In particular TLR3, TLR7 and TLR9 play an important role in mediating an innate immune response against viral infections, and compounds capable of activating these receptors are particularly preferred for use in a method of treatment and in a composition or a medicament according to the invention. Particularly preferred adjuvants comprise, but are not limited to, synthetically produced compounds comprising dsRNA, poly(I:C), unmethylated CpG DNA which trigger TLR3 and TLR9 receptors. IC31, IMSAVAC® (TLR4 agonist adjuvant), MONTANIDE® ISA-51 (an oil-in-water emulsion adjuvant produced by Seppic 7, France). Another preferred immune modifying compound is a T cell adhesion inhibitor, more preferably an inhibitor of an endothelin receptor such as BQ-788 (Buckanovich R J et al., Ishikawa K, PNAS (1994) 91:4892). BQ-788 is N-cis-2,6-dimethyl-piperidinocarbonyl-L-gamma-methylleucyl-D-1-methoxycarbonyltryptophanyl-D-norleucine. However any derivative of BQ-788 or modified BQ-788 compound is also encompassed within the scope of this invention. In another preferred embodiment, a synthetic adjuvant compound is physically linked to a peptide or immunogenic peptide of the invention. Physical linkage of adjuvants and costimulatory compounds or functional groups, to the HLA class I and HLA class II epitope comprising peptides provides an enhanced immune response by simultaneous stimulation of antigen presenting cells, in particular dendritic cells, that internalize, metabolize and display antigen.

Preferably, the conjugate is a prophylactic or therapeutic vaccine.

Alternatively, or in combination with one or more other embodiments, in an embodiment of the invention the method of treatment further comprises administering a vaccine to induce an immune response against tetanus toxoid at least 1, 2, 3, 4, 5, 6, 7, 8, 9, 10, 20, 30 or more weeks prior to administering the conjugate. Preferably, the vaccine is TTd.

Preferably, a subject who has antibodies against tetanus toxin or tetanus toxoid has been immunized with tetanus toxoid, has had post-exposure prophylaxis for tetanus and/or has suffered from tetanus.

Alternatively or in combination with other embodiments of the invention, the method of treatment of cancer according to the invention may further comprise other methods of treatment. Examples of other methods of treatment that may be combined with the method of treatment according to the invention are for instance chemo-therapy, radiation therapy (also known as radiotherapy, X-ray therapy, irradiation) and/or surgery. The skilled person in the art, typically a Doctor of Medicine, will know what methods of treatment are suitable in a specific situation.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

DESCRIPTION OF THE FIGURES

FIG. 1. Schematic scheme of antibody-mediated antigen-targeting. Please note that the level of multimerization (three-fold) is just an illustration.

FIGS. 5a-5n show the results of the individual sera 034758, 034773, 033994, 034986 mixture was stirred over night and concentrated in vacuo. The remaining residue was taken up in toluene and a byproduct crystallized upon standing at −20° C. over night. The mother liquor was concentrated in vacuo and taken up in Et$_2$O and a second byproduct crystallized upon standing at −20° C. over night. The mother liquor was concentrated in vacuo. Column chromatography (Tol-EA 100-0→98-2) afforded the title compound as a slightly yellow oil (76.6 g, 52% and 80 g of not pure product). ($R_F$: PE-EA 80-20=0.53), $^1$H NMR (400 MHz, CDCl$_3$): δ=3.35 (s, 2H, CH$_2$ CH$_2$OTr), 3.57 (d, 2H, J=10.8 Hz, CH$_2$ CH$_2$Br), 3.66 (d, 2H, J=10.8 Hz, CH$_2$ CH$_2$Br), 3.95 (s, 2H, CH$_2$ CH$_2$NPhth), 7.22-7.31 (m, 9H, H arom), 7.24-7.44 (m, 6H, H arom), 7.71-7.73 (m, 2H, H arom), 7.83-7.86 (m, 2H, H arom). $^{13}$C NMR (100 MHz, CDCl$_3$): δ=37.2 (CH$_2$ CH$_2$Br), 41.3 (CH$_2$ CH$_2$NPhth), 43.8 ($C_q$ CC$_4$H$_8$), 64.9 (CH$_2$ CH$_2$OTr), 87.3 ($C_q$ OTr), 123.4 (CH arom), 127.2 (CH arom), 127.9 (CH arom), 128.2 (CH arom), 128.8 (CH arom), 131.9 ($C_q$ arom), 134.1 (CH arom), 143.2 ($C_q$ arom), 168.7 (C=O Phth).

2,2-bis-azidomethane-1-phthalimido-3-(trityloxy)-propane (18)

Figure 2A:
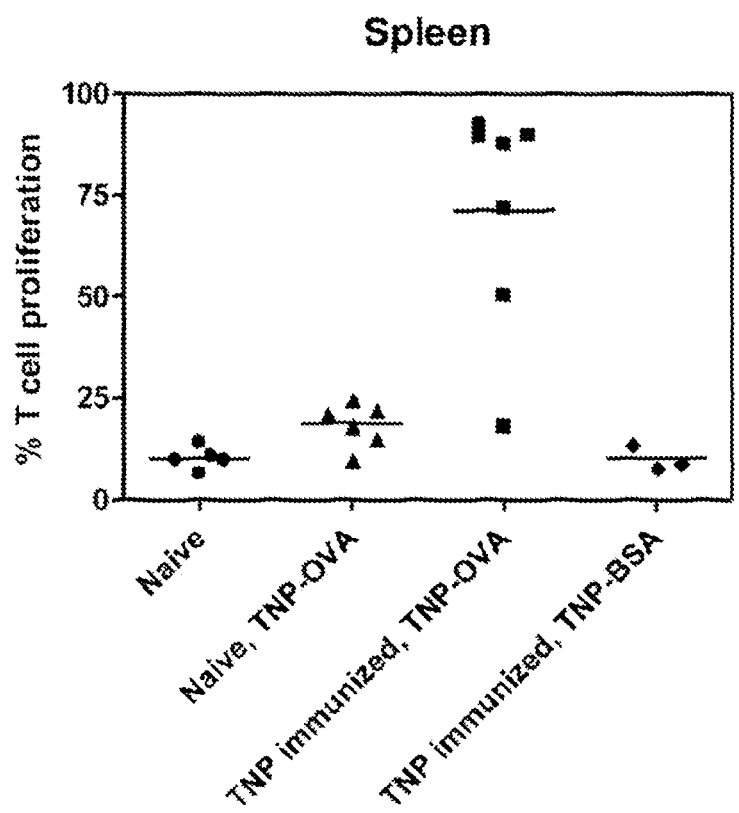
FIGS. 2a and 2b. OVA-specific proliferation of labelled T cells in spleen (FIG. 2a) and lymph nodes (FIG. 2b) of mice. The symbols represent individual mice. Statistical analysis shows that anti-TNP antibody mediated OVA-specific T cell proliferation is significantly different from the other groups: $P<0.001$.

17 (76.6 g, 121 mmol) was dissolved in DMF (1000 ml). To this solution were added NaN$_3$ (39 g, 600 mmol) and LiCl (cat). The mixture was refluxed for 6 hours and concentrated in vacuo. The residue was then taken up in EtOAc and washed with H$_2$O, the organic layer was dried over MgSO$_4$ concentrated in vacuo (66.1 g, 98%). ($R_F$: PE-EA 80-20=0.57), $^1$H NMR (400 MHz, CDCl$_3$): δ=3.13 (s, 2H, CH$_2$ CH$_2$OTr), 3.46 (d, 2H, J=12.4 Hz, CH$_2$ CH$_2$N$_3$), 3.51 (d, 2H, J=12.4 Hz, CH$_2$ CH$_2$N$_3$), 3.76 (s, 2H, CH$_2$ CH$_2$NPhth), 7.22-7.79 (m, 19H, H arom). $^{13}$C NMR (100 MHz, CDCl$_3$): δ=40.2 (CH$_2$ CH$_2$NPhth), 44.4 ($C_q$ CC$_4$H$_8$), 52.9 (CH$_2$ CH$_2$N$_3$), 63.4 (CH$_2$ CH$_2$OTr), 86.9 ($C_q$ OTr), 123.2 (CH arom), 127.2 (CH arom), 127.9 (CH arom), 128.2 (CH arom), 128.8 (CH arom), 131.9 ($C_q$ arom), 134.1 (CH arom), 143.3 ($C_q$ arom), 168.5 (C=O Phth).

1-amino-2,2-bis-azidomethane-3-(trityloxy)-propane (19)

18 (50.1 g, 90 mmol) was taken up in dry EtOH (450 ml) and hydrazine (6.55 ml, 135 mmol) was added under Argon atmosphere. The reaction was stirred for 3 days (during which a solid appeared) until TLC analyses showed complete conversion of the starting material into a lower running spot. The solid was filtered and washed twice with cold EtOH, the combined organic layers were concentrated in vacuo. Column chromatography (PE-EA 75-25→25-75) afforded the title compound as a colorless oil (24.8 g, 64%). ($R_F$: DCM-MeOH 95-5=0.44), $^1$H NMR (400 MHz, CDCl$_3$): δ=2.62 (s, 2H, CH$_2$ CH$_2$NH$_2$), 2.99 (s, 2H, CH$_2$ CH$_2$OTr), 3.38 (s, 4H, CH$_2$ CH$_2$N$_3$), 7.13-7.43 (m, 15H, H arom). $^{13}$C NMR (100 MHz, CDCl$_3$): δ=42.1 (CH$_2$ CH$_2$NH$_2$), 44.6 ($C_q$ CC$_4$H$_8$), 52.1 (CH$_2$ CH$_2$N$_3$), 61.4 (CH$_2$ CH$_2$OTr), 86.5 ($C_q$ OTr), 126.9 (CH arom), 127.2 (CH arom), 128.2 (CH arom), 143.4 ($C_q$ arom).

1-(tert-butoxycarbonylamino)-2,2-di-(tert-butoxycarbonylamino)methyl-propan-3-ol (20)

19 (24.8, 58 mmol) was dissolved in THF (580 ml), then H$_2$O (29 ml) and PPh$_3$ (33.3 g, 127.6 mmol) were added. This mixture was stirred over night at room temperature then heated to 50° C. for an additional 6 hours ($R_F$: EtOH t-BuOH H$_2$O AcOH: 4-2-2-1=0.42). The reaction was concentrated in vacuo and taken up in H$_2$O (580 ml) and filtered. To the aqueous solution was added 37% HCl (29 ml, 348 mmol) and stirred for 3 days ($R_F$: EtOH t-BuOH H$_2$O AcOH: 4-2-2-1=0.05). The reaction was concentrated in vacuo and co evaporated 3 times with H$_2$O to remove most of the HCl. The residue was taken up in H$_2$O and washed with DCM. The aqueous layer was concentrated in vacuo. The residue was taken up in H$_2$O (220 ml) and ACN (220 ml) to this solution was added NaOH (3 molar solution in H$_2$O) till pH 7. Then NaOH (60 ml, 176 mmol, 3 molar solution in H$_2$O) and Boc$_2$O (38.4 g, 176 mmol) were added and the mixture was stirred over night. The layers were separated and the aqueous layer was washed 2 times with EtOAc. The organic layers were combined dried over MgSO$_4$ and concentrated in vacuo. Crystallization from PE/EtOAc afforded the title compound as a white solid (12.9 g, 51%). ($R_F$: PE-EA 80-20=0.53), $^1$H NMR (400 MHz, CDCl$_3$): δ=1.45 (s, 27H, CH$_3$ Boc), 2.82 (d, 6H, J=6.8 Hz, CH$_2$ CH$_2$NH), 3.13 (d, 2H, J=4.4 Hz, CH$_2$ CH$_2$OH), 4.32 (t, 1H, J=4.4 Hz, OH), 5.78 (t, 3H, J=6.4 Hz, NH). $^{13}$C NMR (100 MHz, CDCl$_3$): δ=28.3 (CH$_3$ Boc), 39.0 (CH$_2$ CH$_2$NH), 46.1 ($C_q$ CC$_4$H$_8$), 60.3 (CH$_2$ CH$_2$OH), 79.7 ($C_q$ Boc), 157.8 (C=O Boc).

1-(tert-butoxycarbonylamino)-2,2-di-(tert-butoxycarbonylamino)methyl-3-propanoic acid (21)

20 (12.2 g, 28 mmol) was suspended in EtOAc (280 ml), MeCN (280 ml) and H$_2$O (280 ml). To this suspension was added NaIO$_4$ (24.1 g, 113 mmol) and a catalytic amount of RuCl$_3$ which turned from black to orange. When the suspension became clear TLC analyses indicated complete conversion to a lower running spot the organic layer was separated and the water layer washed with EtOAc. To the combined organic layers was added EDTA (104 g, 280 mmol) and stirred over night. The layers were separated and the organic layer was washed with Na$_2$S$_2$O$_3$. The organic layer was dried over MgSO$_4$ and during concentration crystallized affording the title compound as a white solid (8.77 g, 70%). ($R_F$: PE-EA-AcOH 50-50-3 drops=0.77), $^1$H NMR (400 MHz, CDCl$_3$): δ=1.43 (s, 27H, CH$_3$ Boc), 3.25 (d, 6H, J=6.0 Hz, CH$_2$ CH$_2$NH), 5.78 (bs, 3H, NH), 9.59 (vbs, 1H, COOH). $^{13}$C NMR (100 MHz, CDCl$_3$): δ=28.3 (CH$_3$ Boc), 40.31 (CH$_2$ CH$_2$NH), 53.0 ($C_q$ CC$_4$H$_8$), 79.8 ($C_q$ Boc), 157.0 (C=O Boc), 176.5 (C=O COOH).

Boc protected tri-amino-2,2-dimethyl propanoic acid with amino PEG-spacer (22)

To a solution of 21 (0.447 g, 1.0 mmol) in DCM (20 ml) and Et$_3$N (0.21 ml, 1.5 mmol) under argon atmosphere was added HATU (0.380 g, 1.5 mmol), the reaction was stirred for 15 min then and 2-[2-(2-aminoethoxy)ethoxy]ethan-1-amine (1.46 ml, 10 mmol) was added. After stirring over night the mixture was washed with H$_2$O and the organic layer dried over MgSO$_4$ and concentrated in vacuo. Column chromatography (DCM/MeOH 100-0-90-10) afforded the title compound as a colorless oil (0.293 g, 51%). ($R_F$: DCM-MeOH 90-10=0.15), $^1$H NMR (400 MHz, CDCl$_3$): δ=1.44 (s, 27H, CH$_3$ Boc), 2.91 (t, 2H, J=4.8 Hz, CH$_2$ peg), 3.23 (d, 6H, J=6.4 Hz, CH$_2$ scaffold), 3.40 (m, 2H, CH$_2$ peg), 3.46 (bs, 2H, NH$_2$), 3.56 (t, 4H, J=5.2 Hz, peg), 3.63 (bs, 4H, peg), 5.88 (bs, 3H, NH Boc), 7.33 (bs, 1H, NH peg amide); $^{13}$C NMR (100 MHz, CDCl$_3$): δ=28.2 (CH$_3$ Boc), 39.1 (CH$_2$ peg), 41.1 (CH$_2$ scaffold), 52.2 ($C_q$ CC$_4$H$_8$), 69.3 (2×CH$_2$ peg), 70.0 (CH$_2$ peg), 70.1 (CH$_2$ peg), 72.1 (CH$_2$ peg), 79.6 (C$_q$ Boc), 157.0 (C=O Boc), 172.6 (C=O peg amide).

Boc protected tri-amino-2,2-dimethyl propanoic acid with diphenylcyclooctyn PEG spacer (24)

To a solution of 22 (0.383 g, 0.662 mmol) in DMF (13 ml) and Et$_3$N (0.27 ml, 1.98 mmol) under Argon atmosphere was added 23 (0.267 g, 0.695 mmol). After stirring over night the mixture was concentrated in vacuo. Size exclusion chromatography (LH20 MeOH/-DCM 1-1) and subsequent column chromatography (DCM/MeOH 100-0→99-1) afforded the title compound as a colorless oil (0.125 g, 33%). (R$_F$: DCM-MeOH 90-10=0.9); $^1$H NMR (400 MHz, CDCl$_3$): δ=1.44 (s, 27H, CH$_3$ Boc), 2.89 (m, 1H, CH$_2$ octyn), 3.17 (d, 1H, J=13.6 Hz, CH$_2$ octyn), 3.23-3.25 (d, 6H, J=6.8 Hz, CH$_2$ scaffold), 3.40-3.45 (m, 4H, CH$_2$ peg), 3.58-3.60 (m, 4H, CH$_2$ peg), 3.65 (bs, 4H, CH$_2$ peg), 5.50 (bs, 1H, CH octyn), 5.50 (bs, 3H, NH Boc), 5.81 (bs, 1H, NH carbamate), 7.27-7.37 (m, 8H, Harom), 7.52 (d, 1H, J=7.6 Hz, NH peg amide); $^{13}$C NMR (100 MHz, CDCl$_3$): δ=28.3 (CH$_3$ Boc), 39.1 (CH$_2$ peg), 40.9 (CH$_2$ peg), 41.1 (CH$_2$ CC$_4$H$_8$), 46.0 (CH$_2$ octyn), 52.2 (C$_q$ CC$_4$H$_8$), 69.21 (CH$_2$ peg), 69.9 (2×CH$_2$ peg), 70.0 (CH$_2$ peg), 70.3 (CH$_2$ peg), 76.6 (CH octyn), 79.8 (C$_q$ Boc), 109.9 (C$_q$ Arom), 112.8 (C$_q$ Arom), 121.2 (C$_q$ Arom), 123.7-129.8 (CH arom), 151.1, 152.2, 155.5, 157.0 (C=O Boc), 172.6 (C=O peg amide).

Maleimide Propionyl Functionalyzed Tri-Amino-2,2-Dimethyl Propanoic Acid Linker with Diphenylcyclooctyn PEG Spacer (26)

Compound 24 (38 mg, 0.047 mmol) was dissolved at 0° C. under argon in 4M HCl in dioxane (0.47 ml, 1.88 mmol). The mixture was allowed to warm to room temperature. After LCMS analysis (LCMS: 1090: 13.5 min, R$_F$: 6.52 min) showed complete conversion to the tri-amine (6 h) the mixture poured in Et$_2$O at 0° C. and subsequently spinned off. The Et$_2$O was decanted and the residue was taken up in DCM (0.1M). To this suspension was added maleimide propanoic acid OSu ester 25 (0.05 g, 0.188 mmol) and Et$_3$N (19 µl, 0.188 mmol). After LCMS analysis (LCMS: 1090: 13.5 min, R$_F$: 7.56 min) showed completion of the reaction the mixture was directly purified using column chromatography (DCM/MeOH 100-0→96-3) affording the title compound as a yellow oil (0.0124 g, 27%). (R$_F$: DCM-MeOH 90-10=0.4); $^1$H NMR (400 MHz, CDCl$_3$): δ=1.26 (bs, 6H), 2.54 (bs, 6H), 3.19-3.45 (m, 6H), 3.58-3.82 (m, 14H), 5.47 (s, 1H), 6.71 (s, 6H), 7.29 (s, 8H); $^{13}$C NMR (100 MHz, CDCl$_3$): δ=29.6, 34.2, 34.8, 39.2, 39.7, 40.9, 46.1, 50.9, 53.4, 69.0, 69.9, 70.17, 76.6, 109.8, 112.8, 121.2, 123.7, 125.8, 126.1, 126.9, 127.6, 127.8, 128.0, 129.9, 134.2, 150.9, 155.5, 170.4, 171.7, 172.2.

1.3.2 Synthesis of Construct 33

Figure 7:
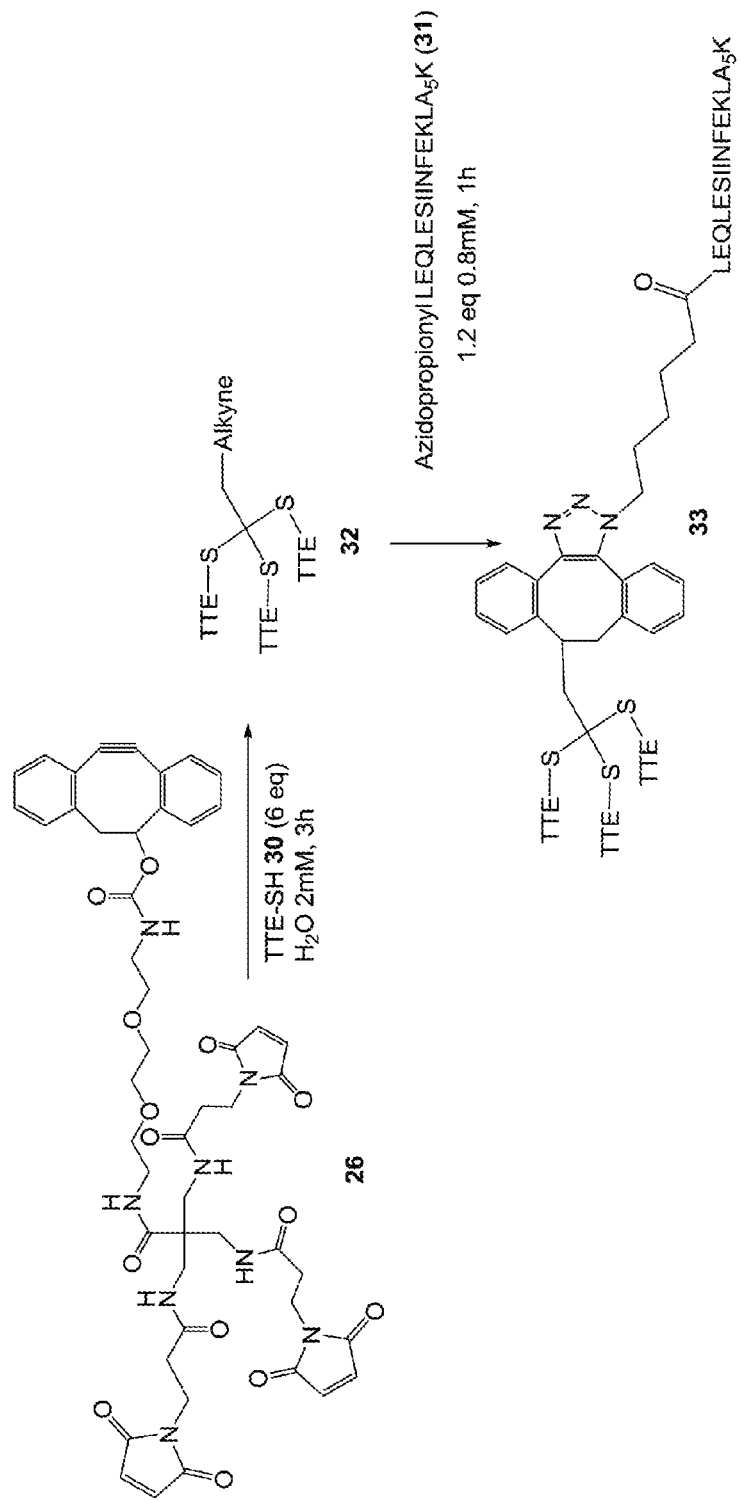

See FIG. 7 for Synthetic Scheme for synthesis of construct 33.

(TTE-SH) (30)

(SEQ ID NO: 217)
F-I-G-I-T-E-L-K-K-L-E-S-K-I-N-K-V-F-A-A-K-Y-A-R-V-R-A-K-C

Peptide 30 was synthesized using solid phase peptide synthesis on a Tentagel S Ac resin (Rapp, Tübingen). Normal couplings (1.5 h) were performed using Fmoc amino acids carrying acid labile side chain protection (were required). Activation was performed with PyBop and NMM. Fmoc deprotection was performed with 20 vol % piperidine in NMP. Washings were performed with NMP. Cleavage from the resin and side chain deprotection was performed with TFA containing 5% water and 2% triethylsilane. Purification was performed with rpHPLC. Analysis of the purified peptide was performed with UPLC-MS (Acquity, Waters).

(OVAE) (31)

(SEQ ID NO: 217)
Azidohexanoyl-L-E-Q-L-E-S-I-I-N-F-E-K-L-A-A-A-A-A-K

Peptide 31 was synthesized similarly to peptide 30. The azidohexanoyl group was introduced using a coupling with azidohexanoic acid/PyBop/NMM. Cleavage from the resin and side chain deprotection was performed with TFA containing 5% water.

Construct 33

Figure 8:
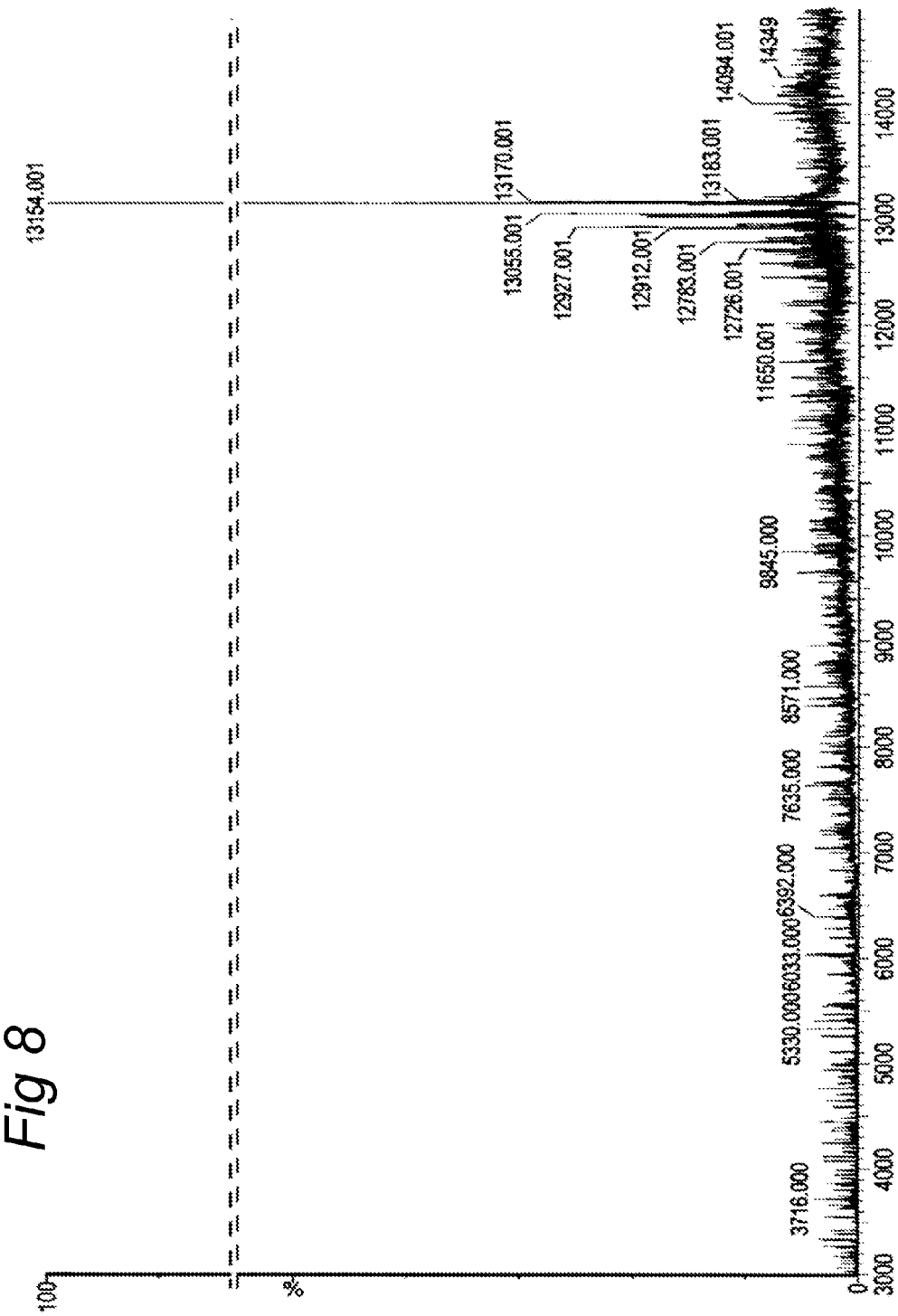
Figure 9A:
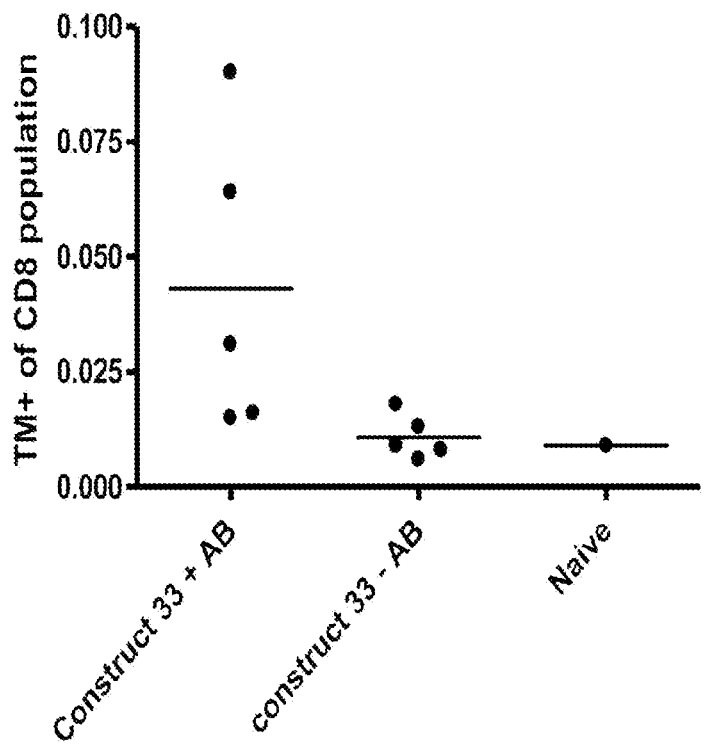
Figure 9B:
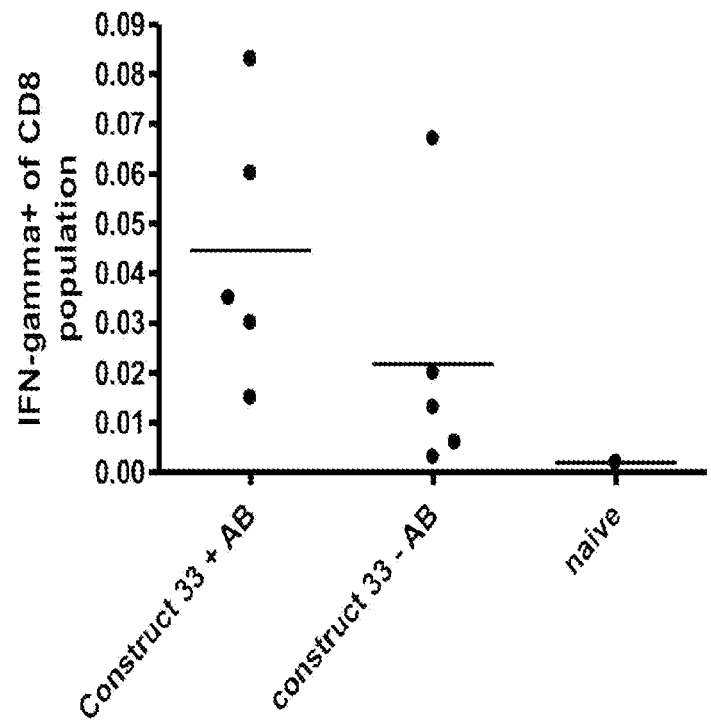

TTE peptide 30 (4.8 mg, 1.44 µmol) was dissolved in degassed H$_2$O (800 µl, millipore) under argon atmosphere, the pH was set to 6 by addition of NaHCO$_3$ (0.5 M, 20 µl, degassed). To this solution 26 (0.234 mg, 0.24 µmol) in MeCN (23 µl) was added. This mixture was stirred 3 h after which mass spectrometry (QTof) showed complete conversion of 26 into 32. In addition TTE-SH and the related disulfide TTE-S-S-ETT were observed, resulting from the excess TTE-SH that had been used. To this mixture was added peptide OVAE (31, 0.63 mg, 0.289 µmol) in DMSO (400 µl, millipore). In 1 hour 32 was converted to 33 according to mass spectrometry (Qtof). The mixture was purified by HPLC yielding 2.7 mg, 0.20 µmol, 83%. The product was analyzed by mass spectrometry and the expected mass was observed (see FIG. 8 for deconvoluted mass spectrum, MW$_{calc}$=13,153.1, MW$_{obs}$=13,154.0).

2. Results 2.1. Systemic Antigen-Specific T Cell Priming in Mice

Mice were repeatedly immunized with TNP-BSA resulting in high titers of circulating antibodies against the hapten TNP (TNP immunized) or left non-immunized (naïve).

Figure 2B:
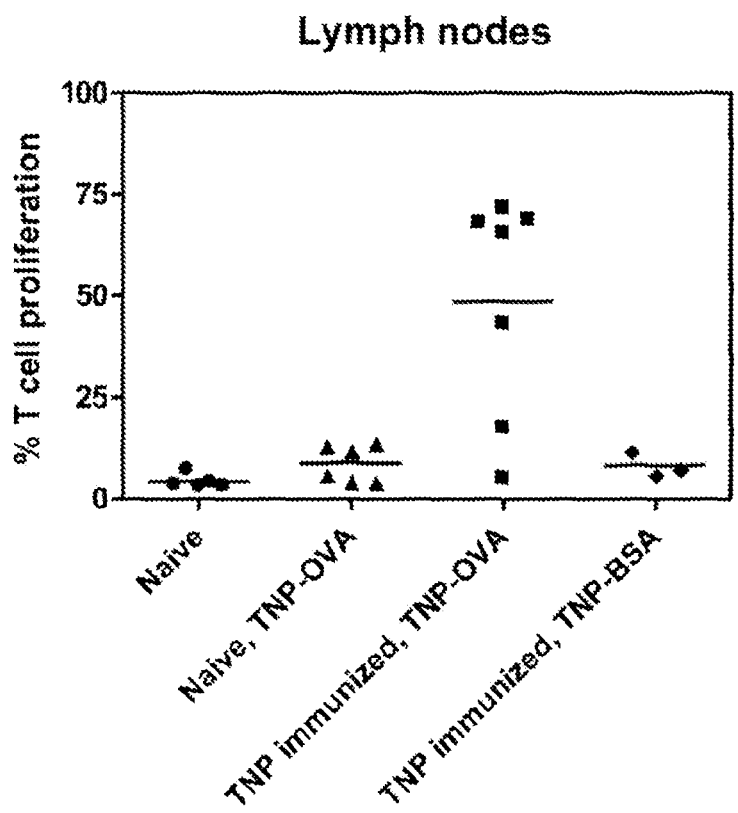

After 1-2 months all mice were injected with naïve OVA-specific CD8 T cells which were labelled with the fluorescent dye CFSE. After 24 hrs the mice were injected with a single dose of TNP-OVA. 3 days later the mice were sacrificed and OVA-specific proliferation of the labelled T cells was analysed in spleen and lymph nodes by flow cytometry (FIGS. 2a and 2b). The symbols represent individual mice. Statistical analysis shows that anti-TNP antibody mediated OVA-specific T cell proliferation is significantly different from the other groups: P<0.001. Thus, systemic antigen-specific T cell priming can be facilitated by pre-existing circulating antibodies against hapten-epitopes.

2.2. Synthetizing TTx Overlapping Peptides

Since humans do not have circulating antibodies against TNP and since it is not desired to immunize humans in order to get circulating anti-TNP antibodies, the inventors selected a pathogen against which most humans do have circulating antibodies. The inventors synthesized TTx alfa and beta chain in overlapping peptides (22 amino acids in length, 10 amino acids overlap). For this study 109 peptides were made by means of solid phase synthesis. The peptides were synthesized with a C-terminal Lys(biotin) connected to the peptide via a Ahx spacer (amino hexanoic acid). These biotin peptides can be bound to a streptavidin ELISA plate for analysis. Peptides were screened in ELISA for binding antibodies in TETAQUIN®. TETAQUIN® is a mixture of antibodies of a large panel of blood-donors that all have high titers of anti-TTd antibodies. TETAQUIN® exists for 90% of human IgG (100-180 mg/ml) and is available from Sanquin (Amsterdam, The Netherlands). Elisa's were performed in which the biotinylated peptides are individually attached to streptavidin-coated Elisa plates. For each peptide a concentration series of TETAQUIN® was tested for binding. In this fashion the best binding peptides were identified. Results are expressed as OD from the ELISA. This is no absolute figure, is just used to discriminate between different peptides in one test. The skilled person is aware that OD's may vary between various tests.

TABLE 1

Overlapping peptides TTx alpha and TTx beta chain
Overlapping 22-mer peptides (overlap 10 amino acids) from
TTx α-chain (38 peptides)
TTx β-chain (71 peptides)

| Synthesis number | Working number | Sequence | SEQ ID NO: |
|---|---|---|---|
| 0826-3 | α1 | PITINNFRYSDPVNNDTIIMMEZO | 25 |
| 0826-4 | α2 | VNNDTIIMMEPPYCKGLDIYYKZO | 26 |
| 0826-5 | α3 | YCKGLDIYYKAFKITDRIWIVPZO | 27 |
| 0826-6 | α4 | KITDRIWIVPERYEFGTKPEDFZO | 28 |
| 0826-7 | α5 | YEFGTKPEDFNPPSSLIEGASEZO | 29 |
| 0826-8 | α6 | PSSLIEGASEYYDPNYLRTDSDZO | 30 |
| 0826-9 | α7 | DPNYLRTDSDKDRFLQTMVKLFZO | 31 |
| 0826-10 | α8 | RFLQTMVKLFNRIKNNVAGEALZO | 32 |
| 0827-33 | α9 | IKNNVAGEALLDKIINAIPYLGZO | 33 |
| 0827-34 | α10 | KIINAIPYLGNSYSLLDKFDTNZO | 34 |
| 0827-35 | α11 | YSLLDKFDTNSNSVSFNLLEQDZO | 35 |
| 0827-36 | α12 | SVSFNLLEQDPSGATTKSAMLTZO | 36 |
| 0827-37 | α13 | GATTKSAMLTNLIIFGPGPVLNZO | 37 |
| 0828-1 | α14 | IIFGPGPVLNKNEVRGIVLRVDZO | 38 |
| 0828-2 | α15 | EVRGIVLRVDNKNYFPCRDGFGZO | 39 |
| 0828-3 | α16 | NYFPCRDGFGSIMQMAFCPEYVZO | 40 |
| 0828-4 | α17 | MQMAFCPEYVPTFDNVIENITSZO | 41 |
| 0828-5 | α18 | FDNVIENITSLTIGKSKYFQDPZO | 42 |
| 0828-6 | α19 | IGKSKYFQDPALLLMHELIHVLZO | 43 |
| 0828-7 | α20 | LLMHELIHVLHGLYGMQVSSHEZO | 44 |
| 0828-8 | α21 | LYGMQVSSHEIIPSKQEIYMQHZO | 45 |
| 0828-9 | α22 | PSKQEIYMQHTYPISAEELFTFZO | 46 |
| 0828-10 | α23 | PISAEELFTFGGQDANLISIDIZO | 47 |
| 0828-11 | α24 | QDANLISIDIKNDLYEKTLNDYZO | 48 |
| 0828-12 | α25 | DLYEKTLNDYKAIANKLSQVTSZO | 49 |

TABLE 1-continued

Overlapping peptides TTx alpha and TTx beta chain
Overlapping 22-mer peptides (overlap 10 amino acids) from
TTx α-chain (38 peptides)
TTx β-chain (71 peptides)

| Synthesis number | Working number | Sequence | SEQ ID NO: |
|---|---|---|---|
| 0828-13 | α26 | IANKLSQVTSCNDPNIDIDSYKZO | 50 |
| 0828-14 | α27 | DPNIDIDSYKQIYQQKYQFDKDZO | 51 |
| 0828-15 | α28 | YQQKYQFDKDSNGQYIVNEDKFZO | 52 |
| 0828-16 | α29 | GQYIVNEDKFQILYNSIMYGFTZO | 53 |
| 0828-17 | α30 | LYNSIMYGFTEIELGKKFNIKTZO | 54 |
| 0828-18 | α31 | ELGKKFNIKTRLSYFSMNHDPVZO | 55 |
| 0828-19 | α32 | SYFSMNHDPVKIPNLLDDTIYNZO | 56 |
| 0828-20 | α33 | PNLLDDTIYNDTEGFNIESKDLZO | 57 |
| 0828-21 | α34 | EGFNIESKDLKSEYKGQNMRVNZO | 58 |
| 0828-22 | α35 | EYKGQNMRVNTNAFRNVDGSGLZO | 59 |
| 0828-23 | α36 | AFRNVDGSGLVSKLIGLCKKIIZO | 60 |
| 0828-24 | α37 | KLIGLCKKIIPPTNIRENLYNRZO | 61 |
| 0828-25 | α38 | IGLCKKIIPPTNIRENLYNRTAZO | 62 |
| 0828-26 | β1 | SLTDLGGELCIKIKNEDLTFIAZO | 63 |
| 0828-27 | β2 | IKNEDLTFIAEKNSFSEEPFQDZO | 64 |
| 0828-28 | β3 | NSFSEEPFQDEIVSYNTKNKPLZO | 65 |
| 0828-29 | β4 | VSYNTKNKPLNFNYSLDKIIVDZO | 66 |
| 0828-30 | β5 | NYSLDKIIVDYNLQSKITLPNDZO | 67 |
| 0828-31 | β6 | LQSKITLPNDRTTPVTKGIPYAZO | 68 |
| 0828-32 | β7 | TPVTKGIPYAPEYKSNAASTIEZO | 69 |
| 0828-33 | β8 | YKSNAASTIEIHNIDDNTIYQYZO | 70 |
| 0828-34 | β9 | NIDDNTIYQYLYAQKSPTTLQRZO | 71 |
| 0828-35 | β10 | AQKSPTTLQRITMTNSVDDALIZO | 72 |
| 0828-36 | β11 | MTNSVDDALINSTKIYSYFPSVZO | 73 |
| 0828-37 | β12 | TKIYSYFPSVISKVNQGAQGILZO | 74 |
| 0828-38 | β13 | KVNQGAQGILFLQWVRDIIDDFZO | 75 |
| 0828-39 | β14 | QWVRDIIDDFTNESSQKTTIDKZO | 76 |
| 0828-40 | β15 | ESSQKTTIDKISDVSTIVPYIGZO | 77 |
| 0828-41 | β16 | DVSTIVPYIGPALNIVKQGYEGZO | 78 |
| 0828-42 | β17 | LNIVKQGYEGNFIGALETTGVVZO | 79 |
| 0828-43 | β18 | IGALETTGVVLLLEYIPEITLPZO | 80 |
| 0828-44 | β19 | LEYIPEITLPVIAALSIAESSTZO | 81 |
| 0828-45 | β20 | AALSIAESSTQKEKIIKTIDNFZO | 82 |
| 0828-46 | β21 | EKIIKTIDNFLEKRYEKWIEVYZO | 83 |

TABLE 1-continued

Overlapping peptides TTx alpha and TTx beta chain
Overlapping 22-mer peptides (overlap 10 amino acids) from
TTx α-chain (38 peptides)
TTx β-chain (71 peptides)

| Synthesis number | Working number | Sequence | SEQ ID NO: |
|---|---|---|---|
| 0828-47 | β22 | KRYEKWIEVYKLVKAKWLGTVNZO | 84 |
| 0828-48 | β23 | VKAKWLGTVNTQFQKRSYQMYRZO | 85 |
| 0828-49 | β24 | FQKRSYQMYRSLEYQVDAIKKIZO | 86 |
| 0828-50 | β25 | EYQVDAIKKIIDYEYKIYSGPDZO | 87 |
| 0828-51 | β26 | YEYKIYSGPDKEQIADEINNLKZO | 88 |
| 0828-52 | β27 | QIADEINNLKNKLEEKANKAMIZO | 89 |
| 0828-53 | β28 | LEEKANKAMININIFMRESSRSZO | 90 |
| 0828-54 | β29 | NIFMRESSRSFLVNQMINEAKKZO | 91 |
| 0828-55 | β30 | VNQMINEAKKQLLEFDTQSKNIZO | 92 |
| 0828-56 | β31 | LEFDTQSKNILMQYIKANSKFIZO | 93 |
| 0828-57 | β32 | QYIKANSKFIGITELKKLESKIZO | 94 |
| 0828-58 | β33 | TELKKLESKINKVFSTPIPFSYZO | 95 |
| 0828-59 | β34 | VFSTPIPFSYSKNLDCWVDNEEZO | 96 |
| 0828-60 | β35 | NLDCWVDNEEDIDVILKKSTILZO | 97 |
| 0828-61 | β36 | DVILKKSTILNLDINNDIISDIZO | 98 |
| 0828-62 | β37 | DINNDIISDISGFNSSVITYPDZO | 99 |
| 0828-63 | β38 | FNSSVITYPDAQLVPGINGKAIZO | 100 |
| 0828-64 | β39 | LVPGINGKAIHLVNNESSEVIVZO | 101 |
| 0828-65 | β40 | VNNESSEVIVHKAMDIEYNDMFZO | 102 |
| 0828-66 | β41 | AMDIEYNDMFNNFTVSFWLRVPZO | 103 |
| 0828-67 | β42 | FTVSFWLRVPKVSASHLEQYGTZO | 104 |
| 0828-68 | β43 | SASHLEQYGTNEYSIISSMKKHZO | 105 |
| 0828-69 | β44 | YSIISSMKKHSLSIGSGWSVSLZO | 106 |
| 0828-70 | β45 | SIGSGWSVSLKGNNLIWTLKDSZO | 107 |
| 0828-71 | β46 | NNLIWTLKDSAGEVRQITFRDLZO | 108 |
| 0828-72 | β47 | EVRQITFRDLPDKFNAYLANKWZO | 109 |
| 0828-73 | β48 | KFNAYLANKWVFITITNDRLSSZO | 110 |
| 0828-74 | β49 | ITITNDRLSSANLYINGVLMGSZO | 111 |
| 0828-75 | β50 | LYINGVLMGSAEITGLGAIREDZO | 112 |
| 0828-76 | β51 | ITGLGAIREDNNITLKLDRCNNZO | 113 |
| 0828-77 | β52 | ITLKLDRCNNNNQYVSIDKFRIZO | 114 |
| 0828-78 | β53 | QYVSIDKFRIFCKALNPKEIEKZO | 115 |
| 0828-79 | β54 | KALNPKEIEKLYTSYLSITFLRZO | 116 |
| 0828-80 | β55 | TSYLSITFLRDFWGNPLRYDTEZO | 117 |
| 0828-81 | β56 | WGNPLRYDTEYYLIPVASSSKDZO | 118 |
| 0828-82 | β57 | LIPVASSSKDVQLKNITDYMYLZO | 119 |
| 0828-83 | β58 | LKNITDYMYLTNAPSYTNGKLNZO | 120 |
| 0828-84 | β59 | APSYTNGKLNIYYRRLYNGLKFZO | 121 |
| 0828-85 | β60 | YRRLYNGLKFIIKRYTPNNEIDZO | 122 |
| 0828-86 | β61 | KRYTPNNEIDSFVKSGDFIKLYZO | 123 |
| 0828-87 | β62 | VKSGDFIKLYVSYNNNEHIVGYZO | 124 |
| 0828-88 | β63 | YNNNEHIVGYPKDGNAFNNLDRZO | 125 |
| 0828-89 | β64 | DGNAFNNLDRILRVGYNAPGIPZO | 126 |
| 0828-90 | β65 | RVGYNAPGIPLYKKMEAVKLRDZO | 127 |
| 0828-91 | β66 | KKMEAVKLRDLKTYSVQLKLYDZO | 128 |
| 0828-92 | β67 | TYSVQLKLYDDKNASLGLVGTHZO | 129 |
| 0828-93 | β68 | NASLGLVGTHNGQIGNDPNRDIZO | 130 |
| 0828-94 | β69 | QIGNDPNRDILIASNWYFNHLKZO | 131 |
| 0828-95 | β70 | ASNWYFNHLKDKILGCDWYFVPZO | 132 |
| 0828-96 | β71 | LKDKILGCDWYFVPTDEGWTNDZO | 133 |

Figure 3:
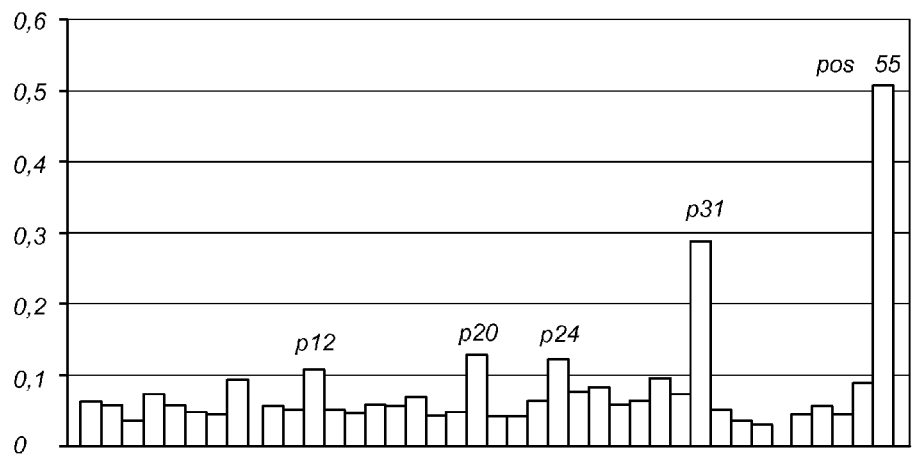
FIG. 3. Results of testing of the 22-mer peptides from the TTx α-chain in the Tettox ELISA.
Figure 4:
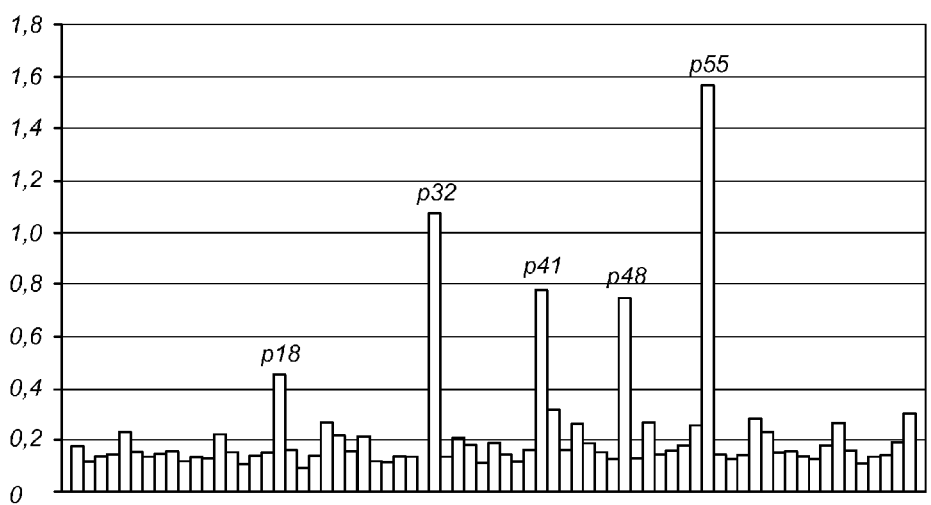
FIG. 4. Results of testing of the 22-mer peptides from the TTx β-chain in the Tettox ELISA.

Z = Aminohexanoicacid
O = Lys(biotin)-amide 2.3. Screening Results for Alfa-Chain and β-Chain Peptides The 22-mer peptides from the TTx α-chain were tested in the Tettox ELISA (FIG. 3). p31 (=α31) was identified to have good binding to TETAQUIN®. The 22-mer peptides from the TTx β-chain were tested in the Tettox ELISA (FIG. 4). p18, p32, p41, p48, p54 and p55 (=β18, β32, β41, β48, β54 and β55) were identified to have good binding to TETAQUIN®.

Conclusion: in TETAQUIN® are antibodies present against α31, β18, β32, β41, β48, β54, β55.

2.4. Screening Results of α31, β18, β32, β41, β48, β54, β55 on Individual Sera

Figure 5A:
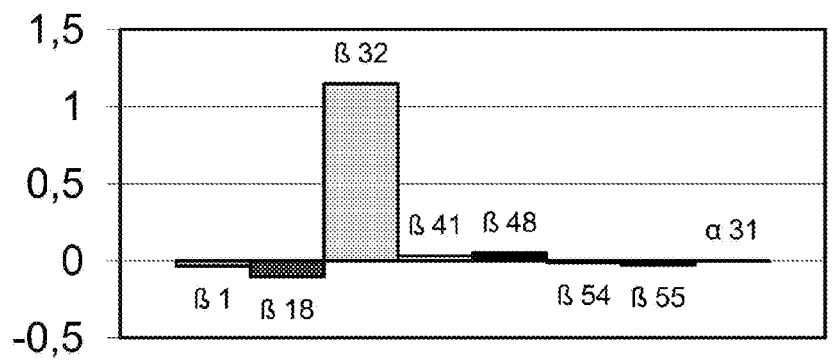
FIGS. 5a-5o. Results of testing of α31, β18, β32, β41, β48, β54, β55 on individual sera using the Tettox ELISA.
Figure 5B:
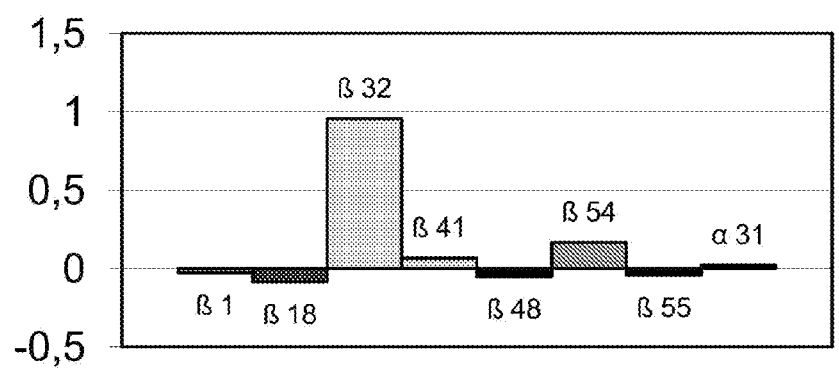
Figure 5C:
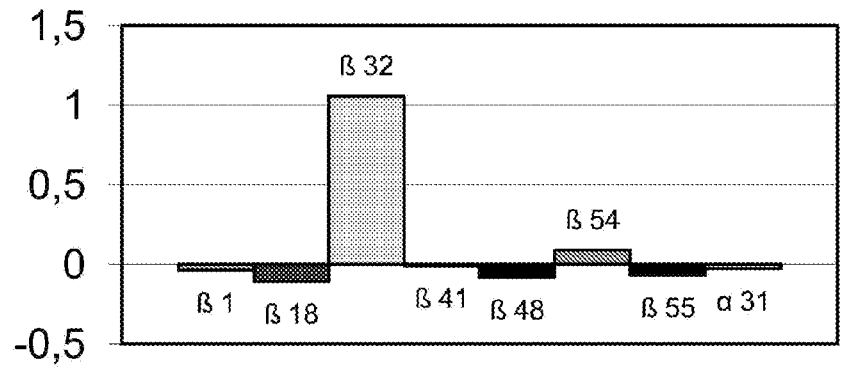
Figure 5D:
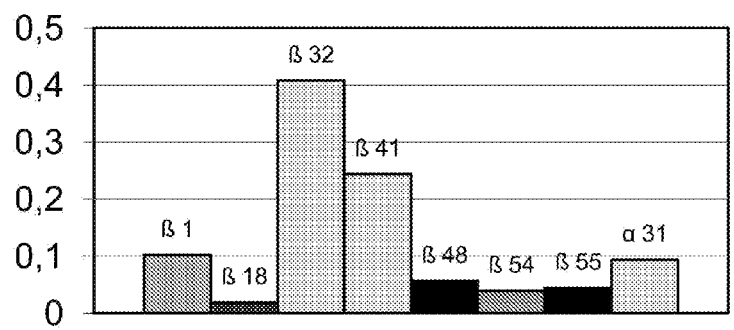
Figure 5E:
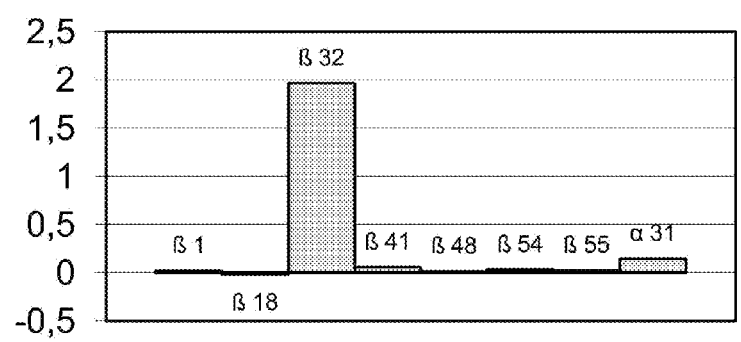
Figure 5F:
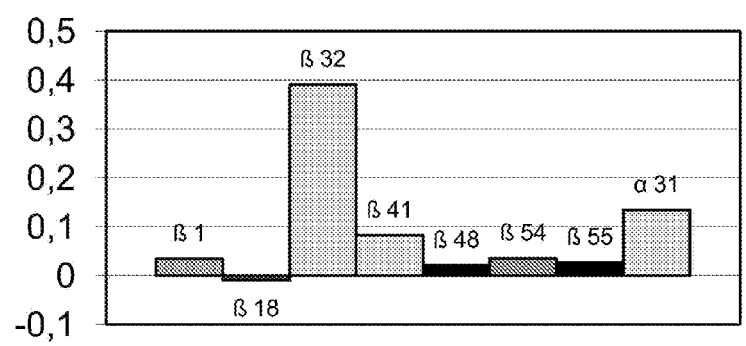
Figure 5G:
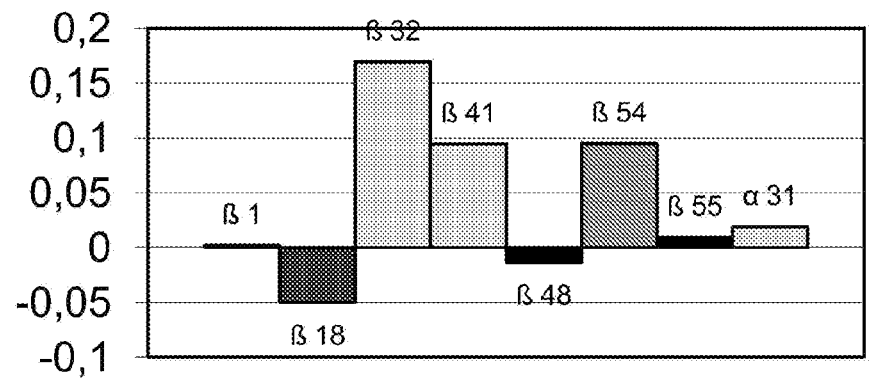
Figure 5H:
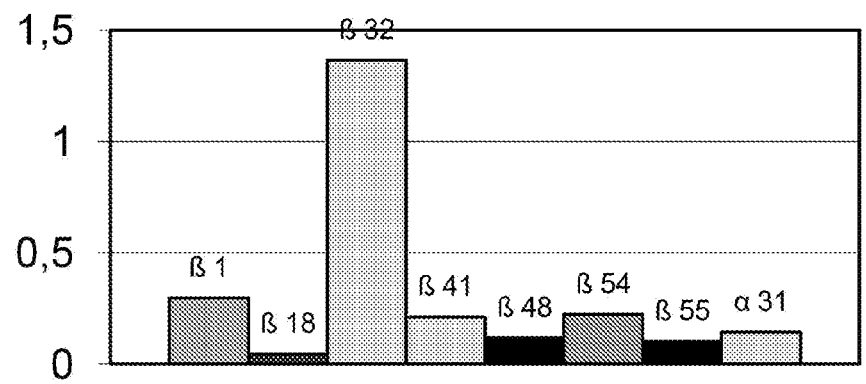
Figure 5I:
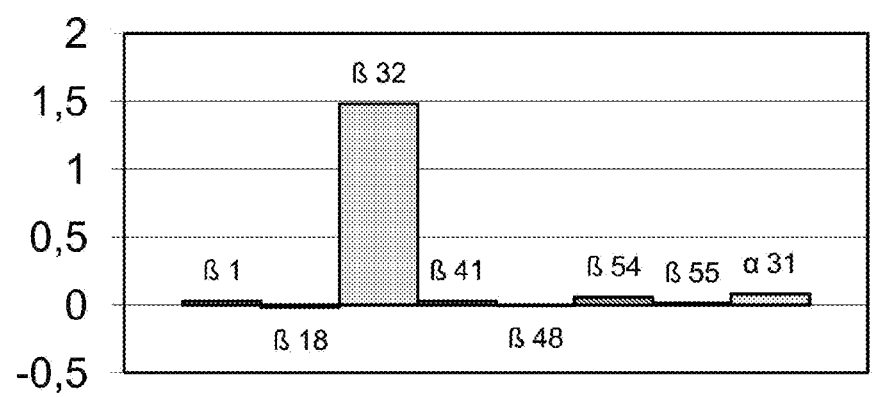
Figure 5J:
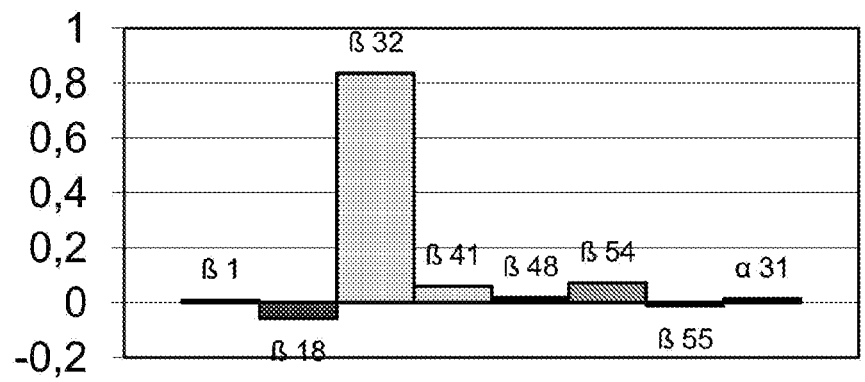
Figure 5K:
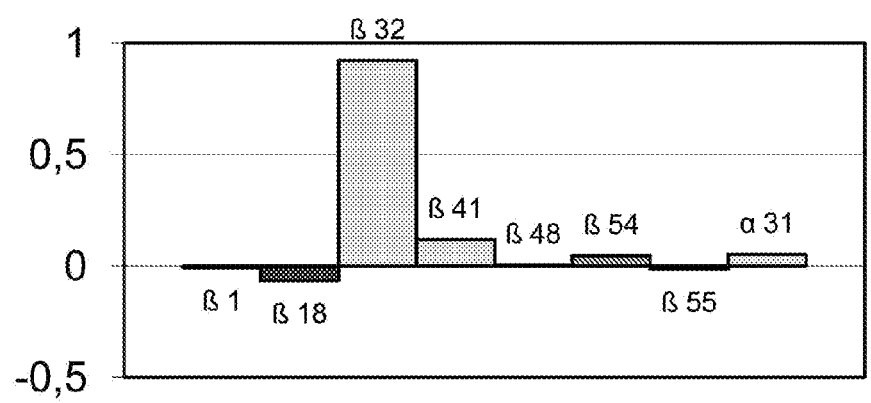
Figure 5L:
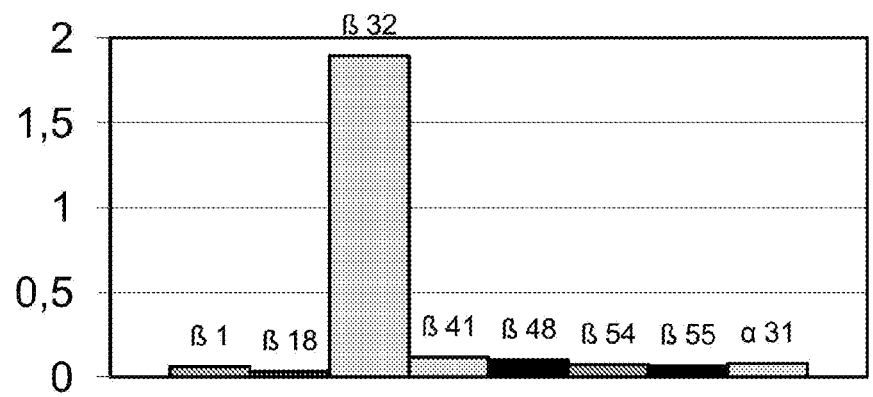
Figure 5M:
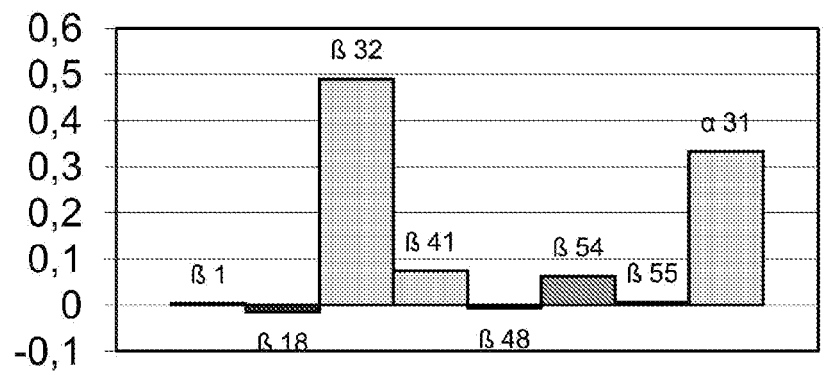
Figure 5N:
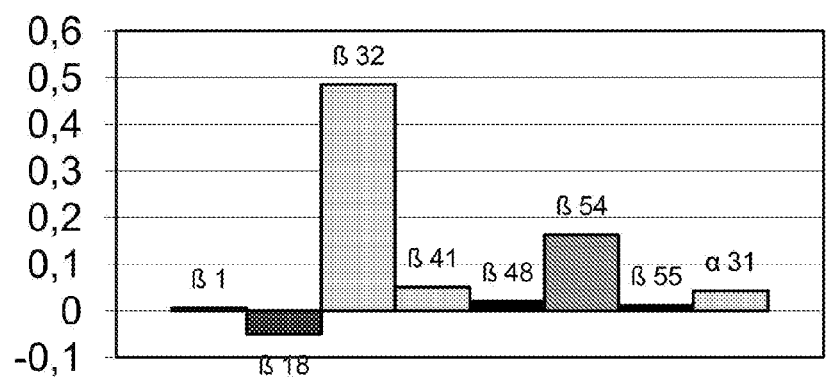
Figure 5O:
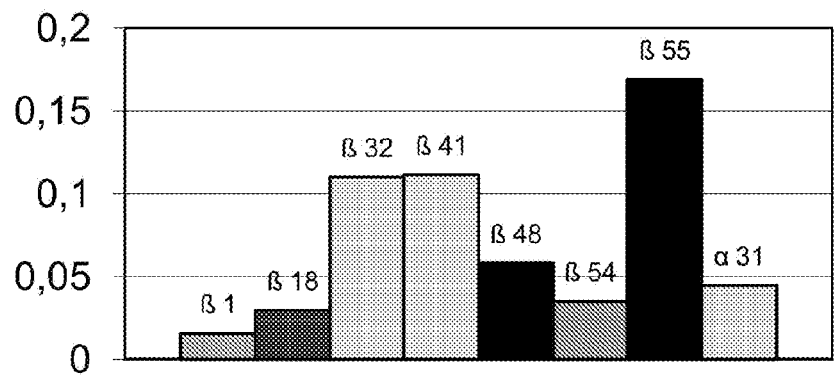
Figure 6:
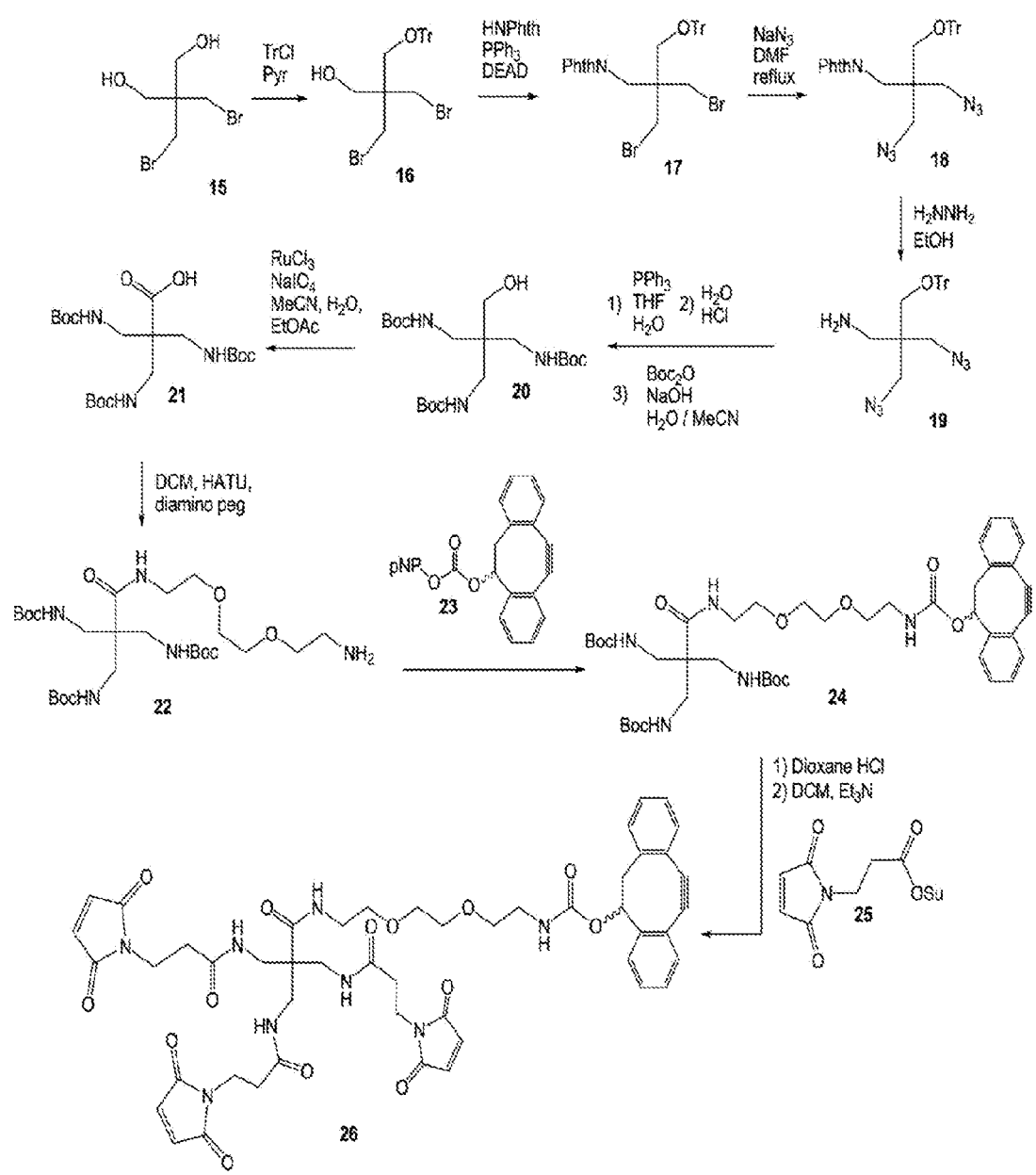

Thereafter, the inventors tested these 7 peptides on individual sera, because an epitope is needed to which every person makes antibodies. The results are shown in FIGS. 5a-5o. All donors have antibodies against only peptide 32 of the beta chain.

2.5. Optimization of the Minimal Peptide that is Needed for Binding.

This peptide was optimised for binding in order to identify the shortest peptides with good binding to TETAQUIN® (see Table 2). Length variants of peptide β32 were tested to determine which part of the peptide is essential for the Ab-binding and which part can be omitted. The higher the OD the better the binding of the peptide by TETAQUIN®.

Conclusion: the shortest peptide that is bound by TETAQUIN® comprises 10 amino acid residues. Further, the peptide can be shortened on the N-terminal side. Best results are obtained with the 22-mer.

2.6. Further Defining the Optimal Peptide

More length variants were tested (shown in table 3).

Conclusion: Peptide should start with FIGIT (SEQ ID NO: 222) and the 18-mer until the other F is the best. Here the inventors also tested if formylation of one or more lysines in the peptide improves the binding. This doesn't seem to be the case. This could have been of importance because TTx is the formylated form of tetanus toxin.

Subsequently, the inventors tested some other length variants and whether C-terminal amino acid residues can be replaced by a longer spacer. In addition it was tested whether it made any difference whether the N-terminus or the C-terminus was biotinylated or whether one of them can best be free. See table 4.

Conclusion: C-terminal amino acid residues are preferably not replaced by just a longer spacer. The peptide works best when the C-terminus is bound and the N-terminus is free. This is important for vaccin design.

2.7. Ala-Scan and Conservative Substitution-Scan

Peptides (FIGITELKKLESKINKVF) (SEQ ID NO: 224) were tested with one Ala-substitution (Table 5) or with one conserved replacement (Table 6). This was done to get a feeling for the relative importance of each amino acid. Positions 3-5 and 11 seem a little bit more important than some other positions. No improved peptides were found.

Table 2. Tettox ELISA of Length Variants of Peptide β-32 Using TETAQUIN®

TABLE 2

Tettox ELISA of length variants of peptide β-32 using TetaQuin ®
Length variants of peptide β-32

| Synthesis number | Working number | Sequence | OD | SEQ ID NO: |
|---|---|---|---|---|
| With linker ||||||
| 0915-1 | P1 | Q Y I K A N S K F I G I T E L K K L E S K I Z O | 1.3 | 023 |
| 0915-2 | P2 | I K A N S K F I G I T E L K K L E S K I Z O | 1.2 | 022 |
| 0915-3 | P3 | Q Y I K A N S K F I G I T E L K K L E S Z O | 1.1 | 021 |
| 0915-4 | P4 | A N S K F I G I T E L K K L E S K I Z O | 1.05 | 020 |
| 0915-5 | P5 | I K A N S K F I G I T E L K K L E S Z O | 0.9 | 019 |
| 0915-6 | P6 | Q Y I K A N S K F I G I T E L K K L Z O | 0.75 | 018 |
| 0915-8 | P7 | S K F I G I T E L K K L E S K I Z O | 1.15 | 017 |
| 0915-9 | P8 | A N S K F I G I T E L K K L E S Z O | 0.85 | 016 |
| 0915-10 | P9 | I K A N S K F I G I T E L K K L Z O | 0.6 | 015 |
| 0915-11 | P10 | Q Y I K A N S K F I G I T E L K Z O | 0.25 | 014 |
| 0915-13 | P11 | F I G I T E L K K L E S K I Z O | 1.0 | 013 |
| 0915-14 | P12 | S K F I G I T E L K K L E S Z O | 0.8 | 012 |
| 0915-15 | P13 | A N S K F I G I T E L K K L Z O | 0.6 | 011 |
| 0915-16 | P14 | I K A N S K F I G I T E L K Z O | 0.2 | 134 |
| 0915-17 | P15 | Q Y I K A N S K F I G I T E Z O | 0.25 | 010 |
| 0915-27 | P16 | G I T E L K K L E S K I Z O | 0.45 | 009 |
| 0915-28 | P17 | F I G I T E L K K L E S Z O | 0.45 | 008 |
| 0915-29 | P18 | S K F I G I T E L K K L Z O | 0.45 | 007 |
| 0915-30 | P19 | A N S K F I G I T E L K Z O | 0.2 | 135 |
| 0915-31 | P20 | I K A N S K F I G I T E Z O | 0.2 | 136 |
| 0915-32 | P21 | Q Y I K A N S K F I G I Z O | 0.2 | 137 |
| 0915-33 | P22 | T E L K K L E S K I Z O | 0.2 | 138 |
| 0915-34 | P23 | G I T E L K K L E S Z O | 0.25 | 005 |
| 0915-35 | P24 | F I G I T E L K K L Z O | 0.35 | 004 |
| 0915-36 | P25 | S K F I G I T E L K Z O | 0.2 | 139 |

TABLE 2-continued

Tettox ELISA of length variants of peptide β-32 using TetaQuin ®

| Synthesis number | Working number | Sequence | OD | SEQ ID NO: |
|---|---|---|---|---|
| | | Length variants of peptide β-32 | | |
| 0915-37 | P26 | A N S K F I G I T E Z O | 0.2 | 140 |
| 0915-38 | P27 | I K A N S K F I G I Z O | 0.2 | 141 |
| 0915-39 | P28 | Q Y I K A N S K F I Z O | 0.2 | 142 |
| 0915-40 | P29 | L K K L E S K I Z O | 0.2 | 143 |
| 0915-41 | P30 | T E L K K L E S Z O | 0.2 | 144 |
| 0915-42 | P31 | G I T E L K K L Z O | 0.2 | 145 |
| 0915-43 | P32 | F I G I T E L K Z O | 0.2 | 146 |
| 0915-44 | P33 | S K F I G I T E Z O | 0.2 | 147 |
| 0915-45 | P34 | A N S K F I G I Z O | 0.2 | 148 |
| 0915-46 | P35 | I K A N S K F I Z O | 0.2 | 149 |
| 0915-47 | P36 | Q Y I K A N S K Z O | 0.2 | 150 |
| | | Without linker | | |
| 0915-1 | P1 | Q Y I K A N S K F I G I T E L K K L E S K I | 1.3 | 023 |
| 0915-2 | P2 | I K A N S K F I G I T E L K K L E S K I | 1.2 | 022 |
| 0915-3 | P3 | Q Y I K A N S K F I G I T E L K K L E S | 1.1 | 021 |
| 0915-4 | P4 | A N S K F I G I T E L K K L E S K I | 1.05 | 020 |
| 0915-5 | P5 | I K A N S K F I G I T E L K K L E S | 0.9 | 019 |
| 0915-6 | P6 | Q Y I K A N S K F I G I T E L K K L | 0.75 | 018 |
| 0915-8 | P7 | S K F I G I T E L K K L E S K I | 1.15 | 017 |
| 0915-9 | P8 | A N S K F I G I T E L K K L E S | 0.85 | 016 |
| 0915-10 | P9 | I K A N S K F I G I T E L K K L | 0.6 | 015 |
| 0915-11 | P10 | Q Y I K A N S K F I G I T E L K | 0.25 | 014 |
| 0915-13 | P11 | F I G I T E L K K L E S K I | 1.0 | 013 |
| 0915-14 | P12 | S K F I G I T E L K K L E S | 0.8 | 012 |
| 0915-15 | P13 | A N S K F I G I T E L K K L | 0.6 | 011 |
| 0915-16 | P14 | I K A N S K F I G I T E L K | 0.2 | 134 |
| 0915-17 | P15 | Q Y I K A N S K F I G I T E | 0.25 | 010 |
| 0915-27 | P16 | G I T E L K K L E S K I | 0.45 | 009 |
| 0915-28 | P17 | F I G I T E L K K L E S | 0.45 | 008 |
| 0915-29 | P18 | S K F I G I T E L K K L | 0.45 | 007 |
| 0915-30 | P19 | A N S K F I G I T E L K | 0.2 | 135 |
| 0915-31 | P20 | I K A N S K F I G I T E | 0.2 | 136 |
| 0915-32 | P21 | Q Y I K A N S K F I G I | 0.2 | 137 |
| 0915-33 | P22 | T E L K K L E S K I | 0.2 | 138 |
| 0915-34 | P23 | G I T E L K K L E S | 0.25 | 005 |
| 0915-35 | P24 | F I G I T E L K K L | 0.35 | 004 |

TABLE 2-continued

Tettox ELISA of length variants of peptide β-32 using TetaQuin ®
Length variants of peptide β-32

| Synthesis number | Working number | Sequence | OD | SEQ ID NO: |
|---|---|---|---|---|
| 0915-36 | P25 | S K F I G I T E L K | 0.2 | 139 |
| 0915-37 | P26 | A N S K F I G I T E | 0.2 | 140 |
| 0915-38 | P27 | I K A N S K F I G I | 0.2 | 141 |
| 0915-39 | P28 | Q Y I K A N S K F I | 0.2 | 142 |
| 0915-40 | P29 | L K K L E S K I | 0.2 | 143 |
| 0915-41 | P30 | T E L K K L E S | 0.2 | 144 |
| 0915-42 | P31 | G I T E L K K L | 0.2 | 145 |
| 0915-43 | P32 | F I G I T E L K | 0.2 | 146 |
| 0915-44 | P33 | S K F I G I T E | 0.2 | 147 |
| 0915-45 | P34 | A N S K F I G I | 0.2 | 148 |
| 0915-46 | P35 | I K A N S K F I | 0.2 | 149 |
| 0915-47 | P36 | Q Y I K A N S K | 0.2 | 150 |

TABLE 3

Tettox ELISA of length variants of peptide β-32 using TetaQuin ®

| Synthesis number | Working number | Sequence | OD | SEQ ID NO: |
|---|---|---|---|---|
| 0925-52 | 1 | F I G I T E L K K L E S K I N K V F S T Z O | 1.85 | 151 |
| 0925-53 | 2 | F I G I T E L K K L E S K I N K V F S Z O | 1.90 | 152 |
| 0925-54 | 3 | F I G I T E L K K L E S K I N K V F Z O | 2.30 | 153 |
| 0925-55 | 4 | F I G I T E L K K L E S K I N K V Z O | 2.00 | 154 |
| 0925-56 | 5 | F I G I T E L K K L E S K I N K Z O | 1.55 | 155 |
| 0925-57 | 6 | F I G I T E L K K L E S K I N Z O | 1.65 | 156 |
| 0925-58 | 7 | I G I T E L K K L E S K I N Z O | 1.45 | 157 |
| 0925-59 | 8 | G I T E L K K L E S K I N K Z O | 0.75 | 158 |
| 0925-60 | 9 | I T E L K K L E S K I N K V Z O | | 159 |
| 0925-61 | 10 | T E L K K L E S K I N K V F Z O | 0.35 | 160 |
| 0925-62 | 11 | E L K K L E S K I N K V F S Z O | 0.35 | 161 |
| 0925-63 | 12 | L K K L E S K I N K V F S T Z O | 0.40 | 162 |
| 0925-64 | 13 | F I G I T E L J K L E S K I Z O | 1.70 | 163 |
| 0925-65 | 14 | F I G I T E L K J L E S K I Z O | 1.50 | 164 |
| 0925-66 | 15 | F I G I T E L K K L E S J I Z O | 2.10 | 165 |
| 0925-67 | 16 | F I G I T E L J J L E S K I Z O | 1.15 | 166 |
| 0925-68 | 17 | F I G I T E L J K L E S J I Z O | | 167 |
| 0925-69 | 18 | F I G I T E L K J L E S J I Z O | 1.65 | 168 |

TABLE 3-continued

| Tettox ELISA of length variants of peptide β-32 using TetaQuin ® | | | | |
|---|---|---|---|---|
| Synthesis number | Working number | Sequence | OD | SEQ ID NO: |
| 0925-70 | 19 | F I G I T E L J J L E S J I Z O | 1.00 | 169 |
| Neg. control | | | 0.30 | |

Z = Ahx
O = Lys(biotin)
J = Lys(formyl)

TABLE 4

| Effect of longer spacer and C- versus N-terminal biotinylation | | |
|---|---|---|
| J Z Z S K F I G I T E L K K L E S K I N K V F | 0.47 | SEQ ID NO: 170 |
| J Z S K F I G I T E L K K L E S K I N K V F | 0.28 | SEQ ID NO: 170 |
| J Z Z F I G I T E L K K L E S K I N K V F | 0.22 | SEQ ID NO: 171 |
| J Z F I G I T E L K K L E S K I N K V F | 0.17 | SEQ ID NO: 171 |
| F I G I T E L K K L E S K I N K V F Z Z O | 1.16 | SEQ ID NO: 172 |
| F I G I T E L K K L E S K I N K V Z Z O | 0.68 | SEQ ID NO: 173 |
| F I G I T E L K K L E S K I N K Z Z O | 0.65 | SEQ ID NO: 174 |
| F I G I T E L K K L E S K I N Z Z O | 0.64 | SEQ ID NO: 175 |
| F I G I T E L K K L E S K I Z Z O | 0.79 | SEQ ID NO: 176 |
| Q Y I K A N S K F I G I T E L K K L E S K I Z O (b32) | 1.16 | SEQ ID NO: 177 |
| S L T D L G G E L C I K I K N E D L T F I A Z O (b1, neg contr.) | 0.12 | SEQ ID NO: 178 |

Z = Ahx
O = Lys(biotin)
J = Biotin

TABLE 5

| Ala scan of FIGITELKKLESKINKVF | | | | | |
|---|---|---|---|---|---|
| | | | ELISA OD | | SEQ |
| # | SYNTH # | SEQUENCE 1 2 3 4 5 6 7 8 9 0 1 2 3 4 5 6 7 8 | TETAQUIN | SERUM 034960 | ID NO: |
| 1 | 0942-09 | F I G I T E L K K L E S K I N K V F Z O | 1.26 | 1.36 | 179 |
| 2 | 0942-10 | A I G I T E L K K L E S K I N K V F Z O | 1.12 | 1.29 | 180 |
| 3 | 0942-11 | F A G I T E L K K L E S K I N K V F Z O | 1.04 | 1.18 | 181 |
| 4 | 0942-12 | F I A I T E L K K L E S K I N K V F Z O | 0.65 | 0.23 | 182 |
| 5 | 0942-13 | F I G A T E L K K L E S K I N K V F Z O | 0.30 | 0.18 | 183 |
| 6 | 0942-14 | F I G I A E L K K L E S K I N K V F Z O | 0.38 | 0.16 | 184 |
| 7 | 0942-15 | F I G I T A L K K L E S K I N K V F Z O | 1.24 | 1.28 | 185 |
| 8 | 0942-16 | F I G I T E A K K L E S K I N K V F Z O | 0.90 | 0.91 | 186 |
| 9 | 0942-17 | F I G I T E L A K L E S K I N K V F Z O | 0.62 | 0.65 | 187 |
| 10 | 0942-18 | F I G I T E L K A L E S K I N K V F Z O | 1.06 | 1.22 | 188 |
| 11 | 0942-19 | F I G I T E L K K A E S K I N K V F Z O | 0.70 | 0.71 | 189 |

TABLE 5-continued

Ala scan of FIGITELKKLESKINKVF

| # | SYNTH # | SEQUENCE 1 2 3 4 5 6 7 8 9 0 1 2 3 4 5 6 7 8 | ELISA OD TETAQUIN | ELISA OD SERUM 034960 | SEQ ID NO: |
|---|---|---|---|---|---|
| 12 | 0942-20 | F I G I T E L K K L A S K I N K V F Z O | 0.85 | 0.91 | 190 |
| 13 | 0942-21 | F I G I T E L K K L E A K I N K V F Z O | 1.27 | 1.48 | 191 |
| 14 | 0942-22 | F I G I T E L K K L E S A I N K V F Z O | 1.10 | 1.27 | 192 |
| 15 | 0942-23 | F I G I T E L K K L E S K A N K V F Z O | 0.88 | 1.08 | 193 |
| 16 | 0942-24 | F I G I T E L K K L E S K I A K V F Z O | 1.37 | 1.29 | 194 |
| 17 | 0942-25 | F I G I T E L K K L E S K I N A V F Z O | 1.30 | 1.28 | 195 |
| 18 | 0942-26 | F I G I T E L K K L E S K I N K A F Z O | 1.24 | 1.39 | 196 |
| 19 | 0942-27 | F I G I T E L K K L E S K I N K V A Z O | 1.26 | 1.20 | 197 |

TABLE 6

Conservative substitutions scan of FIGITELKKLESKINKVF

| # | SYNTH # | SEQUENCE 1 2 3 4 5 6 7 8 9 0 1 2 3 4 5 6 7 8 | ELISA OD TETAQUIN | ELISA OD SERUM 034960 | SEQ ID NO: |
|---|---|---|---|---|---|
| 1 | 0942-09 | F I G I T E L K K L E S K I N K V F Z O | 1.26 | 1.36 | 198 |
| 20 | 0942-28 | Y I G I T E L K K L E S K I N K V F Z O | 1.23 | 1.30 | 199 |
| 21 | 0942-29 | F L G I T E L K K L E S K I N K V F Z O | 1.19 | 1.29 | 200 |
| 22 | 0942-30 | F I S I T E L K K L E S K I N K V F Z O | 1.10 | 1.32 | 201 |
| 23 | 0942-31 | F I G L T E L K K L E S K I N K V F Z O | 0.97 | 1.19 | 202 |
| 24 | 0942-32 | F I G I S E L K K L E S K I N K V F Z O | 0.83 | 0.70 | 203 |
| 25 | 0942-33 | F I G I T D L K K L E S K I N K V F Z O | 1.01 | 0.95 | 204 |
| 26 | 0942-34 | F I G I T E I K K L E S K I N K V F Z O | 0.72 | 0.80 | 205 |
| 27 | 0942-35 | F I G I T E L R K L E S K I N K V F Z O | 1.02 | 0.90 | 206 |
| 28 | 0942-36 | F I G I T E L K R L E S K I N K V F Z O | 1.12 | 1.23 | 207 |
| 29 | 0942-37 | F I G I T E L K K I E S K I N K V F Z O | 1.11 | 1.14 | 208 |
| 30 | 0942-38 | F I G I T E L K K L D S K I N K V F Z O | 0.41 | 0.37 | 209 |
| 31 | 0942-39 | F I G I T E L K K L E T K I N K V F Z O | 0.88 | 1.04 | 210 |
| 32 | 0942-40 | F I G I T E L K K L E S R I N K V F Z O | 1.19 | 1.27 | 211 |
| 33 | 0942-41 | F I G I T E L K K L E S K L N K V F Z O | 1.11 | 1.32 | 212 |
| 34 | 0942-42 | F I G I T E L K K L E S K I Q K V F Z O | 1.41 | 1.26 | 213 |
| 35 | 0942-43 | F I G I T E L K K L E S K I N R V F Z O | 1.26 | 1.31 | 214 |
| 36 | 0942-44 | F I G I T E L K K L E S K I N K L F Z O | 1.30 | 1.47 | 215 |
| 37 | 0942-45 | F I G I T E L K K L E S K I N K V Y Z O | 1.11 | 1.23 | 216 |

Z = Ahx
O = Lys(biotin)

It is known that the uptake of the antibodies by the immune cells via Fc receptors can be improved by antibody cross-linking. We therefore generate multimers of the above-identified peptides and compare the efficacy of multimers to monomers. This comparison is performed using CTL- and helper epitopes of HPV16E7 and ovalbumin (OVA) in in vitro and in vivo testing (see below). In addition, some of the above mentioned constructs are synthesized in fluorescent form in order to be able to investigate the uptake of the constructs in various cell types, including dendritic cells (DC).

2.8. Validation of the Results with the Constructs in Mice (In Vivo)

Mice are repeatedly vaccinated with TTd to induce high antibody titers against TTd (determined with ELISA). Subsequently these mice will be challenged with a single dose of one of the above-identified peptides that is linked to OVA.

The animals are monitored for:
- Efficient T cell priming by means of proliferation of CFSE labelled TCR transgenic T cells and quantification of the numbers of specific CD8 T cells in wild type mice using specific MHC class I tetramers.
- Protection and therapeutic potency of the constructs against tumours (OVA-expressing tumour cells B16-OVA)

Since the B cell repertoire in mice against foreign antigens is huge it can be expected that the antibody response against linear TTd epitopes in mice is very similar tot that of humans. In case the responses in mice will be significantly different from that in humans, which will be clear from the vaccination studies in mice, the Medarex mice will be used that express a humanized B-cell Ig locus system. Alternatively, these mice (which are tolerant for human antibodies) can be used to test the constructs by pre-loading these with well-defined, clinical grade antibodies (TETAQUIN®). These preformed complexes will be injected followed by T cell priming analysis. In this system murine Fc receptors are considered compatible with human antibody-antigen complexes.

2.9. Validation of the Results with the Constructs on Human DC In Vitro

The above-identfied peptides are tested for their functionality in the human system on human monocyte-derived dendritic cells (MoDC) in vitro. Peptide-constructs are incubated with titrated amounts of anti-TTd antibodies (TETAQUIN®) and the formed complexes cultured together with MoDC and antigen presentation and DC maturation studies are carried out.

Peptide-peptide constructs consist of HPV derived peptide sequences harbouring well-defined HLA-A2 or an HLA-DR3 restricted epitopes to test recognition by HPV-specific CD8 T cells and CD4 T cells respectively.

DC maturation is tested by staining with specific antibodies against DC maturation markers CD80, CD86, CD40, MHC class II and MHC class I by FACScan analysis.

2.10 Vaccination of Mice with Construct 33 with or without Prior Administration of Specific Antibodies In order to determine the enhanced priming capacities of construct 33 in the presence of TTE specific antibodies in vivo, we vaccinated mice with a suboptimal dose of construct 33 subcutaneously in saline. One group of mice was injected intravenously with TTE specific antibodies (ProtG purified rabbit anti TTE antibodies) 4 hours prior to vaccination with construct 33. 7 days after vaccination, mice were sacrificed and draining lymph node was analyzed by flow-cytometry for SIINFEKL-specific (SEQ ID NO: 219) $CD8^+$ T-cells, using both SIINFEKL-tetramers (SEQ ID NO: 219) (FIG. 9*a*), and SIINFEKL (SEQ ID NO: 219) specific cytokine secretion assay (FIG. 9*b*). As is shown in FIGS. 9*a* and 9*b*, a higher percentage of SIINFEKL (SEQ ID NO: 219) specific $CD8^+$ T-cells is present in mice that received TTE-specific antibodies and construct 33, as opposed to mice that received construct 33 alone, signifying superior priming capacity of construct 33 in the presence of TTE-specific antibodies.

The invention claimed is:

1. A conjugate, comprising a peptide conjugated to an antigen or to a vehicle comprising an antigen, wherein the peptide comprises: the amino acid sequence selected from any one of SEQ ID NOS: 8, 9, 12, 13, 16, 17, 19-24, 151-158, 163-166, 168, 172-176, 179-182, 185-208 and 210-216;
   wherein the peptide is less than 50 amino acid residues in length and
   wherein the antigen is not a peptide that binds to anti-tetanus toxoid or anti-tetanus toxin antibodies.

2. A conjugate according to claim 1, wherein the peptide consists of the amino acid sequence of any one of SEQ ID NOS: 8, 9, 12, 13, 16, 17, 19-24, 151-158, 163-166, 168, 172-176, 179-182, 185-208 and 210-216.

3. The conjugate according to claim 1, wherein the antigen or the vehicle comprising the antigen is conjugated to the C-terminus of the peptide.

4. The conjugate according to claim 1, wherein 2 to 20 peptides are bound to the antigen or the vehicle comprising the antigen, wherein each one of the 2 to 20 peptides are as defined in claim 1.

5. A pharmaceutical composition comprising a conjugate according to claim 1.

6. A conjugate according to claim 2, wherein the peptide consists of SEQ ID NO: 24.

7. A conjugate according to claim 1, wherein the antigen is an antigen of cancer or pathogen.

8. A conjugate according to claim 7, wherein said pathogen is a viral, bacterial, fungal or parasitic pathogen.

9. A conjugate according to claim 7, wherein said cancer is selected among lung, colon, esophagus, ovary, pancreas, skin, gastric, head and neck, bladder, sarcoma, prostate, hepatocellular, brain, adrenal, breast, endometrial, mesothelioma, renal, thyroid, hematological, carcinoid, melanoma, parathyroid, cervix, neuroblastoma, Wilms, testes, pituitary or pheochromocytoma cancers.

10. A peptide comprising: the amino acid residues selected from any one of SEQ ID NOS: 8, 9, 12, 13, 16, 17, 19-24, 151-158, 163-166, 168, 172-176, 179-182, 185-208 and 210-216;
    wherein the peptide is less than 50 amino acids in length and wherein any possible further amino acid residues linked to the C terminus of the amino acid residues selected from the SEQ ID NO are not derived from the tetanus toxin beta chain.

11. A peptide according to claim 10 consisting of the amino acid sequence of any one of SEQ ID NOS: 8, 9, 12, 13, 16, 17, 19-24, 151-158, 163-166, 168, 172-176, 179-182, 185-208 and 210-216.

12. A peptide according to claim 11, wherein the peptide consists of SEQ ID NO: 24.

13. A method of aiding prevention or treatment of cancer or an infectious disease in a subject, comprising administering to a subject in need thereof a conjugate according to claim 1.

14. The method according to claim 13, wherein the subject has antibodies against tetanus toxin or tetanus toxoid.

15. The method according to claim 13, wherein the subject is a subject to whom a vaccine for generating circulating antibodies to tetanus toxin has been administered at least 2 weeks prior to administering the conjugate.

16. A pharmaceutical composition comprising a peptide according to claim 10.

* * * * *